US008420354B2

(12) United States Patent
Sznaidman et al.

(10) Patent No.: US 8,420,354 B2
(45) Date of Patent: *Apr. 16, 2013

(54) METHODS TO MANUFACTURE 1,3-DIOXOLANE NUCLEOSIDES

(75) Inventors: Marcos Sznaidman, Durham, NC (US); George R. Painter, Chapel Hill, NC (US); Merrick R. Almond, Apex, NC (US); Darryl G. Cleary, Chapel Hill, NC (US); Amir Pesyan, Salt Lake City, UT (US)

(73) Assignee: Emory University, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/870,319

(22) Filed: Aug. 27, 2010

(65) Prior Publication Data

US 2011/0130559 A1    Jun. 2, 2011

Related U.S. Application Data

(63) Continuation of application No. 11/051,287, filed on Feb. 3, 2005, now Pat. No. 7,785, 839.

(60) Provisional application No. 60/541,545, filed on Feb. 3, 2004.

(51) Int. Cl.
*C12P 19/00* (2006.01)
*C12P 19/38* (2006.01)
*C12P 19/40* (2006.01)
*C07D 239/00* (2006.01)
*C07D 239/02* (2006.01)
*C07D 473/00* (2006.01)

(52) U.S. Cl.
USPC ............... 435/72; 435/87; 435/88; 544/242; 544/264

(58) Field of Classification Search .................. None
See application file for complete search history.

(56) References Cited

U.S. PATENT DOCUMENTS

| | | | |
|---|---|---|---|
| 5,041,449 A | 8/1991 | Belleau et al. |
| 5,179,104 A | 1/1993 | Chu et al. |
| 5,204,466 A | 4/1993 | Liotta et al. |
| 5,210,085 A | 5/1993 | Liotta et al. |
| 5,270,315 A | 12/1993 | Belleau et al. |
| 5,276,151 A | 1/1994 | Liotta |
| 5,444,063 A | 8/1995 | Schinazi |
| 5,539,116 A | 7/1996 | Liotta et al. |
| 5,663,320 A | 9/1997 | Mansour et al. |
| 5,684,010 A | 11/1997 | Schinazi |
| 5,684,164 A | 11/1997 | Belleau et al. |
| 5,693,787 A | 12/1997 | Mansour et al. |
| 5,696,254 A | 12/1997 | Mansour et al. |
| 5,700,937 A | 12/1997 | Liotta et al. |
| 5,728,575 A | 3/1998 | Liotta et al. |
| 5,744,596 A | 4/1998 | Mansour et al. |
| 5,756,706 A | 5/1998 | Mansour et al. |
| 5,763,606 A | 6/1998 | Mansour et al. |
| 5,767,122 A | 6/1998 | Chu et al. |
| 5,792,773 A | 8/1998 | Chu et al. |
| 5,814,639 A | 9/1998 | Liotta et al. |
| 5,827,727 A | 10/1998 | Liotta et al. |
| 5,830,898 A | 11/1998 | Schinazi |
| 5,834,474 A | 11/1998 | Schinazi |
| 5,852,027 A | 12/1998 | Liotta et al. |
| 5,892,025 A | 4/1999 | Liotta et al. |
| 5,914,331 A | 6/1999 | Liotta et al. |
| 5,914,400 A | 6/1999 | Liotta et al. |
| 5,922,867 A | 7/1999 | Mansour et al. |
| 5,925,643 A | 7/1999 | Chu |
| 6,069,252 A | 5/2000 | Liotta et al. |
| 6,153,751 A | 11/2000 | Liotta et al. |
| 6,215,004 B1 | 4/2001 | Painter et al. |
| 6,346,627 B1 | 2/2002 | Liotta et al. |
| 6,358,963 B1 | 3/2002 | Nguyen-Ba |
| 6,518,425 B1 | 2/2003 | Painter et al. |
| 6,642,245 B1 | 11/2003 | Liotta et al. |
| 6,703,396 B1 | 3/2004 | Liotta et al. |
| 6,855,821 B2 | 2/2005 | Du et al. |
| 7,160,999 B2 | 1/2007 | Liotta et al. |
| 7,785,839 B2 * | 8/2010 | Sznaidman et al. ............ 435/72 |

FOREIGN PATENT DOCUMENTS

| | | |
|---|---|---|
| EP | 0 337 713 | 10/1989 |
| EP | 0 515 156 | 11/1992 |
| EP | 0 656 778 | 5/2001 |
| WO | WO 92/14729 | 9/1992 |
| WO | WO 94/29301 | 12/1994 |
| WO | WO 00/09494 | 2/2000 |
| WO | WO 00/47759 | 8/2000 |
| WO | WO 01/58894 | 8/2001 |
| WO | WO 03/062229 | 7/2003 |

OTHER PUBLICATIONS

Smith and March "March's Advanced Organic Chemistry, Fifth Edition," John Wiley & Sons, New York, NY, 2001, only pp. 152 and 200 supplied.*
Niedballa and Vorbrüggen, "A General Synthesis of Pyrimidine Nucleosides," Angewandte Chemie International Edition, 9(6), 461-462 (Jun. 1970).*
Vorbrüggen and Niedballa, "Eine Einfache Synthese von 5-Azapyrimidin-nucleosiden," Tetrahedron Letters, No. 41, 3571-3574 (1970).*
Vorbrüggen and Ruh-Pohlenz, Handbook of Nucleoside Synthesis, John Wiley & Sons, Inc., New York, NY, 2001, only title page, first contents page, and text pp. 10-24 and 591-594 supplied.*
Barton, P., and Page, M.I., "The esterase catalysed resolution of lactones and spirodilactone," *J. Chem. Soc., Perkin Trans. 2*, 1993, pp. 2317-2318.

(Continued)

Primary Examiner — Lawrence E Crane
(74) Attorney, Agent, or Firm — King & Spalding

(57) ABSTRACT

This application provides a process for preparing enantiomerically pure β-D-dioxolane nucleosides. In particular, a new synthesis of (−)-DAPD, suitable for large scale development, is described. In one embodiment the invention provides a process for preparing a substantially pure β-D- or β-L-1,3-dioxolane nucleosides comprising a) preparing or obtaining an esterified 2,2-dialkoxy ethanol; b) cyclizing the esterified 2,2-dialkoxy ethanol with glycolic acid to obtain a 1,3-dioxolane lactone; c) resolving the 1,3-dioxolane lactone to obtain a substantially pure D- or L-lactone; d) selectively reducing and activating the D- or L-chiral lactone to obtain a substantially pure D- or L-1,3-dioxolane; e) coupling the D- or L-1, 3-dioxolane to an activated and/or protected purine or pyrimidine base; and f) optionally purifying the nucleoside to obtain a substantially pure protected β-D- or β-L-1,3-dioxolane nucleoside.

18 Claims, 13 Drawing Sheets

OTHER PUBLICATIONS

Belleau, B., et al., "Design and activity of a novel class of nucleoside analogs effective against HIV-1," 5th Int. Conf. on AIDS, Montreal, Canada; Jun. 4-9, 1990; Abstr. No. T.C.O.1. and Poster No. 4576.

Belleau, B., et al., "Oxidative degradation of L-ascorbic acid acetals to 2',3'-dideoxy-3'-oxaribofuranosides. Synthesis of enantiomerically pure 2',3'-dideoxy-3'-oxacytidine stereoisomers as potential antiviral agents," *Tetrahedron Lett.*, 1992, vol. 30, No. 40, pp. 6949-6952.

Boaz, N. W., and Zimmerman, R.L., "Amine assisted enzymatic esterification of 1,2-diol monotosylates," *Tetrahedron: Asymmetry*, 1994, vol. 5, No. 2, pp. 153-156.

Chen, C.-S., et al., "Quantitative analysis of biochemical kinetic resolutions of enantiomers," *J. Am. Chem. Soc.*, 1982, vol. 104, No. 25, pp. 7294-7299.

Choi, W.-B., et al., "In situ complexation directs the stereochemistry of N-glycosylation in the synthesis of oxathiolanyl and dioxolanyl nucleoside analogues," *J. Am. Chem. Soc.*, 1991, vol. 113, No. 24, pp. 9377-9379.

Chu, C.K., et al., "Asymmetric synthesis of enantiomerically pure (-)-(1'R,4'R)-dioxolane-thymine and its anti-HIV activity," *Tetrahedron Lett.*, 1991, vol. 32, No. 31, pp. 3791-3794.

Corbett, A.H., and Rublein, J.C., "DAPD," *Curr. Opin. Investig. Drugs*, 2001, vol. 2, No. 3, pp. 348-353.

Duan, G., and Chen, J.Y., "Effects of polar additives on the enzyme enantioselectivity of an esterification reaction in organic solvents," *Biotechnology Letters*, 1994, vol. 16, No. 10, pp. 1065-1068.

Evans, C.A., et al., "Divergent asymmetric syntheses of dioxolane nucleoside analogues," *Tetrahedron: Asymmetry*, 1993, vol. 4, No. 11, pp. 2319-2322.

Faber, K., et al., "Selectivity-enhancement of hydrolase reactions," *Biocatalysis*, 1993, vol. 8, pp. 91-132.

Fouque, E., and Rousseau, G., "Enzymatic resolution of medium-ring lactones. Synthesis of (S)-(+)-phoracantholide I," *Synthesis*, 1989, pp. 661-666.

Furman, P.A., et al., "DAPD," *Drugs of the Future*, 2000, vol. 25, No. 5, pp. 454-461.

Gu, Z., et al., "Mechanism of action and in vitro activity of 1',3'-dioxolanylpurine nucleoside analogues against sensitive and drug-resistant human immunodeficiency virus type 1 variants," *Antimicrob. Agents Chemother.*, 1999, vol. 43, No. 10, pp. 2376-2382.

Hansen, T.V., et al., Co-solvent enhancement of enantioselectivity in lipase-catalysed hydrolysis of racemic esters. A process for production of homochiral C-3 building blocks using lipase B from *Candida antarctica*, *Tetrahedron: Asymmetry*, 1995, vol. 6, No. 2, pp. 499-504.

Jaques, J., et al., *Enantiomers, Racemates, and Resolutions*, Wiley, New York, 1981, title page, bibliographic data and table of contents.

Jin, H., et al., "Unexpected effects of Lewis acids in the synthesis of optically pure 2'-deoxy-3'-oxacytidine nucleoside analogues," *Tetrahedron: Asymmetry*, 1993, vol. 4, No. 2, pp. 211-214.

Kadhim, S.A., et al., "Potent antitumor activity, of a novel nucleoside analogue, BCH-4556 (beta-L-dioxolane-cytidine), in human renal cell carcinoma xenograft tumor models," *Cancer Res.*, 1997, vol. 57, No. 21, pp. 4803-4810.

Kim, H., et al. "Asymmetric Synthesis of 1,3-Dioxolane-Pyrimidine Nucleosides and their Anti-HIV Activity," *J. Med. Chem.*, 1992, vol. 35, No. 11, pp. 1987-1995.

Kim, H., et al., "Potent Anti-HIV and Anti-HBV Activities of (-)-L-β-Dioxolane-C and (+)-L-β-Dioxolane-C and Their Asymmetric Syntheses," *Tetrahedron Lett.*, 1992, vol. 33, No. 46, pp. 6899-6902.

Kim, H., et al., "1,3-Dioxolanylpurine Nucleosides (2R,4R) and (2R,4S) with Selective Anti-HIV-1 Activity in Human Lymphocytes," *J Med. Chem.*, 1993, vol. 36, No. 1, pp. 30-37.

Kim, H., et al., "L-β-(2S,4S)- and L-α-(2S,4R)-dioxolanyl nucleosides as potential anti-HIV agents: Asymmetric synthesis and structure-activity relationships," *J Med. Chem.*, 1993, vol. 36, No. 5, pp. 519-528.

Meshaw, J.P., et al., "Dioxolane guanosine, the active form of the prodrug diaminopurine dioxolane, is a potent inhibitor of drug-resistant HIV-1 isolates from patients for whom standard nucleoside therapy fails," *J. Acquir. Immune Defic. Syndr.*, 2002, vol. 29, No. 1, pp. 11-20.

Norbeck, D.W., et al., "A new 2',3'-dideoxynucleoside prototype with in vitro activity against HIV," *Tetrahedron Lett.*, 1989, vol. 30, No. 46, pp. 6263-6266.

Rajagopalan, P., et al., "Pharmacokinetics of (-)-β-D-2,6-diaminopurine dioxolane and its metabolite, dioxolane guanosine, in woodchucks (*Marmota monax*)," *Antiviral Chem. Chemother.*, 1996, vol. 7, No. 2, pp. 65-70.

Popp, A., et al. "Enzymatic Kinetic Resolution of 1,3-Dioxolan-4-one and 1,3-Oxathiolan-5-one Derivatives: Synthesis of the Key Intermediate in the Industrial Synthesis of the Nucleoside Reverse Transcriptase Inhibitor Amdoxovir," *Advanced Synthesis & Catalysis*, 2004, vol. 346, No. 6, pp. 682-690.

Siddiqui, A., et al., "Antiviral optically pure dioxolane purine nucleoside analogues," *Bioorg. Med. Chem. Lett.*, 1993, vol. 3, No. 8, pp. 1543-1546.

Sznaidman, M.L., et al.; Synthesis of (-) DAPD; *Nucleosides, Nucleotides and Nucleic Acids*, 2004, vol. 23, No. 12, pp. 1875-18875.

Thomas, S.B., et al., "Preparative separation and analysis of the enantiomers of [3H]Abbott-69992, an HIV anti-infective nucleoside, by ligand-exchange high-performance liquid chromatography," *J. Chromat.*, 1991, vol. 586, pp. 265-270.

Wilson, L.J., et al., "The synthesis and anti-HIV activity of pyrimidine dioxolanyl nucleosides," *Biorganic & Med. Chem. Letters*, 1993, vol. 3, No. 2, pp. 169-174.

Nguyen-Ba, et al., "Synthesis of N-1-oxypyrimidine 1,3-dioxolane and 1,3-oxathiolane nucleosides," *Chem. Commun.* 2000, pp. 2311-2312.

* cited by examiner

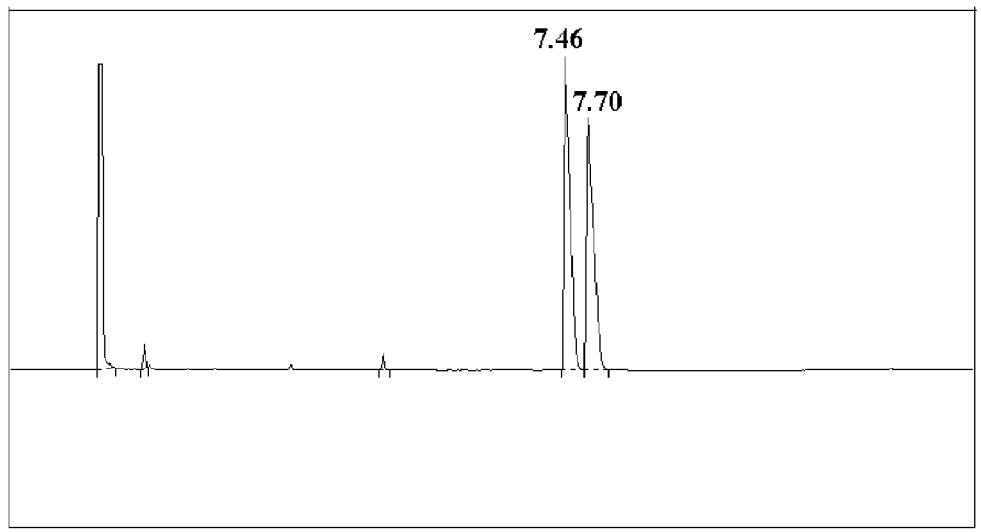
Figure 1A: Typical chromatogram for Compound 1
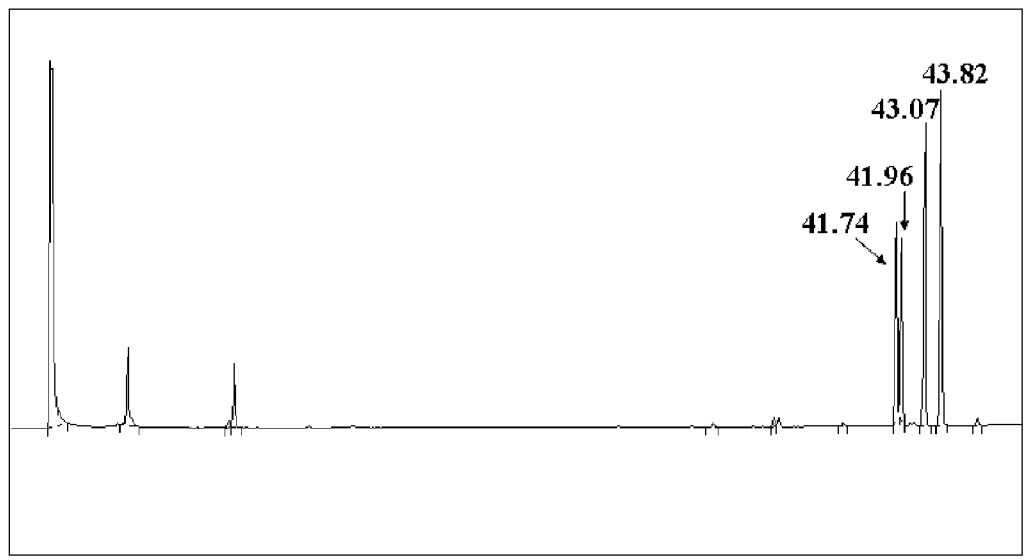
Figure 1B: Typical chromatogram for Compound 3

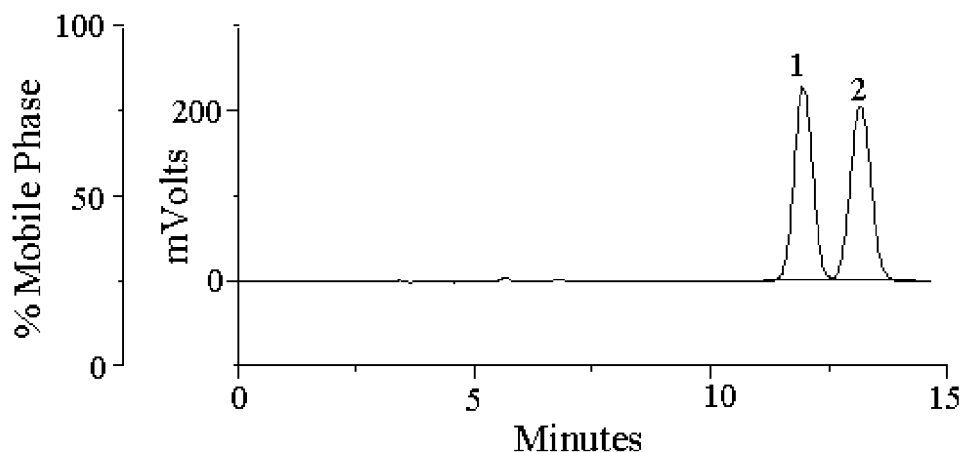
Figure 1C: HPLC method, Compound 11
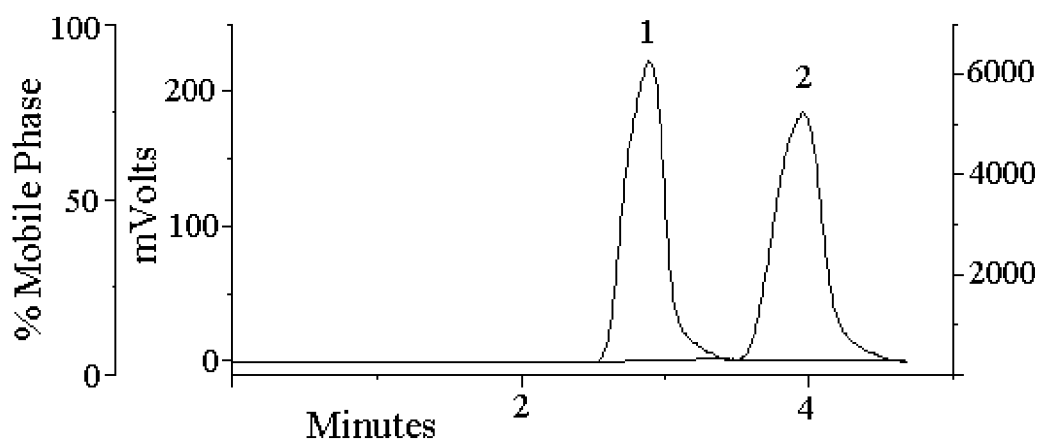
Figure 1D: SFC method, Compound 11

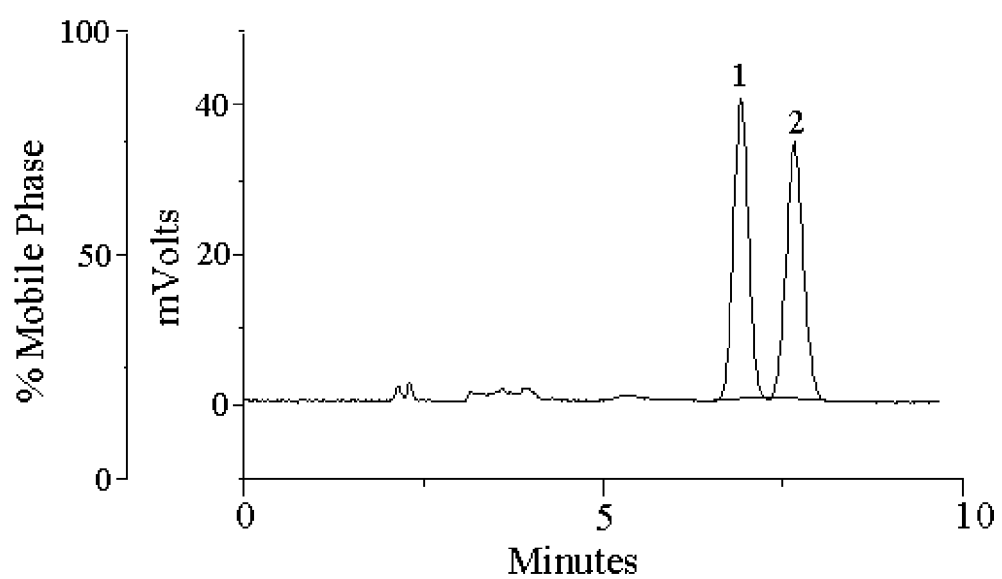
Figure 1E: HPLC method, Compound 12

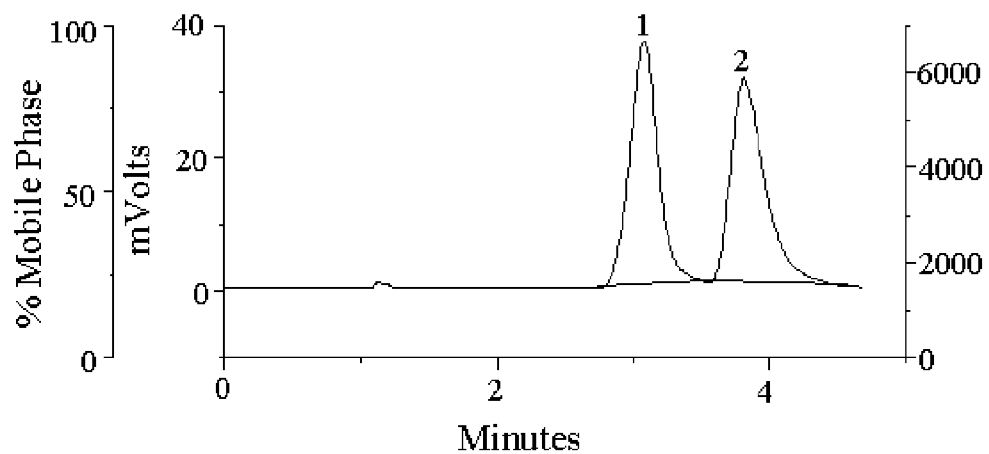
Figure 1F: SFC method, Compound 12
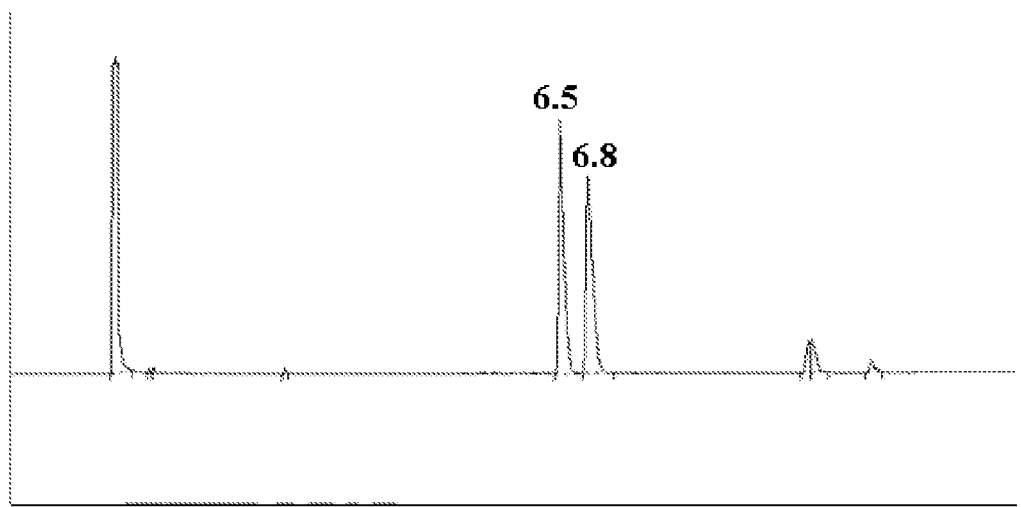
Figure 1G: Chiral GC method, Compound 13

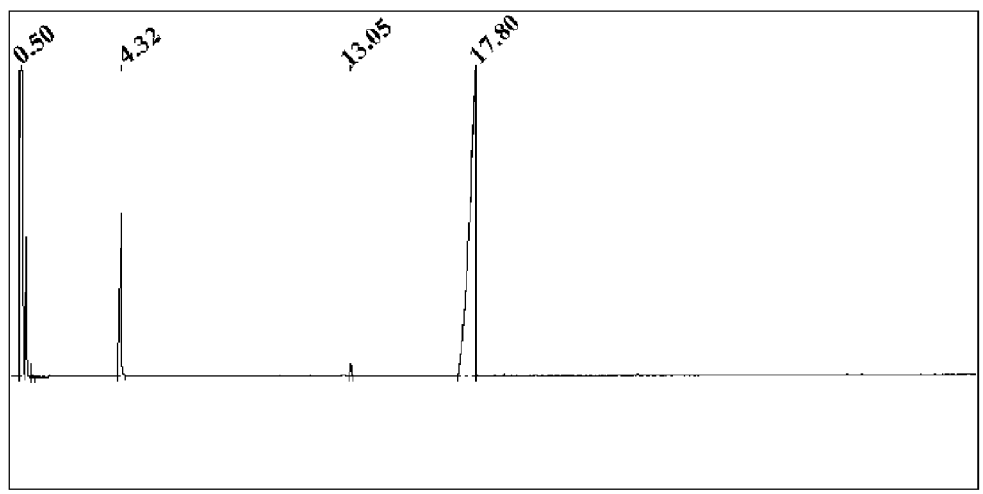
Figure 1H: GC purity method, Compound 13
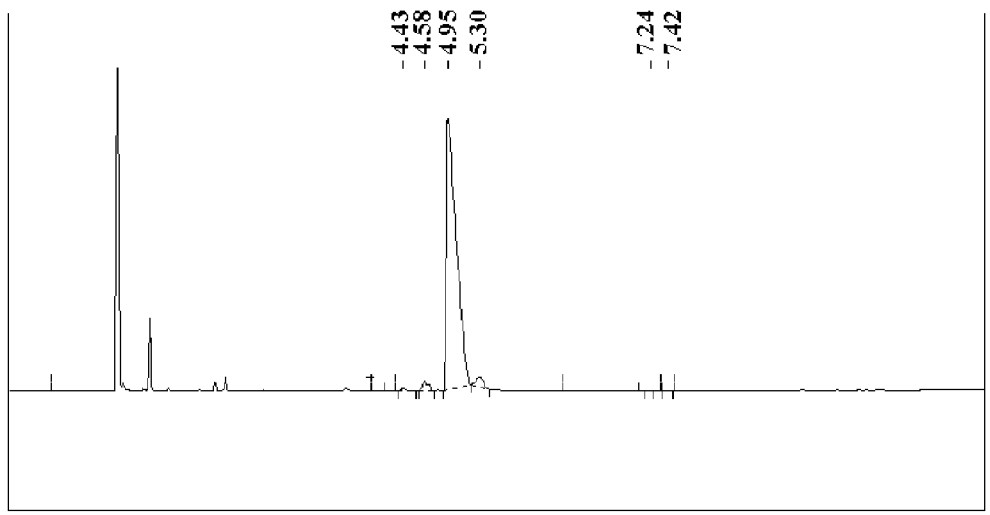
Figure 1I: Chiral GC Chromatogram, Compound 13

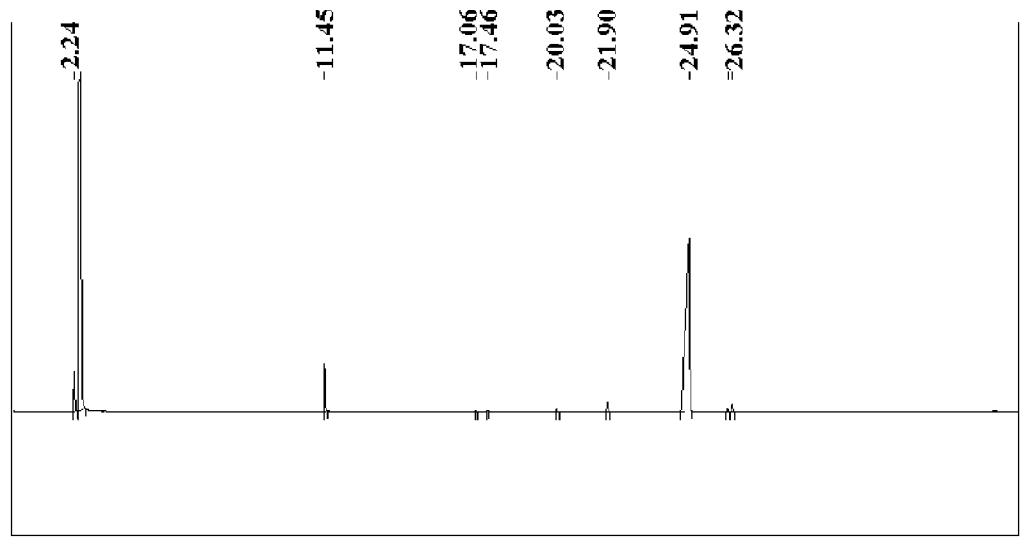
Figure 1J: Achiral GC Chromatogram, Compound 13
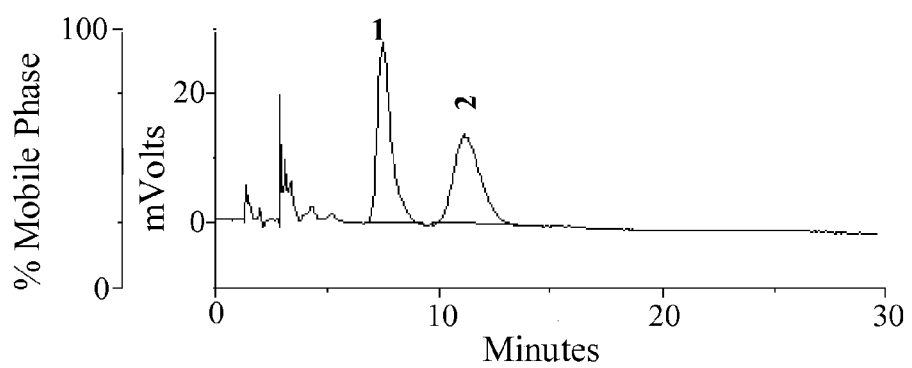
Figure 1K: Typical chromatogram for Compound 4

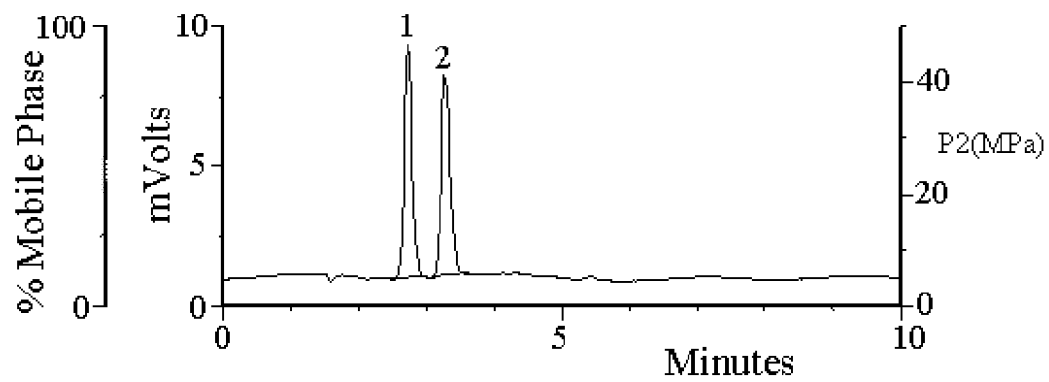
Figure 1L: Chromatogram of optimized assay for Compound 4
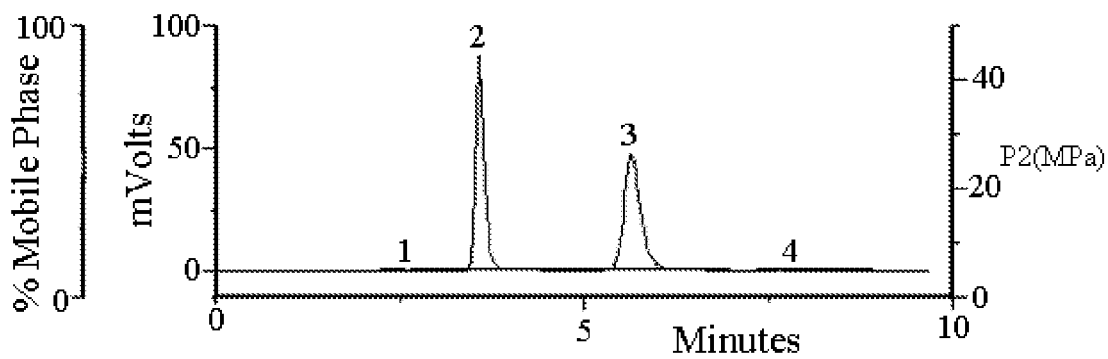
Figure 1M: Typical chromatogram for DAPD

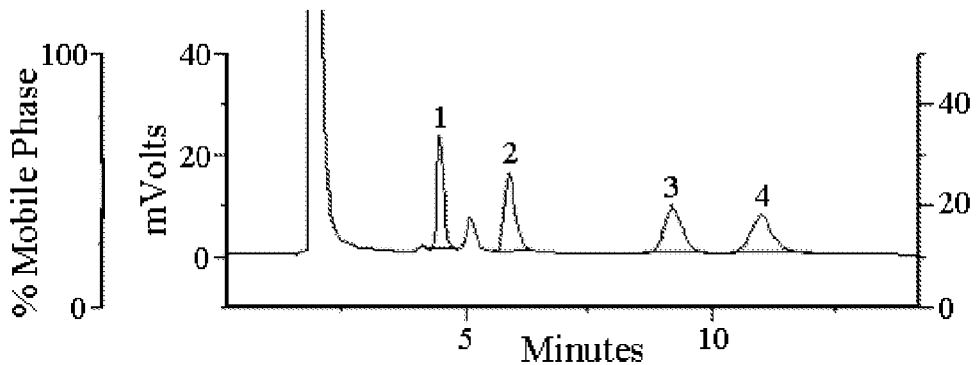
Peaks 1 and 3 - DAPD butyrate
Peaks 2 and 4 - DAPD
Figure 1N: Typical Chromatogram using SFC Conditions for DAPD and butyrate ester
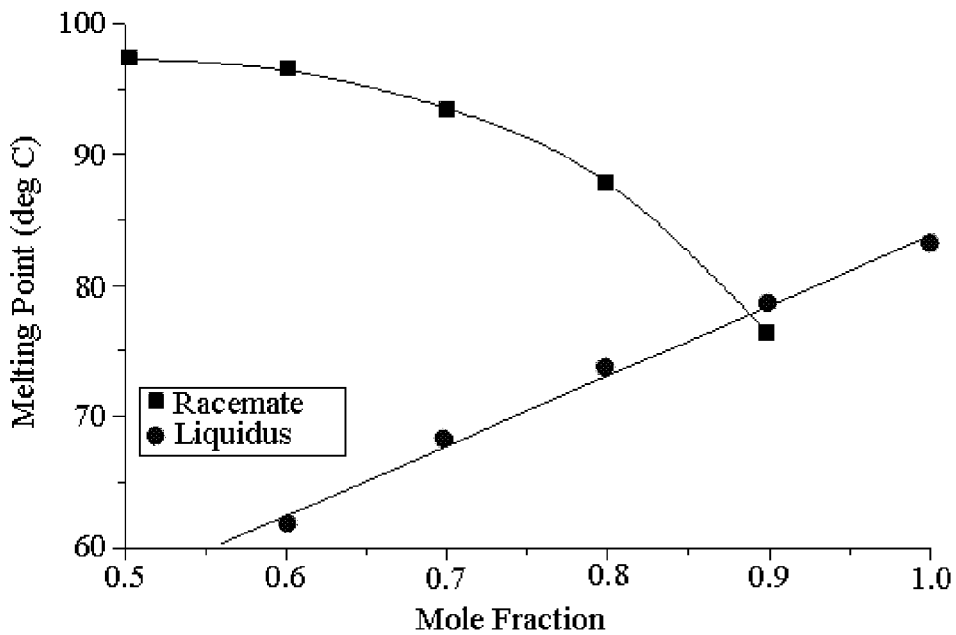
Figure 2: Theoretical phase diagram for Compound 4

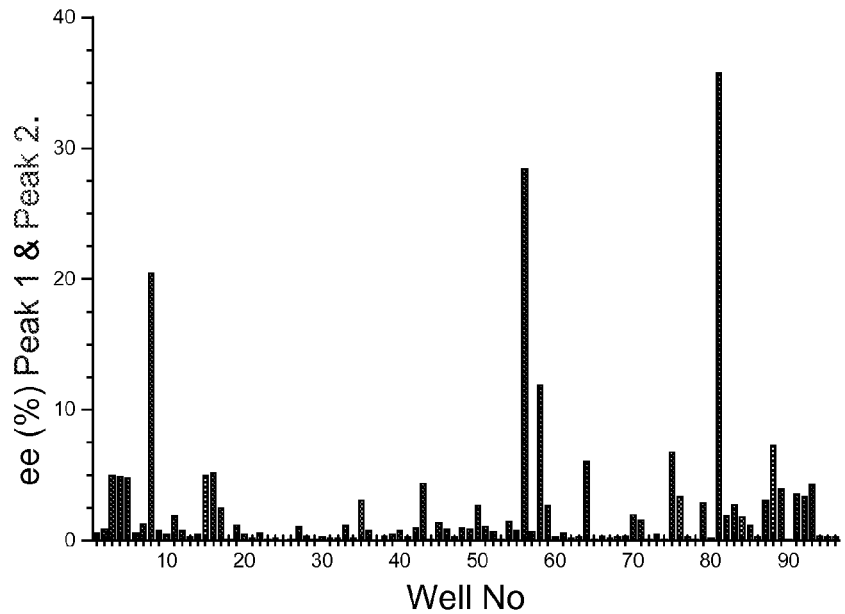
Figure 3A: Results from the screen of plate SCL0001 of Compound 1 (PK636/255)
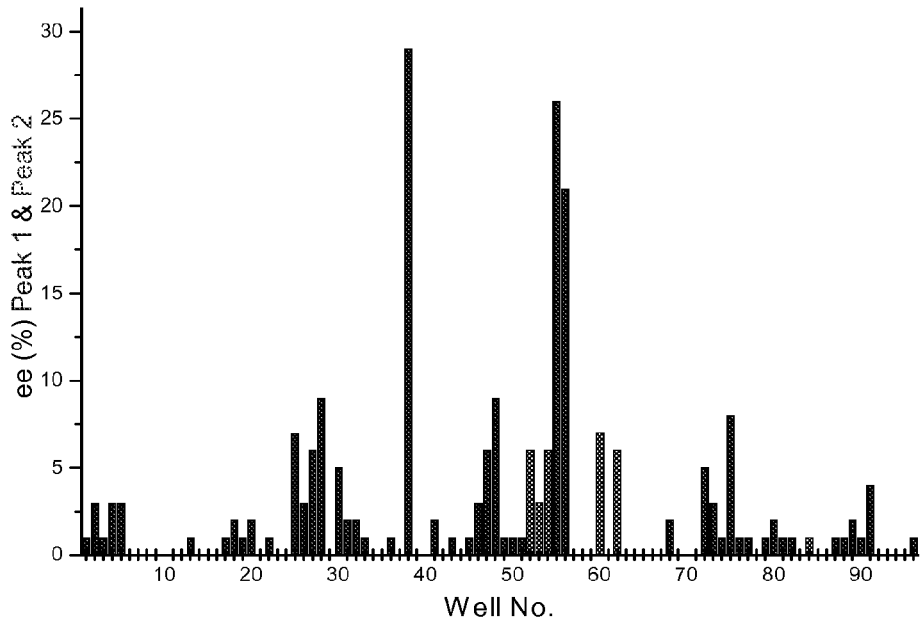
Figure 3B: Results from the screen of plate SCL0002 of Compound 1 (PK636/241)

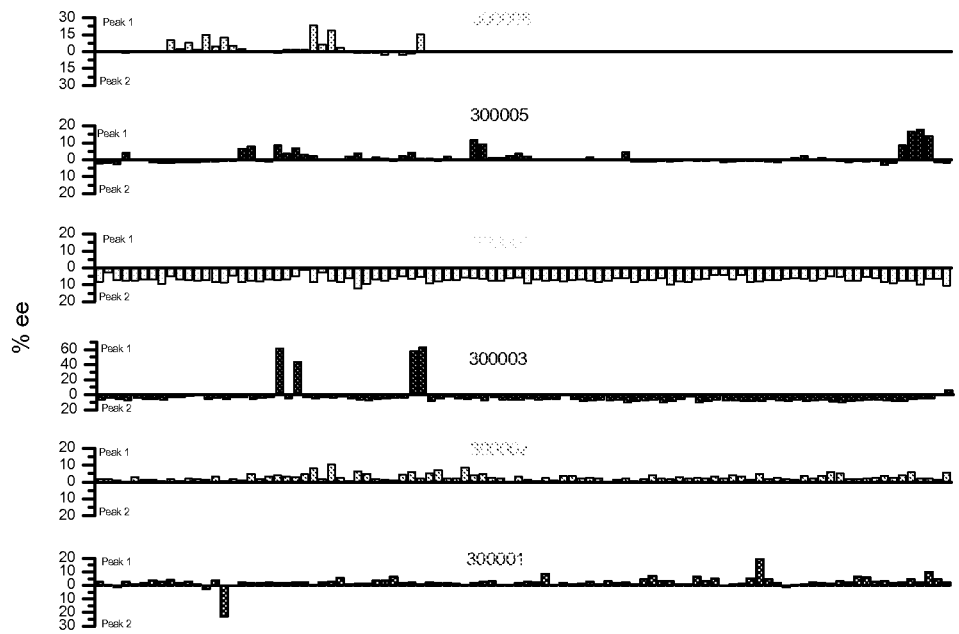
Figure 3C: Microbial screen of Compound 11
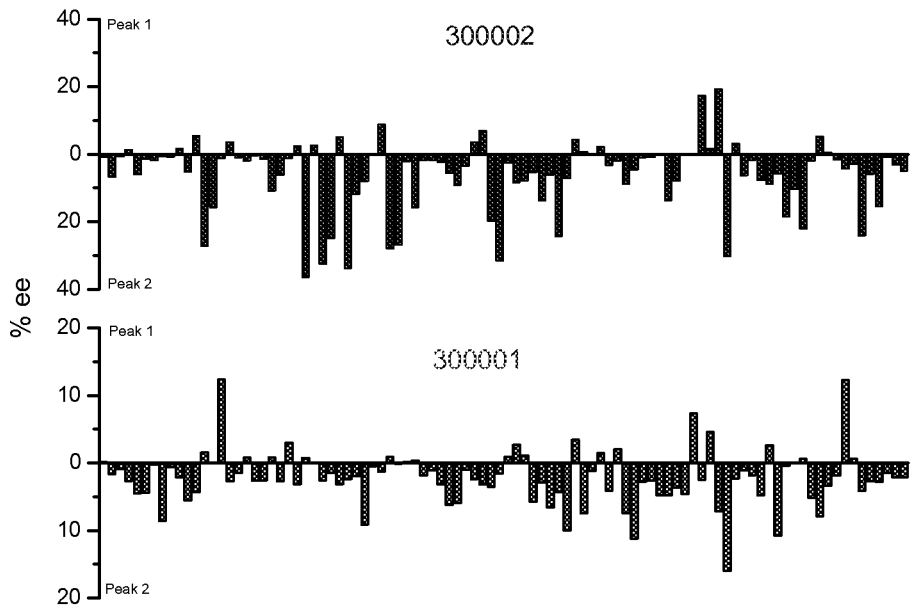
Figure 3D: Microbial Screen for Compound 12

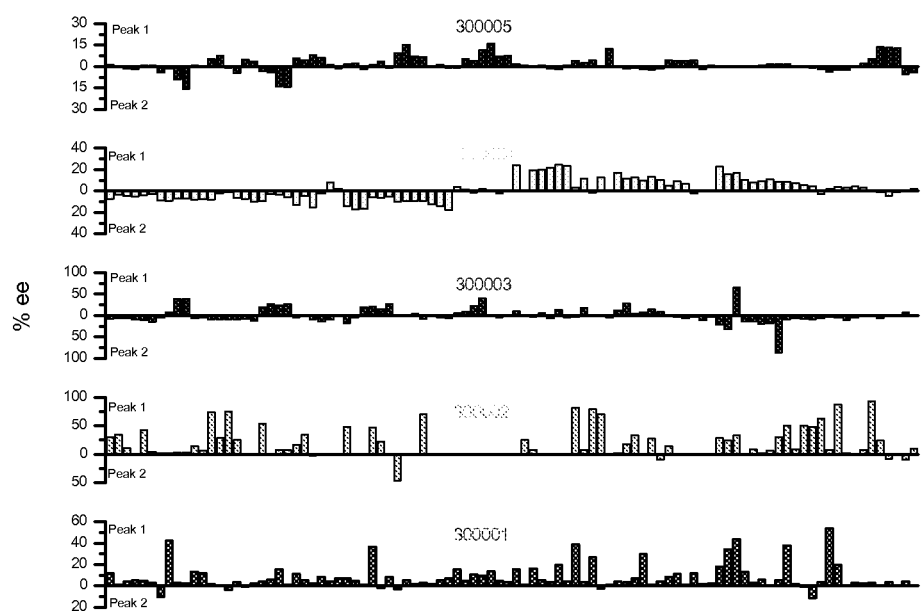
Figure 3E: Microbial Screen of Compound 13

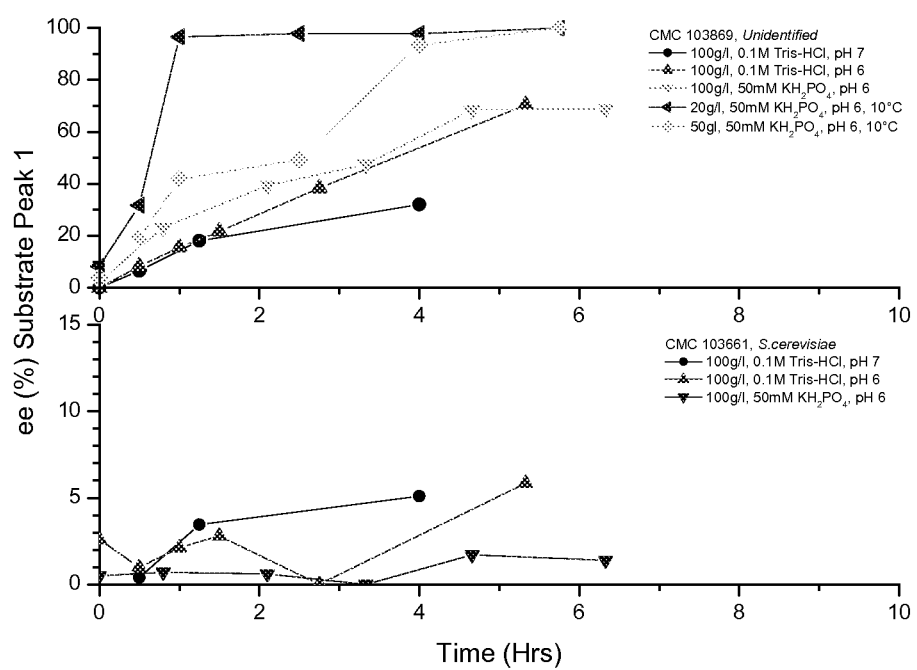
Figure 4: Microbial resolution of Compound 13

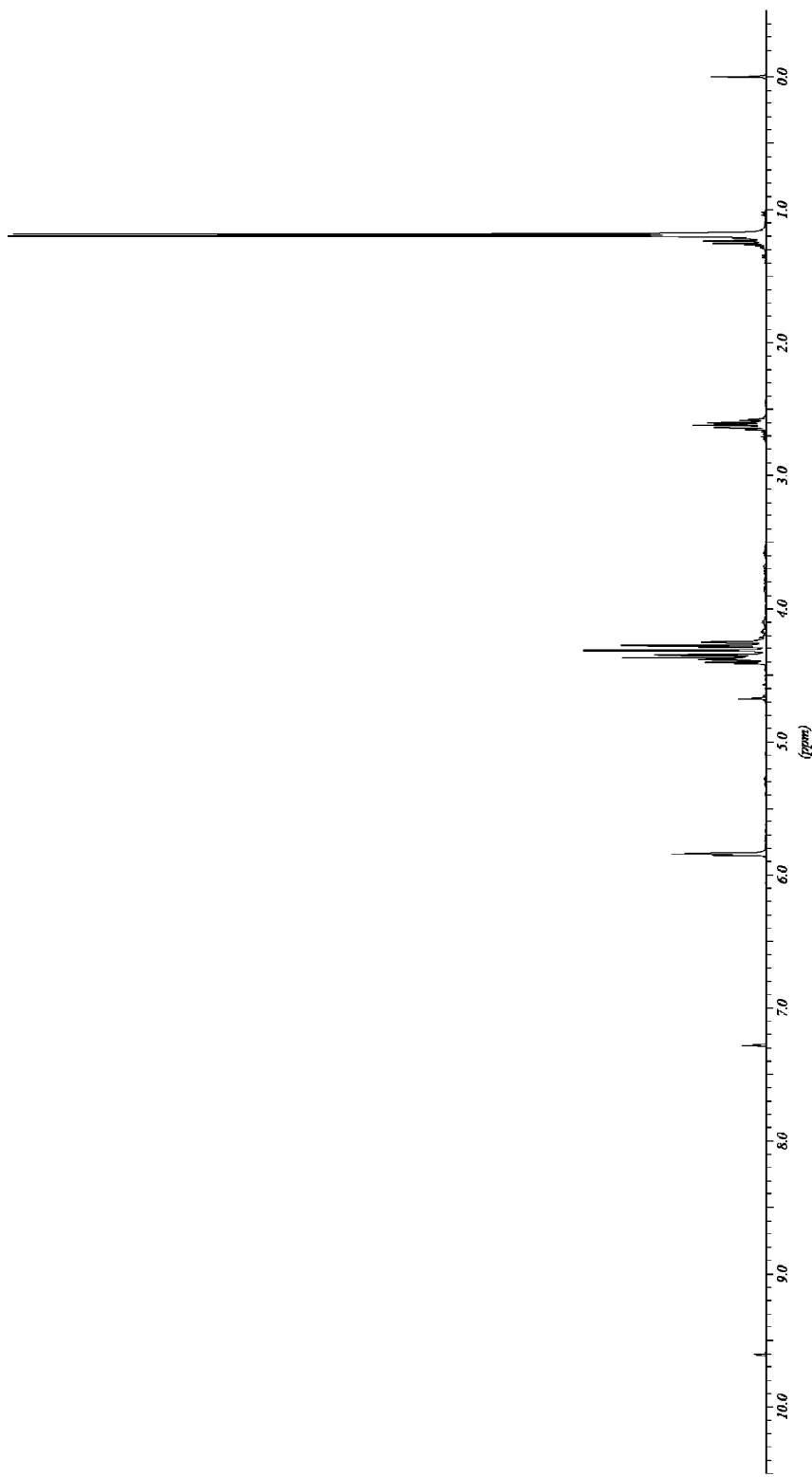
Figure 5: 400 MHz $^1$H NMR Spectrum for Resolved Compound 13

METHODS TO MANUFACTURE 1,3-DIOXOLANE NUCLEOSIDES

REFERENCE TO PRIOR APPLICATIONS

This application is a continuation of U.S. patent application Ser. No. 11/051,287, filed Feb. 3, 2005, now U.S. Pat. No. 7,785,839, which claims priority to U.S. Provisional Application No. 60/541,545, entitled "Methods To Manufacture 1,3-Dioxolane Nucleosides" filed Feb. 3, 2004.

FIELD OF INVENTION

This application provides a process for preparing enantiomerically pure β-D-dioxolane nucleosides. In particular, a new synthesis of (−)-DAPD, suitable for large scale development, is described.

BACKGROUND OF THE INVENTION

AIDS, Acquired Immune Deficiency Syndrome, is a catastrophic disease that has reached global proportions. Currently an estimated 40 million people worldwide are living with AIDS, with approximately 5 million new infections every year. The yearly death toll is still over 3 million people worldwide. Another virus that causes a serious human health problem is the hepatitis B virus (HBV). HBV is second only to tobacco as a cause of human cancer. Some estimates put the number of people worldwide that have been infected with HBV as high as two billion people, up to a third of the world's population, with approximately 400 million chronically infected.

A number of 2′,3′-dideoxynucleosides have been found to be potent antiviral agents against HIV and/or hepatitis B virus. After cellular phosphorylation to the 5′-triphosphate by cellular kinase, these synthetic nucleosides are incorporated into a growing strand of viral DNA, causing chain termination due to the absence of the 3′-hydroxyl group. They can also inhibit the viral enzyme reverse transcriptase.

There has also been interest in the synthesis of nucleoside derivatives in which the 3′-carbon of the nucleoside has been replaced with a heteroatom. Both 3TC and its 5-fluorocytosine analog (FTC) exhibit activity against HIV and HBV (Furman, et al., *Antimic. Ag. Chemo.*, 1992, 2686-2692; and Cheng, et al., *J. Biol. Chem.*, 1992, 267(20), 13938-13942).

The discovery that a racemic oxathiolane nucleoside BCH-189 possessed a potent activity against replication of HIV prompted Chu et al. to synthesize the chiral products (+)- and (−)-BCH-189 (Belleau, et al., 5th International Conference on AIDS, Montreal, Canada, Jun. 4-9, 1989, #T.C.O. 1; Chu, et al. *Tetr. Lett.*, 1991, 32, 3791). The latter compound, lamivudine, otherwise known as 3TC or epivir, is currently used clinically in the treatment of both HIV infection and HBV infection. The (−) enantiomer of 5-fluorocytosine oxathiolane analogue (FTC), is particularly active against HIV (Choi, W. et al., *J. Am. Chem. Soc.*, 1991, 113, 9377; Schinazi, R. F., et al., *Antimic. Ag. Chemo.* 1992, 2423; U.S. Pat. Nos. 5,204, 4665; 5,210,085; 5,914,331; and 5,639,814).

The above-described 1,3-oxathiolane nucleosides are manufactured by condensation of silylated purine or pyrimidine base with a 1,3-oxathiolane intermediate. U.S. Pat. No. 5,204,466 discloses a method to condense a 1,3-oxathiolane with a silylated pyrimidine using tin chloride as a Lewis acid, which provides virtually complete β-stereoselectivity. A number of U.S. patents describe processes for the preparation of 1,3-oxathiolane nucleosides via condensation of a 1,3-oxathiolane-2-carboxylic acid ester with a protected silylated base in the presence of a silicon-based Lewis acid, followed by reduction of the ester to the corresponding hydroxymethyl group to afford the final product (see U.S. Pat. Nos. 5,663, 320; 5,693,787; 5,696,254; 5,744,596; 5,756,706 and 5,864, 164). In addition, these patents contain generic disclosures for the synthesis of 1,3-dioxolane nucleosides in a similar fashion using the corresponding 1,3-dioxolane intermediate.

U.S. Pat. No. 5,272,151 discloses a process using a 2-O-protected-5-O-acylated-1,3-oxathiolane for the preparation of nucleosides by condensation with a silylated purine or pyrimidine base in the presence of a titanium catalyst. U.S. Pat. No. 6,215,004 discloses a process for producing 1,3-oxathiolane nucleosides that includes condensing 2-O-protected-methyl-5-chloro-1,3-oxathiolane with a silylated 5-fluorocytosine without a Lewis acid catalyst. In these cases, the 1,3-oxathiolane ring is prepared in one of the following ways: (i) reaction of an aldehyde derived from a glyoxylate or glycolic acid with mercaptoacetic acid in toluene in the presence of p-toluenesulfonic acid to give 5-oxo-1,3-oxathiolane-2-carboxylic acid; (ii) cyclization of anhydrous glyoxylates with 2-mercaptoacetaldehyde diethylacetal at reflux in toluene to give 5-ethoxy-1,3-oxathiolane lactone; (iii) condensation of glyoxylic acid ester with mercaptoacetaldehyde (dimeric form) to give 5-hydroxy-1,3-oxathiolane-2-carboxylic ester or (iv) coupling of an acyloxyacetaldehyde with 2,5-dihydroxy-1,4-dithiane, the dimeric form of 2-mercaptoacetaldehyde to form a 2-(ayloxy)methyl-5-hydroxy-1,3-oxathiolane. The lactone, 5-oxo compound, has to be reduced to the corresponding lactol during the process. The 2-carboxylic acid or its ester also has to be reduced to the corresponding 2-hydroxymethyl derivatives with borane-methylsulfide complex.

The key intermediate, aldehyde, can be prepared using several methods: (i) lead tetraacetate oxidation of 1,4-di-O-benzoyl meso-erythritol, 1,6-di-O-benzoyl D-mannitol or 1,5-di-O-benzoyl-D-arabitol; (ii) preparation of monoacylated ethylene glycol followed by oxidation to aldehyde; (iii) acylation of ethylene chlorohydrin followed by dimethylsulfoxide oxidation; (v) lead tetraacetate oxidation; (vi) ozonolysis of allyl or 3-methyl-2-buten-1-ol acylate; (vii) and more recently, by acylation of 2-butene-1,4-diol followed by ozonolysis. Also, U.S. Pat. No. 6,215,004 discloses a process to prepare acyloxyacetaldehyde diethylacetal by acylation of 2,2-diethoxyethanol.

Norbeck, D. W., et al. (*Tet. Lett.*, 1989, 30, 6263) reported the synthesis of (±)-1-(4β,4β)-2-(hydroxymethyl)-4-dioxolanyl-thymine, that results in a racemic mixture of diastereomers about the C4′ atom. The X-ray crystallographic analysis of the product revealed that the dioxolane ring adopts the $_3T_4$ conformation commonly observed in ribonucleosides, with the O3′ atom in the endo position, which is quite distinct from the distorted $_3E$ conformations observed in AZT, AZDU, ddA, ddC, and 3′-deoxy-3′-fluorothymidine, all of which exhibit potent in vitro activity against HIV.

The antiviral activity of dioxolane nucleosides prompted Chu et al. to synthesize a series of analogs in a search for potent antiviral and/or anticancer agents. For example, 9-(β-D hydroxymethyl-1,3-dioxolanyl)aminopurine (β-D-DAPD), and its metabolite 9-(β-D hydroxymethyl-1,3-dioxolanyl)-guanine (β-D-DXG) have been reported to have potent and selective activity against human immunodeficiency virus (HIV) and hepatitis B virus (HBV) (Rajagopalan et al., *Antiviral Chem. Chemother.*, 1996, 7(2), 65-70). (−)-DAPD is a potent and selective inhibitor of HIV in vitro and in vivo and HBV replication in vitro (Furman, et al. *Drugs of the Future* 2000, 25 (5), 454-461). Similarly, 1-(β-L hydroxymethyl-1,3-dioxolanyl)-thymine (Dioxolane-T)

(Norbeck et al., *Tet. Let.*, 1989, 30, 6263-66) possess anti-HIV and anti-HBV activity. 1-(β-L hydroxymethyl 3-dioxolanyl)-cytidine (β-L-OddC) was discovered to have potent anti-tumor activity towards human prostate as well as renal carcinoma (Kadhim et al., *Can. Cancer Res.*, 57(21), 4803-10, 1997). (−)-(2'S,4'R)-1'-[2'-(hydroxy-methyl)-1',3'-dioxolan-4'-yl]-5-iodouracil) L-IOddU is currently in pre-clinical or clinical studies to assess its value as an antiviral or anticancer agent (see Kim, et al., *J. Med. Chem.* 1993, 36, 519-528 and references therein; Corbett, & Rublein, *Curr. Opin. Investig. Drugs* 2001, 2, 348-353; Gu, et al., *Antimicrob. Agents Chemother.* 1999, 43, 2376-2382; Mewshaw, et al., *J. Acquir. Immune Defic. Syndr.* 2002, 29, 11-20).

U.S. Pat. No. 5,041,449 and U.S. Pat. No. 5,270,315 to Belleau et al. disclose a generic group of racemic 2-substituted-4-substituted-1,3-dioxolanes. Table 1 of the reference shows data for two racemic 1,3-dioxolane nucleosides—a racemic trans (α) 1,3-dioxolane nucleoside with a cytosine base (Compound XII) and a racemic cis (β) 1,3-dioxolane nucleoside with an adenine base (Compound XIV) (see also EP 0 337 713 to IAF BioChem International).

In June 1989, Belleau, et al., reported a method of synthesis of cytidine nucleosides that contain oxygen or sulfur in the 3'-position (Belleau, B., et al. Fifth International Conference on AIDS, Montreal; International Development Research Centre: Ottawa, Ontario, 1989; T.C.O.1.). The dioxolane ring was prepared by the condensation of $RCO_2CH_2CHO$ with glycerin. The synthesis resulted in a racemic mixture of diastereoisomers about the C4' carbon of the nucleoside. Racemic DAPD was synthesized as depicted in Scheme 1.

Scheme 1

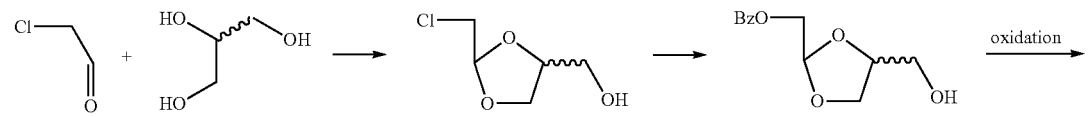

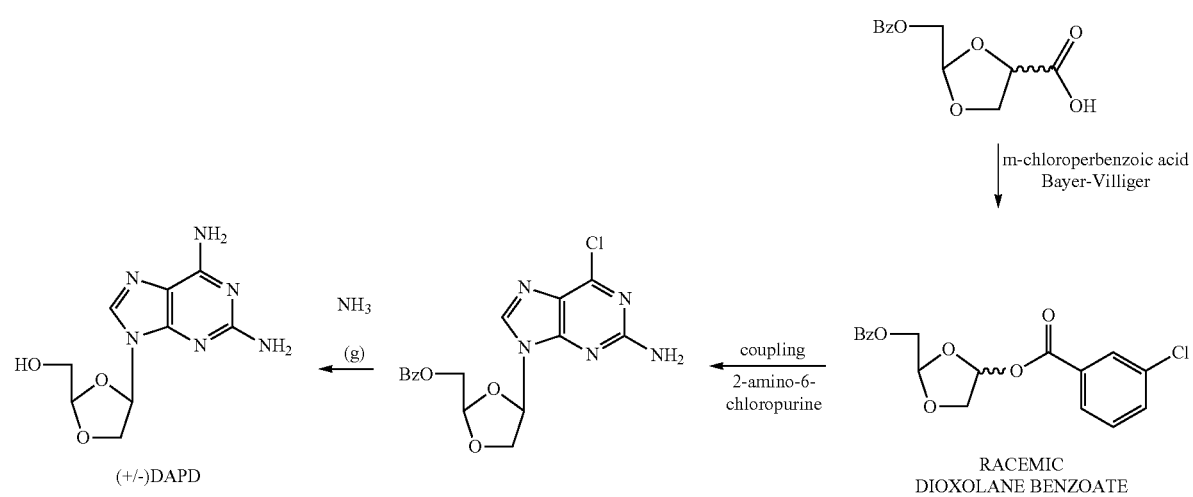

(+/−)DAPD

RACEMIC DIOXOLANE BENZOATE

Belleau et al. reacted glycerol and chloroacetaldehyde to generate a dioxolane intermediate. After chlorine displacement with a benzoic acid salt, oxidation of the primary alcohol to a carboxylic acid and Baeyer-Villiger rearrangement with m-chloroperbenzoic acid, the corresponding racemic dioxolane benzoate was obtained. This compound was then coupled with 2-amino-6-chloropurine and the resulting nucleoside intermediate was reacted with ammonia under pressure to afford racemic DAPD. (±)-Dioxolane-T was also synthesized in similar fashion by Choi et al. (Choi, et al., *J. Am. Chem. Soc.* 1991, 113, 9377-9378 and U.S. Pat. No. 5,852,027).

As discussed above, in late 1989, Norbeck et al. published an article which described the synthesis of racemic cis-1,3-dioxolane thymidine which also had anti-HIV activity in vitro (Norbeck, et al. *Tet. Let.* 1989, 30 (46), 6263-6266). The product was synthesized in five steps from benzyloxyaldehyde dimethylacetal and (±)-methyl glycerate to produce a 79% yield of the 1:1 diastereomeric mixture. As with the Belleau synthesis, the Norbeck synthesis results in a racemic mixture of diastereoisomers about the C4' carbon of the nucleoside. See Scheme 2.

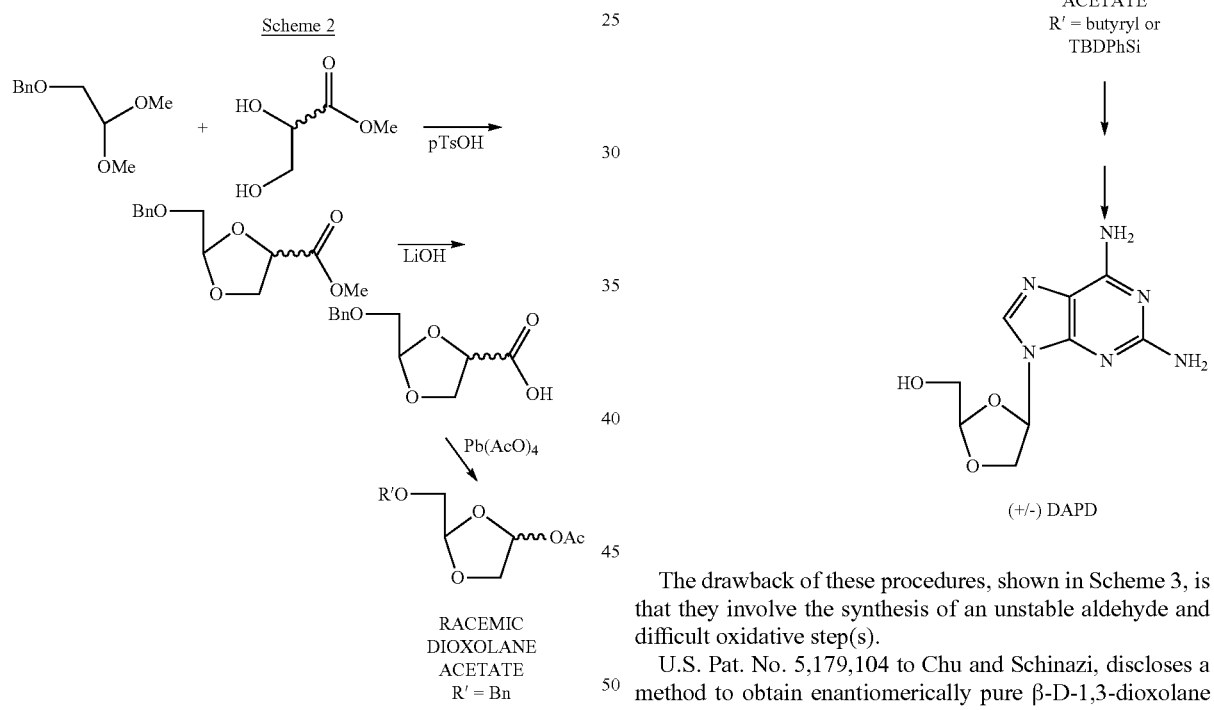

The same racemic dioxolane acetate intermediate was synthesized by Liotta et. al. starting from cis-2-buten-1,4-diol (Choi, et al. *J. Am. Chem. Soc.* 1991, 113 (24), 9377-0379 and Wilson, et al. *Bioorg. Med. Chem. Let.* 1993, 3 (2), 169-174). See Scheme 3.

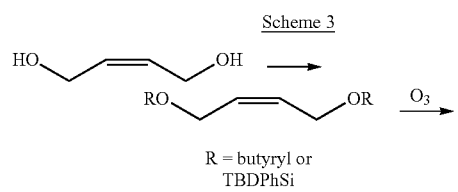

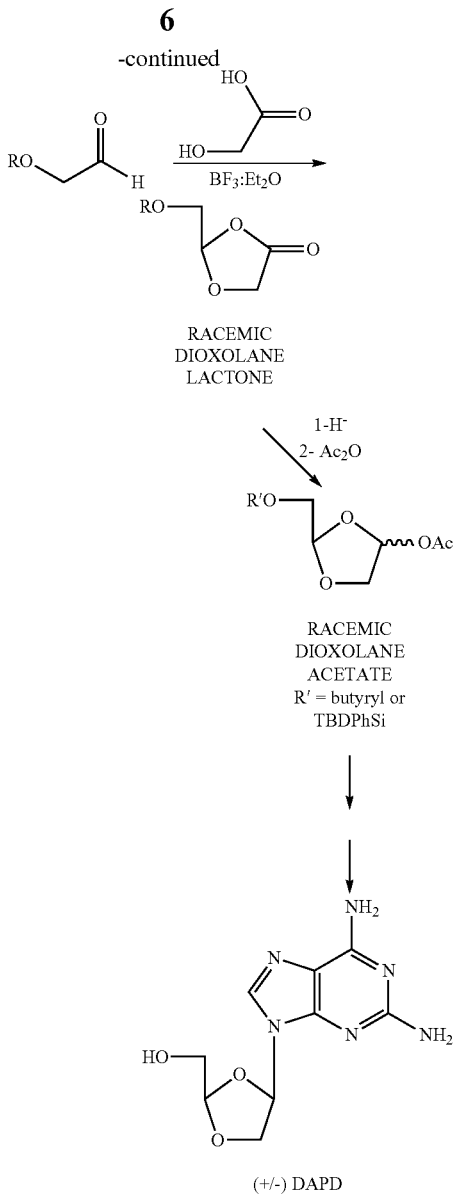

The drawback of these procedures, shown in Scheme 3, is that they involve the synthesis of an unstable aldehyde and difficult oxidative step(s).

U.S. Pat. No. 5,179,104 to Chu and Schinazi, discloses a method to obtain enantiomerically pure β-D-1,3-dioxolane nucleosides via a stereospecific synthesis (see also related U.S. Pat. Nos. 5,925,643; 5,767,122; 5,444,063; 5,684,010; 5,834,474; and 5,830,898).

EP 0 515 156 to BioChem Pharma discloses a method to obtain the enantiomers of 1,3-dioxolane nucleosides using a stereoselective synthesis that includes condensing a 1,3-dioxolane intermediate covalently bound to a chiral auxiliary with a silyl Lewis acid (see also related U.S. Pat. Nos. 5,753, 706 and 5,744,596).

Chu, et al., published a stereospecific synthesis of β-D-1, 3-dioxolane nucleosides from 1,6-anhydromannose (Chu, et al. *Tet. Let.*, 1991, 32, 3791-3794). At about the same time, Thomas and Surber published an article which described that (i) a thorough search of the literature on chiral chromatography failed to reveal any examples of nucleoside separations and that (ii) their paper appears to be the first separation of the enantiomers of a nucleoside by chiral high performance liquid chromatography. The nucleoside resolved was not a 1,3-dioxolane nucleoside, and four out of the five chiral columns attempted did not work (Thomas, et al., *J Chromat.*, 1991, 586, 265-270).

Kim et al. (Kim, et al. *J. Med. Chem.* 1993, 36 (1), 30-37) subsequently published a paper which discloses an asymmetric synthesis of β-D and α-D enantiomers of 1,3-dioxolane pyrimidine nucleosides from 1,6-anhydro-D-mannose. The synthesis of (−)-DAPD was described as a thirteen step process from 1,6-anhydro-D-mannose including a nine step conversion of 1,6-anhydro-D-mannose to a chiral acetate (Scheme 4).

oxaribosides with silylated N-acetylcytosine. The use of the Lewis acids trimethylsilyltriflate, trimethylsilyl iodide, and $TiCl_2(Oi-Pr)_2$ furnishes enantiomerically pure cytosine dioxolane nucleosides in low diastereoselectivity.

An asymmetric synthesis of dioxolane nucleosides was reported by Evans, et al. (*Tet. Asym.* 1993, 4, 2319-2322). Reaction of D-mannitol with $BnOCH_2CH$—$(OCH_3)_2$ in the presence of $SnCl_2$ in 1,2-dimethoxyethane followed by $RuCl_3/NaOCl$ oxidation gave cis- and trans-dioxolane-4-carboxylic acid, which was then converted to D- and L-dioxolane nucleosides by decarboxylation, coupling and deprotection reactions. An alternative route to these carboxylic acids by reaction of $BnOCH_2CH(OCH_3)_2$ with L-ascorbic

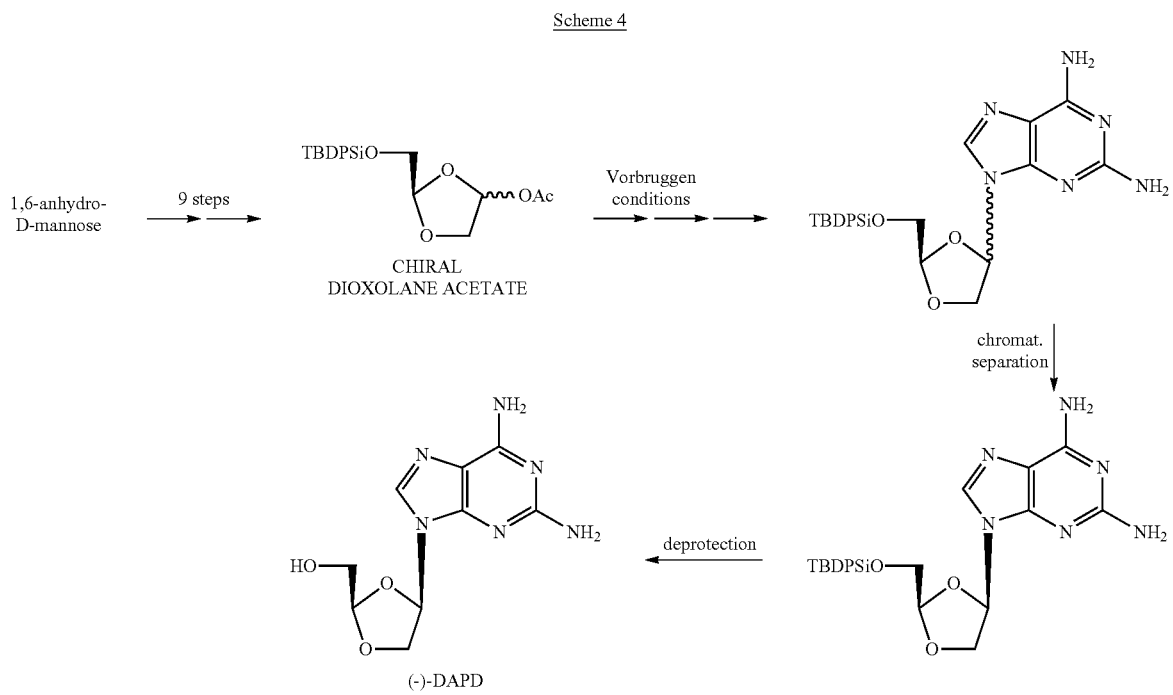

Scheme 4

After coupling of the acetate under Vorbruggen conditions and several purification and deprotection steps, (−)-DAPD was obtained in modest yield. This process is time consuming, difficult and involves complicated oxidation steps.

In 1992, Belleau et al. (Belleau, et al. *Tet. Let.* 1992, 33, 6949-6952) published a synthesis of enantiomerically pure 2',3'-dideoxy-3-oxacytidine stereoisomers via an eight step process using L-ascorbic acid as a chiral auxiliary. L-ascorbic acid was used to produce a set of diastereomers which could be separated. The use of lead tetraacetate makes this process unsuitable for scale-up. In 1992, Kim, et al., also published an article disclosing how to obtain (−)-L-β-dioxolane-C and (+)-L-β-dioxolane-T from 1,6-anhydro-L-β-gulopyranose (Kim, et al., *Tet. Let.* 1992, 32(46), 5899-6902).

Liotta and Shinazi, in U.S. Pat. No. 5,276,151, found that racemic 2-O-protected-5-O-acylated-1,3-dioxolanes could be coupled with purine or pyrimidine bases in the presence of a titanium-containing Lewis acid to predominately generate the racemic (3-isomers (see also WO 92/14729).

Jin et al. (Jin, et al. *Tet. Asym.* 1993, 4 (2), 211-214), discloses that Lewis acid catalysts play a crucial role in the preparation 1,3-dioxolane nucleosides. $TiCl_4$ and $SnCl_4$ promote the formation of dioxolane nucleosides with racemization in the coupling of enantiomerically pure 2'-deoxy-3'- acid was also reported in the paper. The chiral carboxylic acid can also be prepared by reacting commercially available 2,2-dimethyl-1,3-dioxolane-4-(S)-carboxylic acid with a protected derivative of hydroxy-acetaldehyde such as benzoyloxyacetaldehyde, under acidic conditions (see U.S. Pat. Nos. 5,922,867 and 6,358,963).

Siddiqui, et al., discloses that cis-2,6-diaminopurine dioxolane can be selectively deaminated using adenosine deaminase (Siddiqui, et al., *Bioorg. Med. Chem. Let.*, 1993, 3 (8), 1543-1546).

While the synthesis of dioxolane nucleosides is possible using processes described in the literature, the chemistry is not applicable to the synthesis of (−)-DAPD on large scale. See Chu, et al. *Tet. Let.* 1991, 32, 3791-3794; Siddiqui, et al. *Bioorg. Med. Chem. Let.* 1993, 3, 1543-1546; Kim, et al. *Tet. Let.* 1992, 46, 6899-6902).

U.S. Pat. No. 5,763,606 to Mansour et al. describes processes for producing predominately pure 1,3-oxathiolane and 1,3-dioxolane nucleosides via coupling of a silylated purine or pyrimidine base with a bicyclic intermediate (see also WO 94/29301).

U.S. Pat. No. 6,215,004 to Painter et al. discloses process for preparing 2-[$R^1C(O)OCH_2$]-1,3-dioxolanyl-5-one by reacting glycolic acid with an acetal of the formula $(R^1O)_2$ CHR; a hemiacetal of the formula (R²O)(HO)CHR; or a mixture thereof, wherein R is —(CH₂—O—C(O)R¹), and R¹ and R² are independently alkyl, aryl, heteroaryl, heterocyclic, alkaryl, alkylheteroaryl, or alkylheterocyclic, or aralkyl, in the presence of a Lewis acid, such as boron trifluoride diethyl etherate (see also WO 00/09494).

WO 00/47759 and WO 01/58894 both to BioChem Pharma disclose processes of separating β and α anomers from an anomeric mixture of dioxolane analogs with a COOR moiety at the C4' position prior to coupling with a purine or pyrimidine base. The process for resolving the dioxolane analogues to obtain dioxolanes having a predominant β-L-configuration, involves the use of enzymes, namely hydrolases.

WO 03/062229 to Shire BioChem. Inc. discloses a single reaction vessel process for producing a dioxolane nucleoside analogue by adding a Lewis acid, a silylating agent and a non-silylated purine or pyrimidine base to a dioxolane. The publication also describes a process for producing a dioxolane compound by reacting a dioxolane compound in a solvent in the presence of DIB and I2, using a suitable source of energy.

The stereochemistry of 3'-oxa-substituted 2',3'-dideoxynucleoside analogues ("dioxolane nucleoside analogues") can play an important role in their biological activity. The Cr position of the ribose in the nucleoside is a chiral center because the carbon is attached to four different moieties. Likewise, there is an optically active center at C4' of the nucleoside.

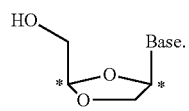

As shown below, the substituents on the chiral carbons (the specified purine or pyrimidine base and CH₂OH) of 1,3-dioxolane nucleosides can be either cis (on the same side) or trans (on opposite sides) with respect to the dioxolane ring system. For the purpose of consistency, the same stereochemical designation is used when the methyloxy moiety or the base moiety is replaced with another substituent group. Both the cis and trans racemates consist of a pair of optical isomers. Hence, each compound has four individual optical isomers. The four optical isomers are represented by the following configurations (when orienting the dioxolane moiety in a horizontal plane such that the —O—CH₂— moiety is in front): (1) cis, with both groups "up", which is a β-cis configuration (referred to as β-D); (2) cis, with both groups "down", which is the opposite β-cis configuration (referred to as β-L); (3) trans with the C4' substituent "up" and the Cr substituent "down"; and (4) trans with the C4' substituent "down" and the Cr substituent "up". The two cis enantiomers together are referred to as a racemic mixture of β-enantiomers, and the two trans enantiomers are referred to as a racemic mixture of α-enantiomers. In general, it is difficult to separate or otherwise obtain the individual enantiomers of the cis-configuration. The four possible stereoisomers of cis-1,3-dioxolane nucleosides are illustrated below:

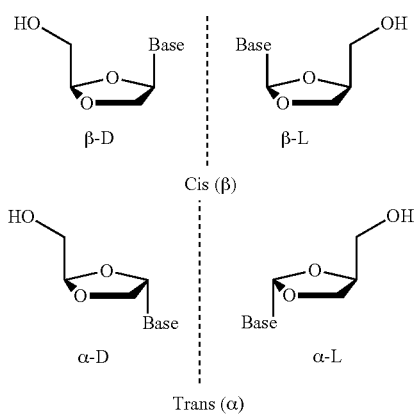

Since stereoisomers of dioxolane nucleosides usually have different biological activities and toxicity, obtaining the pure therapeutically active isomer becomes crucial. Frequently, one stereoisomer is considerably more active than the other.

Chu et al. developed methods for the asymmetric synthesis of dioxolane nucleosides from D-mannose and L-gulonic lactone for D- and L-dioxolane nucleosides, respectively (U.S. Pat. Nos. 5,767,122, 5,792,773). However, these processes involved many steps and most of the intermediates need to be purified by silica gel column chromatography (see Kim et al. *J. Med. Chem.* 1993, 36, 519-528).

To prepare a sufficiently large quantity of dioxolane nucleoside drug substance for clinic trials, a chiral 2-acyloxymethyl-5-oxo-1,3-dioxolane has been used as the key intermediate. This was prepared by cyclization of ROCH₂CHO or its acetal with glycolic acid in the presence of BF₃, followed by column separation on chiral resin or by enzymatic resolution, which are expensive and difficult techniques.

Thus, there remains a need for cost-effective and stereoselective processes to produce biologically active isomers of dioxolane nucleosides.

It is an object of the present invention to provide novel and cost-effective processes for the synthesis of enantiomerically pure dioxolane nucleosides.

SUMMARY OF THE INVENTION

The present invention includes an efficient synthetic route to 1,3-dioxolane nucleosides from inexpensive precursors, with the option of introducing functionality as needed. The processes allow the stereoselective preparation of the biologically active isomer of these compounds.

In one embodiment of the present invention, a process for preparing a substantially pure β-D- or β-L-1,3-dioxolane nucleoside, such as β-D-DAPD, is provided, comprising:

a) preparing or obtaining an esterified 2,2-dialkoxy ethanol of the formula (Ia) or (Ib);

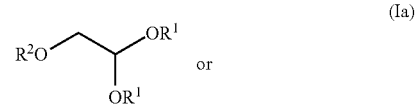

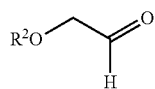
(Ib)

wherein:
each $R^1$ is independently alkyl, aryl, heteroaryl, heterocyclic, alkaryl, alkylheteroaryl, or alkylheterocyclic, or aralkyl; and $R^2$ is any suitable removable group such that (1) it is easily removable at the end of the synthesis, (2) it has a low molecular weight to avoid carrying large mass during the process, (3) it is commercially available and inexpensive, (4) the corresponding ester is stable under the reductive acetylation conditions, (5) the subsequent lactone is resolvable, and (6) after coupling, the corresponding anomers are easily separated, preferentially by crystallization (e.g. iso-butyryl or p-methoxy benzoyl);

and then, b) cyclizing the esterified 2,2-dialkoxy ethanol of the formula (Ia) or (Ib) with glycolic acid, preferably in the presence of a Lewis acid, such as $BF_3.Et_2O$, to obtain a 1,3-dioxolane lactone of the formula (II):

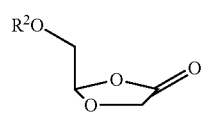
(II)

and then, c) resolving the 1,3-dioxolane lactone of the formula (II) to obtain a substantially pure D- or L-lactone; and then, d) selectively reducing with a reducing agent, such as $LiAlH(OtBu)_3$ and activating the substantially pure D- or L-chiral lactone to obtain a substantially pure D- or L-1,3-dioxolane of the formula (III):

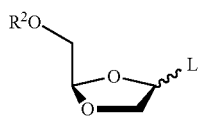
(III)

wherein:
L is a suitable leaving group, such as an O-acyl, such as OAc, halogen (F, Br, Cl or I), OMesylates (OMs) and OToluates (OTs), or the like;

and then, e) coupling the substantially pure D- or L-1,3-dioxolane of the formula (III) to an activated and/or protected purine or pyrimidine base or its derivative, such as activated 2,6-dichloropurine, to obtain α:β mixture of substantially pure protected D- or L-1,3-dioxolane nucleosides of the formula (IV):

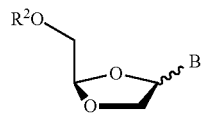
(IV)

wherein:
B is a purine or pyrimidine base or its derivative;

and then, f) purifying the α:β mixture of substantially pure protected D- or L-1,3-dioxolane nucleosides of the formula (IV) to obtain a substantially pure protected β-D- or β-L-1,3-dioxolane nucleoside; and then g) deprotecting the substantially pure protected β-D- or β-L-1,3-dioxolane nucleoside, if necessary, to obtain a substantially pure β-D- or β-L-1,3-dioxolane nucleoside.

In one embodiment of the present invention, the esterified 2,2-dialkoxy ethanol of the formula (Ia) is hydrolyzed to the corresponding aldehyde of formula (Ib). In a particular embodiment the esterified 2,2-dialkoxy ethanol of the formula (Ia) is hydrolyzed to the corresponding aldehyde of formula (Ib) when $R^2$ is p-methoxy benzoyl.

In another embodiment of the present invention, the esterified 2,2-dialkoxy ethanol of the formula (Ia) is not hydrolyzed to the corresponding aldehyde of formula (Ib). In a particular embodiment the esterified 2,2-dialkoxy ethanol of the formula (Ia) is not hydrolyzed to the corresponding aldehyde of formula (Ib) when $R^2$ is iso-butyryl.

In one embodiment of the present invention, the resolution of the 1,3-dioxolane lactone of the formula (II) to obtain a substantially pure D- or L-lactone is accomplished using chiral chromatography. In an alternate embodiment of the present invention, the resolution of the 1,3-dioxolane lactone of the formula (II) to obtain a substantially pure D- or L-lactone is accomplished using enzymatic resolution.

Scheme 5

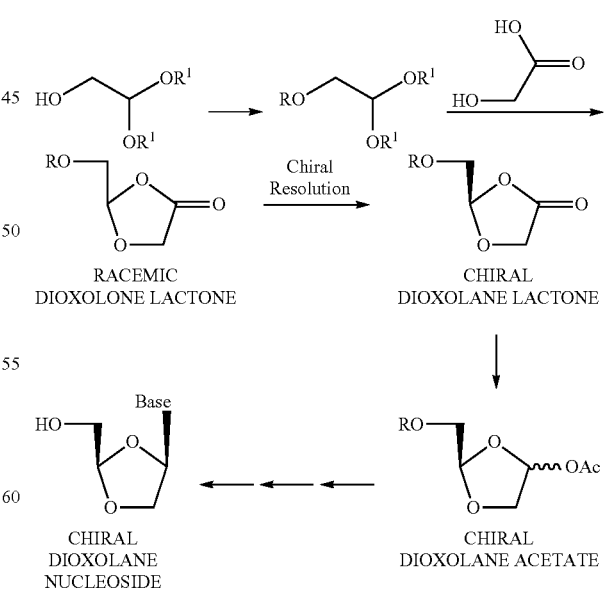

Therefore, the processes of the present invention may be used to prepare compounds of formula A to D:

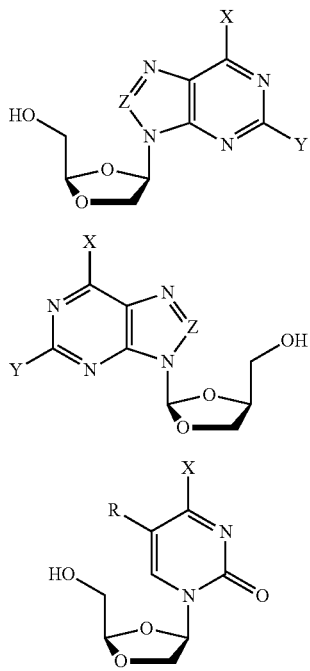

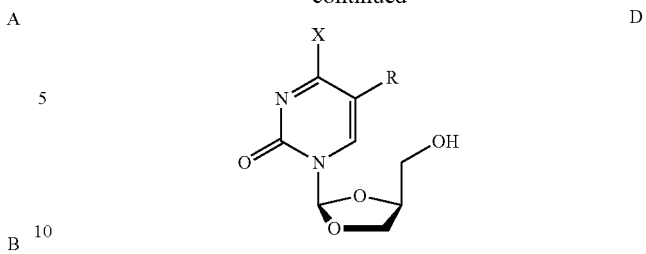

and pharmaceutically acceptable salts or esters thereof, wherein:

R is independently H, halogen (F, Cl, Br, I), OH, OR', OCH$_3$, SH, SR', SCH$_3$, NH$_2$, NHR', NR'$_2$, lower alkyl of C$_1$-C$_4$, CH$_3$, CH=CH$_2$, N$_3$C=CH$_2$, CO$_2$H, CO$_2$R', CONH$_2$, CONHR', CH$_2$OH, CH$_2$CH$_2$OH, CF$_3$, CH$_2$CH$_2$F, CH=CHCO$_2$H, CH=CHCO$_2$R', CH=CHCl, CH=CHBr, or CH=CHI;

each R' is independently a lower alkyl of C$_1$-C$_4$;

Z is either one of CH or C—X; and each X and Y are independently H, halogen (F, Cl, Br, I), OH, OR', OCH$_3$, SH, SR', SCH$_3$, NH$_2$, NHR', NR'$_2$, or CH$_3$.

In a particular embodiment of the present invention, a process for preparing substantially pure β-D-DAPD, is provided. See Scheme 6.

Scheme 6

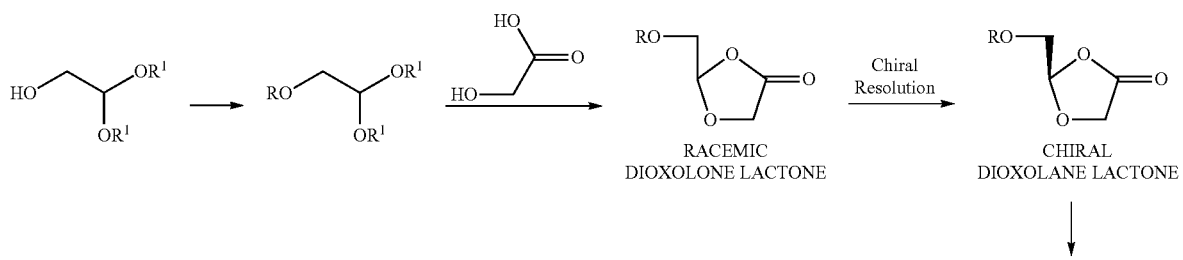

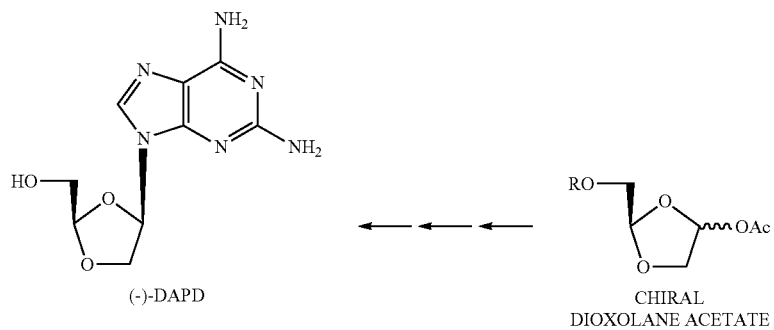

BRIEF DESCRIPTION OF THE FIGURES

FIG. 1 are typical chromatograms for the compounds of the present invention.

FIG. 1A is a typical chromatogram for the butyrl ester lactone (compound 1). FIG. 1B is a typical chromatogram for the butyrl ester acetate (compound 3). FIG. 1C is a typical chromatogram for the p-methoxybenzoyl lactone (compound 11). FIG. 1D is a typical chromatogram for the p-methoxybenzoyl lactone (compound 11) using the optimized SFC method. FIG. 1E is a typical chromatogram for the benzoyl lactone (compound 12). FIG. 1F is a typical chromatogram for the benzoyl lactone (compound 12) using the optimized SFC method. FIGS. 1G-1J are typical chromatogram for the iso-butyrl ester lactone (compound 13). FIG. 1K is a typical chromatogram for the t-butyl-diphenyl-silyl ether lactone (compound 4). FIG. 1L is a typical chromatogram for the t-butyl-diphenyl-silyl ether lactone (compound 4) using the optimized method. FIG. 1M is a typical chromatogram for DAPD. FIG. 1N is a typical chromatogram for DAPD using the optimized SFC method.

FIG. 2 is a graphical representation of a theoretical phase diagram for the t-butyl-diphenyl-silyl ether lactone (compound 4).

FIG. 3 are graphical representations of the selectivity of certain microbial enzymes for a particular enantiomer of the compounds of the present invention. FIGS. 3A and 3B depict the results from the screen of the butyrl ester lactone (compound 1) against various microbial enzymes. FIG. 3C depicts the results from the screen of the p-methoxybenzoyl lactone (compound 11) against various microbial enzymes. FIG. 3D depicts the results from the screen of the benzoyl lactone (compound 12) against various microbial enzymes. FIG. 3E depict the results from the screen of the iso-butyrl ester lactone (compound 13) against various microbial enzymes.

FIG. 4 is a graphical representation of the microbial resolution of the iso-butyrl ester lactone (compound 13) against the microbial enzymes CMC 103669 and CMC 103661 using various concentrations, buffers, pH ranges and temperatures.

FIG. 5 is a 400 MHz $^1$H NMR spectrum for the resolved iso-butyrl ester lactone (compound 13).

DETAILED DESCRIPTION OF THE INVENTION

The present invention includes an efficient synthetic routes to 1,3-dioxolane nucleosides from inexpensive precursors, with the option of introducing functionality as needed. These processes allow the stereoselective preparation of the biologically active isomer of these compounds.

In one embodiment of the present invention, a process for preparing a substantially pure β-D- or β-L-1,3-dioxolane nucleoside, such as β-D-DAPD, is provided, comprising:

a) preparing or obtaining an esterified 2,2-dialkoxy ethanol of the formula (Ia) or (Ib);

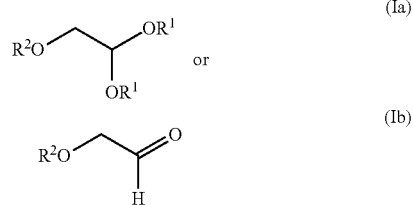

wherein:
each $R^1$ is independently alkyl, aryl, heteroaryl, heterocyclic, alkaryl, alkylheteroaryl, or alkylheterocyclic, or aralkyl; and $R^2$ is any suitable removable group such that (1) it is easily removable at the end of the synthesis, (2) it has a low molecular weight to avoid carrying large mass during the process, (3) it is commercially available and inexpensive, (4) the corresponding ester is stable under the reductive acetylation conditions, (5) the subsequent lactone is resolvable, and (6) after coupling, the corresponding anomers are easily separated, preferentially by crystallization (e.g. iso-butyryl or p-methoxy benzoyl); and then, b) cyclizing the esterified 2,2-dialkoxy ethanol of the formula (Ia) or (Ib) with glycolic acid, preferably in the presence of a Lewis acid, such as $BF_3 \cdot Et_2O$, to obtain a 1,3-dioxolane lactone of the formula (II):

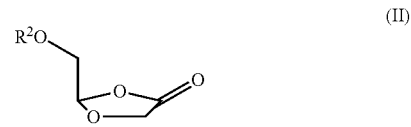

and then, c) resolving the 1,3-dioxolane lactone of the formula (II) to obtain a substantially pure D- or L-lactone; and then, d) selectively reducing with a reducing agent, such as LiAlH(OtBu)$_3$ and activating the substantially pure D- or L-chiral lactone to obtain a substantially pure D- or L-1,3-dioxolane of the formula (III):

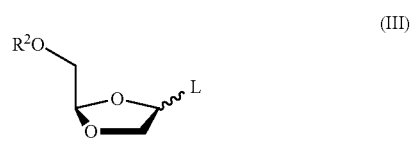

wherein:
L is a suitable leaving group, such as an O-acyl, such as OAc, halogen (F, Br, Cl or I), OMs, OTs, or the like; and then, e) coupling the substantially pure D- or L-1,3-dioxolane of the formula (III) to an activated and/or protected purine or pyrimidine base or its derivative, such as activated 2,6-dichloropurine, to obtain α:β mixture of substantially pure protected D- or L-1,3-dioxolane nucleosides of the formula (IV):

wherein:
B is a purine or pyrimidine base or its derivative; and then, f) purifying the α:β mixture of substantially pure protected D- or L-1,3-dioxolane nucleosides of the formula (IV) to obtain a substantially pure protected β-D- or β-L-1,3-dioxolane nucleoside; and then g) deprotecting the substantially pure protected β-D- or β-L-1,3-dioxolane nucleoside, if necessary, to obtain a substantially pure β-D- or β-L-1,3-dioxolane nucleoside.

In one embodiment of the present invention, the esterified 2,2-dialkoxy ethanol of the formula (Ia) is hydrolyzed to the corresponding aldehyde of formula (Ib). In a particular embodiment the esterified 2,2-dialkoxy ethanol of the formula (Ia) is hydrolyzed to the corresponding aldehyde of formula (Ib) when $R^2$ is p-methoxy benzoyl.

In one embodiment of the present invention, the resolution of the 1,3-dioxolane lactone of the formula (II) to obtain a substantially pure D- or L-lactone is accomplished using chiral chromatography. In an alternate embodiment of the present invention, the resolution of the 1,3-dioxolane lactone of the formula (II) to obtain a substantially pure D- or L-lactone is accomplished using enzymatic resolution.

Therefore, the processes of the present invention may be used to prepare compounds of formula A to D:

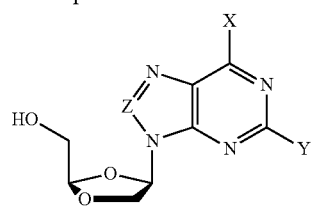

A

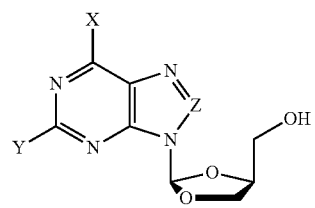

B

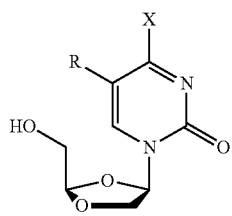

C

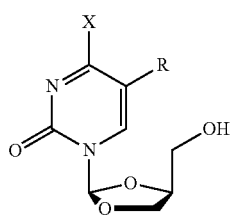

D and pharmaceutically acceptable salts or esters thereof, wherein:

R is independently H, halogen (F, Cl, Br, I), OH, OR', $OCH_3$, SH, SR', $SCH_3$, $NH_2$, NHR', $NR'_2$, lower alkyl of $C_1$-$C_4$, $CH_3$, $CH{=}CH_2$, $N_3C{=}CH_2$, $CO_2H$, $CO_2R'$, $CONH_2$, CONHR', $CH_2OH$, $CH_2CH_2OH$, $CF_3$, $CH_2CH_2F$, $CH{=}CHCO_2H$, $CH{=}CHCO_2R'$, $CH{=}CHCl$, $CH{=}CHBr$, or $CH{=}CHI$;

each R' is independently a lower alkyl of $C_1$-$C_4$;

Z is either one of CH or C—X; and each X and Y are independently H, halogen (F, Cl, Br, I), OH, OR', $OCH_3$, SH, SR', $SCH_3$, $NH_2$, NHR', $NR'_2$, or $CH_3$.

Scheme 5

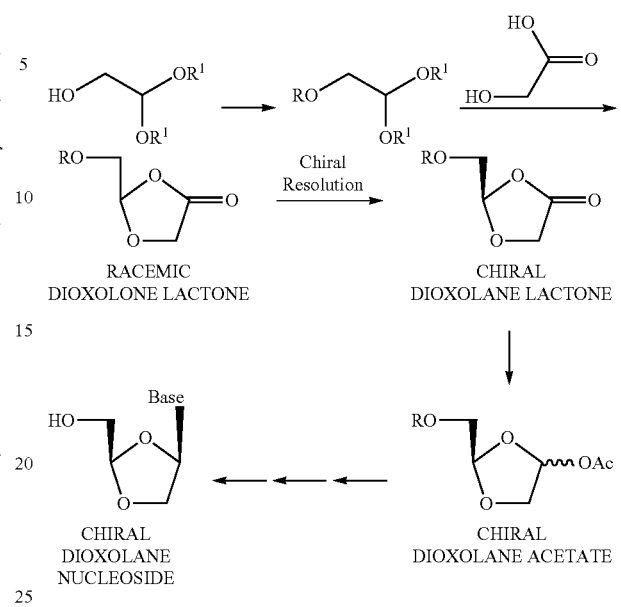

RACEMIC DIOXOLONE LACTONE → Chiral Resolution → CHIRAL DIOXOLANE LACTONE

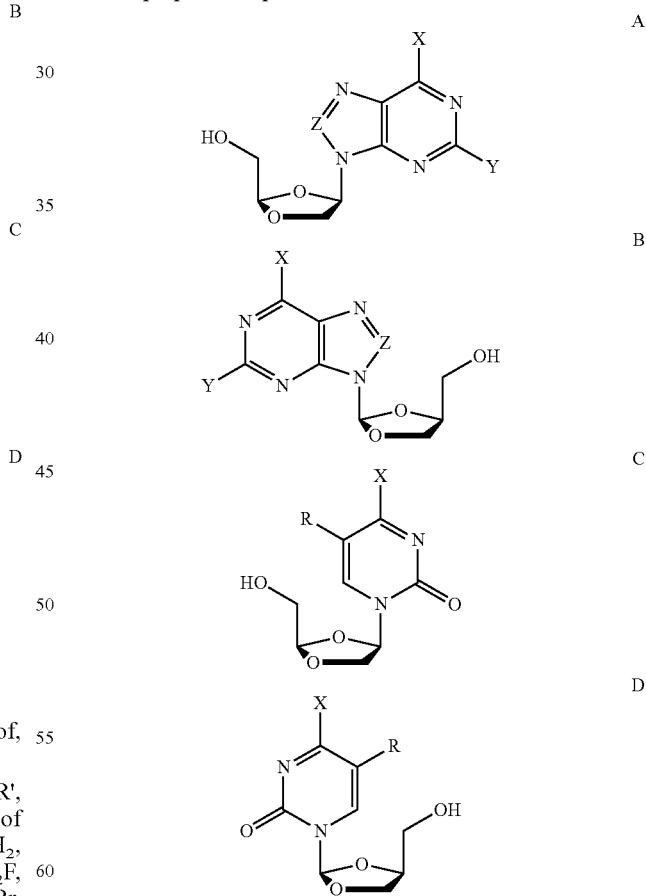

CHIRAL DIOXOLANE NUCLEOSIDE ← ← ← CHIRAL DIOXOLANE ACETATE

Therefore, the processes of the present invention may be used to prepare compounds of formula A to D:

A

B

C

D and pharmaceutically acceptable salts or esters thereof, wherein:

R is independently H, halogen (F, Cl, Br, I), OH, OR', $OCH_3$, SH, SR', $SCH_3$, $NH_2$, NHR', $NR'_2$, lower alkyl of $C_4$-$C_4$, $CH_3$, $CH{=}CH_2$, $N_3C{=}CH_2$, $CO_2H$, $CO_2R'$, $CONH_2$, CONHR', CH$_2$OH, CH$_2$CH$_2$OH, CF$_3$, CH$_2$CH$_2$F, CH=CHCO$_2$H, CH=CHCO$_2$R', CH=CHCl, CH=CHBr, or CH=CHI;

each R' is independently a lower alkyl of C$_1$-C$_4$;
Z is either one of CH or C—X; and each X and Y are independently H, halogen (F, Cl, Br, I), OH, OR', OCH$_3$, SH, SR', SCH$_3$, NH$_2$, NHR', NR'$_2$, or CH$_3$.

In a particular embodiment of the present invention, a process for preparing a substantially pure β-D-DAPD, is provided. See Scheme 6.

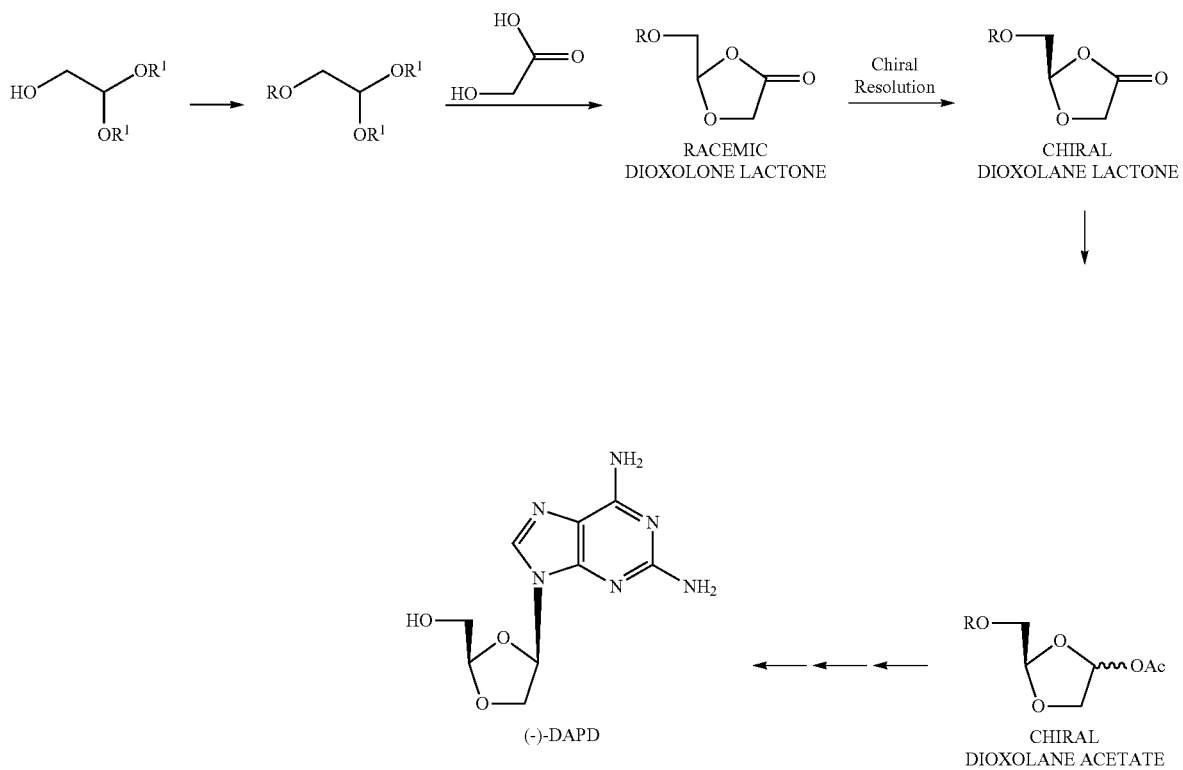

In one embodiment, the invention provides processes for resolution of compounds that can be intermediates in the synthesis of 1,3-dioxolane nucleosides, such as 1-β-D-2,6-diaminopurine dioxolane (DAPD).

In one embodiment, the invention provides a biocatalytic method for the synthesis of DAPD intermediates as shown in Scheme 7.

Scheme 7: Exemplary Routes to DAPD

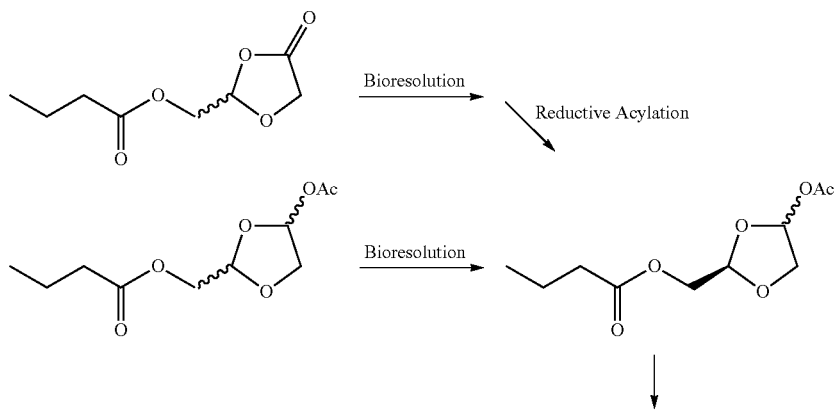

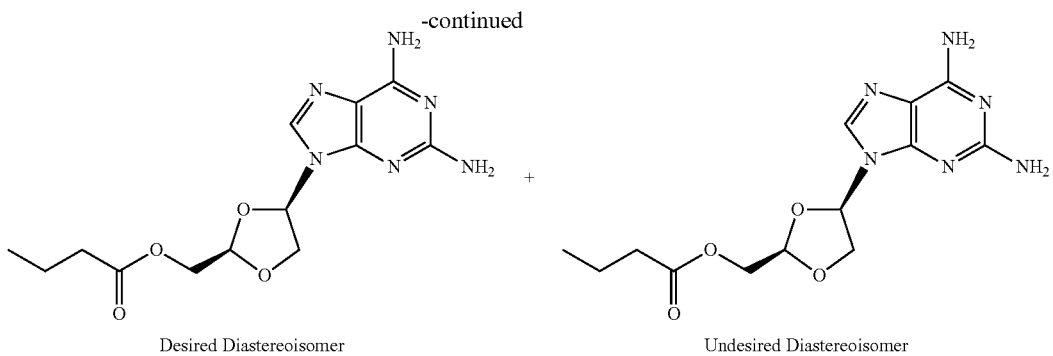

Desired Diastereoisomer     +     Undesired Diastereoisomer

In one embodiment of the invention, the 1,3-dioxolane lactone of the formula (II) is the sec-butanoate ester (Compound 13).

In one embodiment of the present invention, if a (S)-enantiomer of the butyrate ester lactone (Compound 1 of the structure below) is desired,

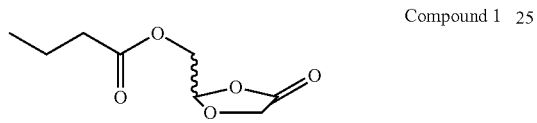

Compound 1

PPL is used for the chiral resolution. As described in the examples, PPL was identified as the most selective enzyme (22% yield, 98% ee), and was found to leave the (S)-butyrate ester isomer in a full commercial enzyme screen of all available commercial enzymes and 200 microbial enzymes.

Although in general embodiments, any effective enzyme can be used, Lipase PS, immobilized lipase *Pseudomonas* and Lipase M were identified as selective enzymes that left the (R)-butyrate ester isomer, as described in the examples. Lipase PS was found to be an efficient enzyme that possessed the required enantio-preference, giving 22% yield of 95% ee (R)-Compound 1. Therefore, in one alternative embodiment of the present invention, if a (R)-enantiomer is desired, then Lipase PS, Immobilised lipase *Pseudomonas* or Lipase M is used for the chiral resolution. In one particular embodiment, the enzyme is Lipase PS.

Although the invention is not bound to particular conditions for resolution, in one embodiment, the temperature for resolution is about 0° C. In another embodiment, the temperature is between −5° C. and 10° C., or −2° C. and +5° C. or about −1° C. to about 1° C. In another embodiment, the amount of substrate is about 100 g/L. The amount of substrate can vary, for example from 5 to 500, 20 to 200, 50 to 150, about 60, 70, 80, 90, 100, 110, 120, 130, 140, or more g/L of buffer or g/L of total reaction volume. In one embodiment, the buffer is 1:1 toluene buffer, which can be at about pH 6. In a specific embodiment, the conditions for resolution can be 0° C., 100 g/L substrate in 1:1 toluene pH 6 buffer. As described in the examples, these conditions yield 22%, 95% ee (R)-Compound 1 (E=5.3). The conditions can also vary slightly within experimental parameters for efficient resolution.

Microbial strains that resolve the compounds can vary. In one embodiment, the strains are from a species of *Acinetobacter*. The microbial screen identified 2 strains (*Acinetobacter* and *Acinetobacter junii*) which gave the (R)-butyrate in 80% ee. All available commercial enzymes and 200 microbial enzymes were screened in order to identify an efficient resolution of the butyrate ester. The microbial screen revealed 2 promising strains (CMC 3419, *Acinetobacter* and CMC 3606, *Acinetobacter junii*) which gave (R)-butyrate in 80% ee.

In one embodiment, when resolution of the butyrate ester acetate (Compound 3) of the structure below:

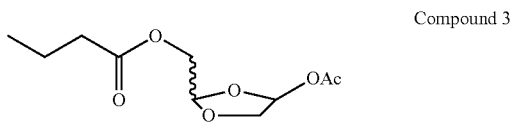 [SMILES: CCCC(=O)OCC1OCC(OC(C)=O)O1]

Compound 3 is desired, the enzyme used is Lipase PS. A full commercial enzyme screen of Compound 3 revealed that the majority of selective enzymes resolve at the acetate and not the required butyrate centre. However Lipase PS, Lipase MY and Lipase AY possessed moderate selectivity, leaving the (R)-ester isomers. These enzymes were of similar selectivity to those for Compound 1. Further investigation, revealed Lipase PS to be the most selective (effective E=3.7). Similarly, this is of comparable selectivity to the resolution of Compound 1 with Lipase PS.

In one embodiment of the invention, the resolution step occurs at an earlier stage of the synthesis, i.e. the lactone stage.

In one embodiment, when resolution of the (S)-enantiomer of p-methoxy-benzoyl lactone, 4-oxo-[1,3]dioxolan-2-ylmethyl 4'-methoxybenzoate (Compound 11).

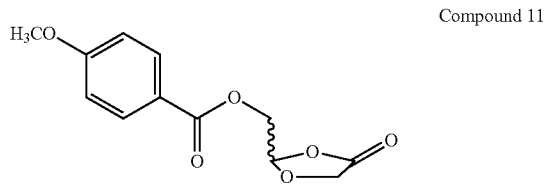 [SMILES: COc1ccc(C(=O)OCC2OCC(=O)O2)cc1]

Compound 11 is desired, then Chirazyme-L2 is used for the resolution of the lactone. A wide range of commercial and microbial enzymes were screened in order to identify an efficient resolution of Compound 11. Chirazyme-L2 was identified as the most selective enzyme giving residual ester in 39% yield, >98% ee of the (S)-enantiomer.

In another embodiment, when the resolution of the benzoyl lactone, 4-oxo-[1,3]dioxolan-2-ylmethyl benzoate (Compound 12).

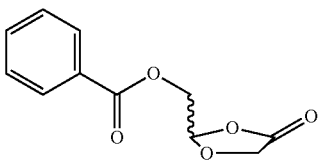

Compound 12 is desired, the enzyme used can be Chirazyme-L2. A commercial enzyme screen (ten enzymes) was undertaken for the benzoyl lactone (Compound 12). Chirazyme-L2 and Acid Protease-DS were identified as potential resolving agents in the screen. Chirazyme-L2 gave comparable selectivity for the resolutions of Compounds 11 and 12. A limited commercial enzyme screen for Compound 12 found that Chirazyme-L2 was again the most efficient enzyme.

In another embodiment, when the resolution of the (R)-enantiomer of iso-butryl lactone, 4-oxo-[1,3]dioxolan-2-yl-methyl-2'-methylpropanoate (Compound 13).

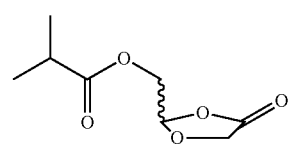

Compound 13 is desired, the enzyme used can be Chirazyme-L2. A complete commercial and microbial enzyme screen was performed for Compound 13. Chirazyme-L2 was again identified as the most selective enzyme. The configuration was determined to be the (R)-enantiomer by chemical correlation. Initial studies in MTBE-buffer gave the residual ester in 28% yield, 92% ee.

A full commercial enzyme screen for Compound 13 revealed that Chirazyme-L2, Lipase PS, Acid Protease DS and Chirazyme-L9 possessed moderate selectivity, leaving the (R)-enantiomer as the residual ester. A full microbial screen identified strains that were selective for either enantiomer. One microbe, CMC 103869, gave >95% ee lactone by running the resolution at 10° C.

In one embodiment, Compound 13 (iso-butryl lactone) was the substrate. In another embodiment, the substrate is one that affords simpler downstream chemistry, for example, simpler purification techniques. Chirazyme-L2 can be the enzyme used for resolution. In one embodiment, Chirazyme-L2 can give the (R)-configuration of residual ester.

The reaction was studied in MTBE-buffer, toluene-buffer and 2-propanol-water systems. Stability and selectivity problems were encountered with the MTBE and toluene systems. However the results in 2-propanol-water were excellent, giving a 38% yield of 94% ee Compound 13 from a 30 g input of racemate. Therefore, in one embodiment, the resolution is performed in 2-propanol-water.

An optimization study was undertaken. The process was improved by employing a monophasic alcohol-water system as solvent and using Kugelrohr distillation to purify the product. Therefore, in one embodiment, the process involves a monophasic alcohol-water system and distillation.

The bioresolution of compound 13 with Chirazyme-L2 was scaled up to 30 g at 200 gL$^{-1}$ in 2-propanol:water (9:1) and gave 4-oxo-[1,3]dioxolan-2-yl-methyl-2'-methyl-propanoate in 38% yield, 94% ee and 90% chemical purity. See Scheme 8.

Scheme 8: Conditions identified for the bioresolution of compound 13

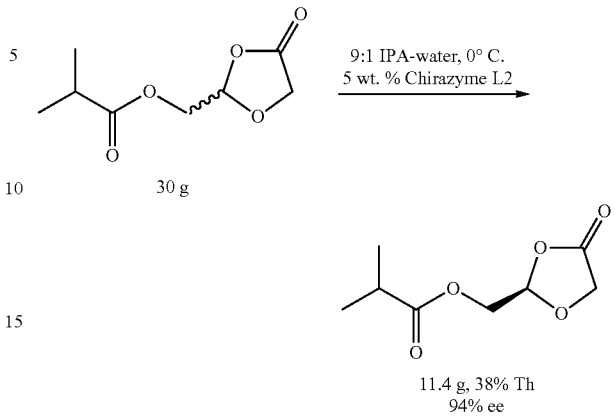

In contrast, the t-butyl-diphenyl silyl ether lactone (Compound 4) of the structure below:

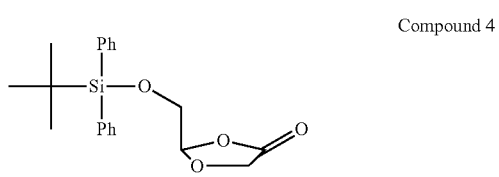 [SMILES: CC(C)(C)[Si](OCC1OCC(=O)O1)(c1ccccc1)c1ccccc1]

Compound 4 was determined as a true racemate. The phase diagram for this compound was constructed which revealed the eutectic to be at 77.5% ee.

Racemic cis-DAPD was screened with several enzymes known for their acylation activity in the presence of vinyl butyrate, but they were found to give non-stereoselective reactions. PeptiCLEC-BL and Lipase AY gave fast reactions to the desired racemic butyrate and thus may be useful to regioselectively and mildly put an ester on the oxygen. In one embodiment, PeptiCLEC-BL is used. In a separate embodiment, Lipase AY is used.

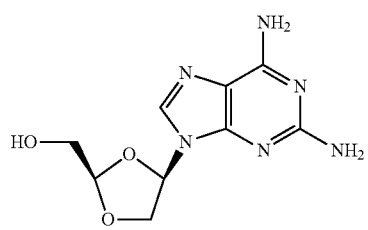 [SMILES: Nc1nc(N)c2ncn([C@H]3CO[C@@H](CO)O3)c2n1]

1-β-D-2,6-Diaminopurine Dioxolane (DAPD)

Definitions

As used herein, the term "substantially pure," "substantially free of," "substantially in the absence of" or "isolated" refers to a nucleoside composition that includes at least 85, at least 90, at least 95%, or at least 99% to 100% by weight, of the designated enantiomer of that nucleoside. In one embodiment, the process produces compounds that are substantially free of enantiomers of the opposite configuration.

The term alkyl, as used herein, unless otherwise specified, refers to a saturated straight, branched, or cyclic, primary, secondary, or tertiary hydrocarbon of $C_1$ to $C_{10}$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups. Moieties with which the alkyl group can be substituted are selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term lower alkyl, as used herein, and unless otherwise specified, refers to a $C_1$ to $C_4$ saturated straight, branched, or if appropriate, a cyclic (for example, cyclopropyl) alkyl group, including both substituted and unsubstituted forms. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The term aryl, as used herein, and unless otherwise specified, refers to phenyl, biphenyl, or naphthyl. The term includes both substituted and unsubstituted moieties. The aryl group can be substituted with one or more moieties selected from the group consisting of bromo, chloro, fluoro, iodo, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term alkaryl or alkylaryl refers to an alkyl group with an aryl substituent. The term aralkyl or arylalkyl refers to an aryl group with an alkyl substituent.

The term halo, as used herein, includes bromo, chloro, fluoro, and iodo.

The term heteroatom, as used herein, refers to oxygen, sulfur, nitrogen, and phosphorus.

The term acyl refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term purine or pyrimidine base includes, but is not limited to, adenine, $N^6$-alkyl-purines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 5-fluoro-cytosine, 5-methylcytosine, 6-azapyrimidine, including 6-aza-cytosine, 2- and/or 4-mercapto-pyrmidine, uracil, 5-halouracil, including 5-fluorouracil, $C^5$-alkylpyrimidines, $C^5$-benzyl-pyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amido-pyrimidine, $C^5$-cyanopyrimidine, $C^5$-nitro-pyrimidine, $C^5$-aminopyrimidine, $N^2$-alkyl-purines, $N^2$-alkyl-6-thiopurines, 5-azacytidinyl, 5-azauracilyl, triazolopyridinyl, imidazolo-pyridinyl, pyrrolopyrimidinyl, and pyrazolopyrimidinyl. Purine bases include, but are not limited to, guanine, adenine, hypoxanthine, 2,6-diaminopurine, 2-(Br, Fl, Cl or I)-purine optionally with a substituent including an amino or carbonyl group in the 6-position, and 6-(Br, Cl, or I)-purine optionally with a substituent including an amino or carbonyl group in the 2-position. Functional oxygen and nitrogen groups on the base can be protected as necessary or desired. Suitable protecting groups are well known to those skilled in the art, and include trimethylsilyl, dimethylhexylsilyl, t-butyldimethylsilyl, t-butyldiphenylsilyl, trityl, alkyl groups, and acyl groups such as acetyl and propionyl, methanesulfonyl, and p-toluenesulfonyl.

The term heteroaryl or heteroaromatic, as used herein, refers to an aromatic that includes at least one sulfur, oxygen, nitrogen or phosphorus in the aromatic ring. The term heterocyclic refers to a nonaromatic cyclic group wherein there is at least one heteroatom, such as oxygen, sulfur, nitrogen or phosphorus in the ring. Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, iso-thiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, and pteridinyl, aziridines, thiazole, isothiazole, 1,2,3-oxadiazole, thiazine, pyridine, pyrazine, piperazine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, $N^6$-alkylpurines, $N^6$-benzylpurine, $N^6$-halopurine, $N^6$-vinypurine, $N^6$-acetylenic purine, $N^6$-acyl purine, $N^6$-hydroxyalkyl purine, $N^6$-thioalkyl purine, thymine, cytosine, 6-azapyrimidine, 2-mercaptopyrmidine, uracil, $N^5$-alkylpyrimidines, $N^5$-benzylpyrimidines, $N^5$-halopyrimidines, $N^5$-vinylpyrimidine, $N^5$-acetylenic pyrimidine, $N^5$-acyl pyrimidine, $N^5$-hydroxyalkyl purine, and $N^6$-thioalkyl purine, and isoxazolyl. The heteroaromatic group can be optionally substituted as described above for aryl. The heterocyclic or heteroaromatic group can be optionally substituted with one or more substituent selected from halogen, haloalkyl, alkyl, alkoxy, hydroxy, carboxyl derivatives, amido, amino, alkylamino, dialkylamino. The heteroaromatic can be partially or totally hydrogenated as desired. As a nonlimiting example, dihydropyridine can be used in place of pyridine. Functional oxygen and nitrogen groups on the heterocyclic or heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenylsulfonyl.

These purine or pyrimidine bases, heteroaromatics and heterocycles can be substituted with alkyl groups or aromatic rings, bonded through single or double bonds or fused to the heterocycle ring system. The purine base, pyrimidine base, heteroaromatic, or heterocycle may be bound to the sugar moiety through any available atom, including the ring nitrogen and ring carbon (producing a C-nucleoside).

Abbreviations used throughout include ee: Enantiomeric excess for the starting material (s) or product (p); c: Conversion; and E: Enantioselectivity constant.

Detailed Description of Process Steps

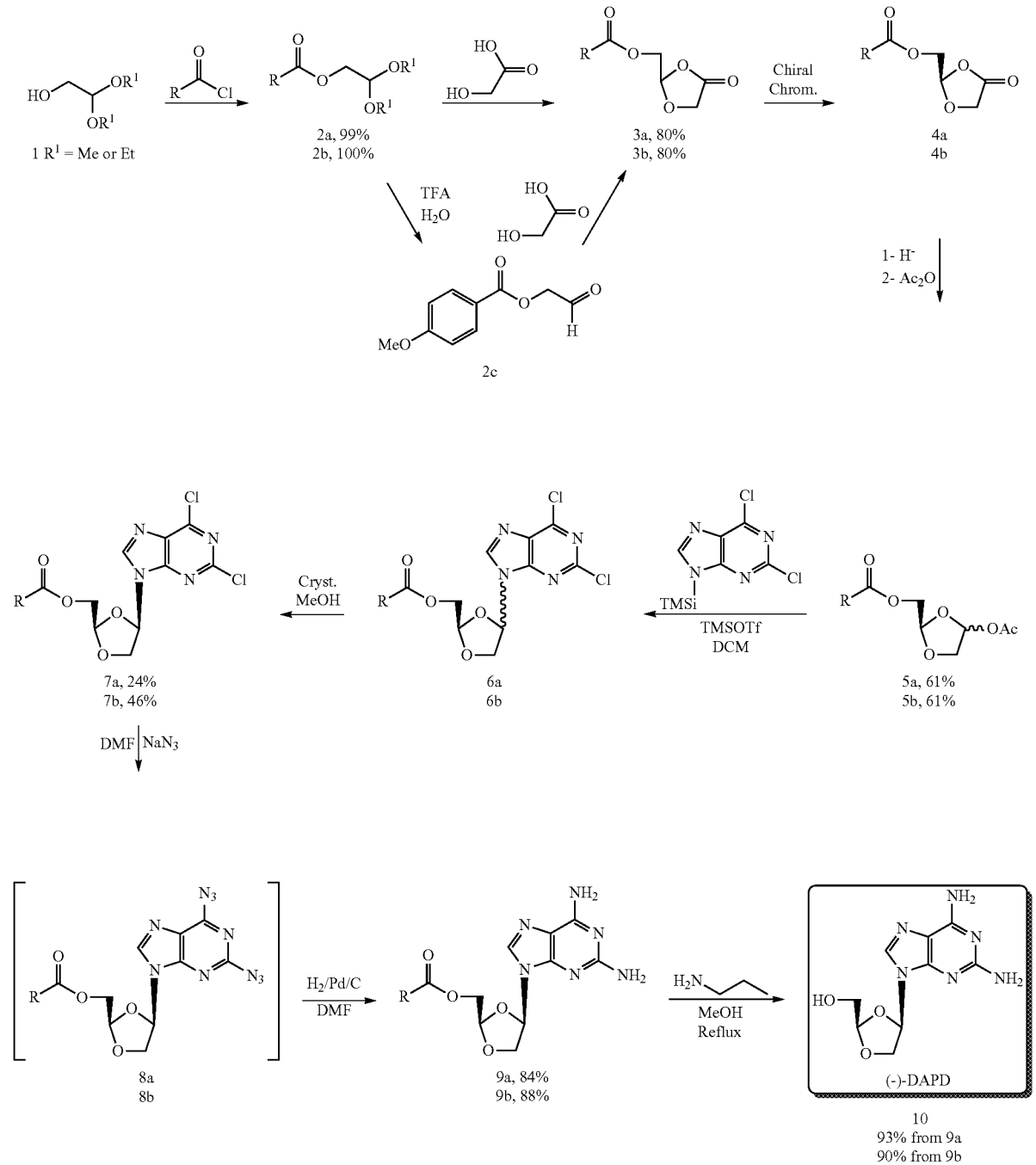

Initially a 2,2-dialkoxy-ethanol (1) was esterified with the corresponding acid chloride in quantitative yields. In the case of the iso-butyryl (2a) ester, cyclization to the corresponding dioxolane lactone (3a), was affected with glycolic acid in the presence of a Lewis acid ($BF_3.Et_2O$) in 80% yield. However, under the same conditions, the p-methoxy benzoate ester (2b) afforded the corresponding lactone in low yield and purity. Much better results were achieved in a two step procedure in which the acetal was first hydrolyzed to the corresponding aldehyde (2c), which then was subjected to similar cyclization conditions, affording the corresponding lactone (3b) in 80% yield as a solid. The lactones were resolved by chiral chromatography[13]. Selective reduction of the chiral lactones (4a and 4b) with $LiAlH(OtBu)_3$ and subsequent treatment with acetic anhydride afforded the corresponding acetates (5a and 5b) in reasonable yields, after purification by flash column chromatography. Coupling with 2,6-dichloropurine under Vobruggen conditions afforded crude mixtures of α:β anomers of the corresponding nucleosides (6a and 6b). The iso-butyrate ester was first purified by column chromatography and then crystallized from MeOH to afford the pure β anomer (7a) in a 24% yield. The p-methoxy benzoate ester nucleoside did not require chromatography, and was purified by crystallization from MeOH to afford pure β anomer (7b) in 46% yield. The chlorines were replaced with amino groups in a two-step procedure by treatment with sodium azide and then hydrogenation. The corresponding intermediates (9a and 9b) were isolated and fully described. Removal of the protecting groups was achieved with n-butylamine in refluxing MeOH to afford (−)-DAPD (10) in 93% and 90% yield respectively.

The total overall yields from the corresponding chiral lactones (5a and 5b) were: 11.4% for the iso-butyrate and 22.2% for the p-methoxy benzoate.

EXAMPLES

Melting points were determined in open glass capillaries by use of a Melt-Temp II apparatus with a digital thermometer. $^1$H-NMR spectra were recorded at 400 MHz with a Varian XL-400 spectrometer. Evaporations were performed under diminished pressure using a Buchi rotatory evaporator at 40° C. unless otherwise indicated. Solutions were dried over anhydrous $Na_2SO_4$. TLC was performed on precoated glass plates (0.25 mm) with Silica Gel 60$F_{254}$ (E. Merck, Darmstad). Flash column chromatography was performed with Silica Gel 60 (230-400 mesh, E. Merck, Darmstad). Elemental analyses were performed by Atlantic Microlab (Atlanta, Ga.). High Resolution Mass Spectra (HRMS) were performed by Analytical Instrument Group Inc. (Raleigh, N.C.).

Gas Chromatography Analysis: Samples were prepared by dissolving 1 mg sample per 1 ml THF, or other suitable solvent. A 1 µl injection volume was used. Samples were separated using a 30m HP-5 (crosslinked 5% PH ME siloxane) capillary column, Hewlett Packard part #19091J-413. The inlet temperature was set at 200° C., and the oven temperature as follows: 35° C. for 1 minute, ramp to 250° C. at 12.5° C./minute, hold at 250° C. for 1.8 minutes. The flame ionization detector temperature was set at 250° C. The carrier gas was nitrogen set at a nominal flow of 8.0 ml/minute.

HPLC Analysis:

Method A: Column: Chiralpak AD-RH, 150×4.6 mm. Mobile phase: Methanol. Gradient: Isocratic. Flow rate: 0.5 ml/min. Run time: 30 min. Detection: UV at 280 nm.

Method B: Column. Aquasil C18, 150×4.6 mm. Mobile phase: solvent A: acetonitrile, solvent B: 50 mmol $NH_4OAc$, 0.1% AcOH in water. Gradient: time: 0 min., A: 1%, B: 99%; time: 17 min., A: 50%, B: 50%, then isocratic. Flow rate: 1.0 ml/min. Run time: 30 min. Detection: UV at 290 nm.

Method C: Column. Chiralpak AD, 250×4.6 mm. Mobile phase: Methanol. Gradient: Isocratic. Flow rate: 0.8 ml/min. Run time: 20 min. Detection: UV at 254 nm.

Example 1

Isobutyric acid 2,2-dimethoxy-ethyl ester (2a)

4-Methoxy-benzoic acid 2,2-diethoxy-ethyl ester (2b)

To a well-stirred solution of 2,2-diethoxy or 2,2-dimethoxy-ethanol (1, 100 mmol), DMAP (61 mg, 0.5 mmol) and $Et_3N$ (16 ml, 11.64 g, 115 mmol) in EtOAc or tert-butylmethyl ether (50 ml) at 0° C. was slowly added the corresponding acid chloride (105 mmol). After stirring for 16 h at room temperature the reaction mixture was diluted with EtOAc (50 ml), and successively washed with: (c) $NaHCO_3$ (2×100 ml), brine (2×100 ml), dried, filtered and evaporated to afford:

Isobutyric acid 2,2-dimethoxy-ethyl ester (2a, 99%) as a yellow liquid that was used in the next step without any further purification. GC ($R_t$=5.24 min., 98%); $^1$H-NMR ($CDCl_3$) δ: 4.57 (1H, t, J=5.2, $(MeO)_2CHCH_2$—), 4.11 (2H, d, J=5.2, $(MeO)_2CHCH_2$—), 3.40 (6H, s, $CH_3O$—), 2.60 (1H, m, $OCOCH(CH_3)_2$), 1.54 (6H, d, J=6.8, OCOCH$(CH_3)_2$).

4-Methoxybenzoic acid 2,2-diethoxy-ethyl ester (2b, 100%) as a syrup that was used in the next step without any further purification. GC ($R_t$=13.7 min, 99%); $^1$H-NMR ($CDCl_3$) δ: 7.98 (2H, d, J=9.0, ArH), 6.89 (2H, d, J=9.0, ArH), 4.79 (1H, t, J=5.6, $(EtO)_2CHCH_2$—), 4.28 (2H, d, J=5.6, $(EtO)_2CHCH_2$—), 3.82 (3H, s, $CH_3O$—), 3.73 (2H, m, $CH_3CH_2O$—), 3.59 (2H, m, $CH_3CH_2O$—), 1.22 (6H, t, J=6.9, $CH_3CH_2O$—).

Example 2

Isobutyric acid 4-oxo-[1,3]-dioxolan-2-yl methyl ester (3a)

To a well stirred solution of the corresponding acetal (2a, 30 mmol) and α-hydroxy acetic acid (3.42 g, 45 mmol) in acetonitrile (30 ml) at 0° C. was slowly added $BF_3.EtO_2$ (6.38 g, 5.70 ml, 45 mmol). The solution was left at room temperature overnight with stirring. The solution was partitioned between EtOAc (150 ml) and (c) $NaHCO_3$ (150 ml). The organic solution was successively washed with (c) $NaHCO_3$ (150 ml), brine (2×150 ml), dried, filtered and evaporated to afford:

Isobutyric acid 4-oxo-[1,3]-dioxolan-2-yl methyl ester (3a, 80%) as a colorless syrup. GC ($R_t$=7.89 min., 95%); $^1$H-NMR ($CDCl_3$) δ: 5.83 (1H, s, H-2), 4.35-4.20 (4H, m, H-5, H-5' and —$CH_2OCO$—), 2.62 (1H, m, $(CH_3)_2CHCOO$—), 1.19 (6H, d, J=7.0, $(CH_3)_2CHCOO$—).

Calculated mass for $C_8H_{13}O_5$ $(M+1)^+$: 189.0763. Found: (H.R.F.A.B.M.S.): 189.0763.

Example 3

4-Methoxybenzoic acid 4-oxo-[1,3]-dioxolan-2-yl methyl ester (3b)

A solution of 4-methoxybenzoic acid 2,2-diethoxy-ethyl ester (2b, 7.5 g, 28 mmol) in $Cl_2CH_2$ (75 ml) was treated with TFA (16.7 g, 11.3 ml, 140 mmol) and water (7.5 g, 7.5 ml, 28 mmol). The homogeneous solution was stirred for 3.5 hours at room temperature until GC showed complete reaction. The solution was concentrated in vacuo at 40° C. and then diluted with hexane and concentrated in vacuo several times to remove traces of TFA. The product, 4-methoxybenzoic acid 2-oxo-ethyl ester (2c, 5.9 g, 28 mmol, 100%) was isolated as an amorphous white solid and was used in the next step without any further purification. GC ($R_t$=11.0 min, 95%); $^1$H-NMR (CDCl$_3$) δ: 9.72 (1H, s, HCO—), 8.06 (2H, d, J=8.8, ArH), 6.95 (2H, d, J=8.8, ArH), 4.87 (2H, s, HCOCH$_2$O—), 3.87 (3H, s, OCH$_3$).

To a well stirred solution of the crude aldehyde (2c, 5.9 g, 28 mmol) and α-hydroxy acetic acid (5.2 g, 68 mmol) in DME (100 ml) at 0° C. was slowly added BF$_3$.EtO$_2$ (12.3 g, 11.0 ml, 85 mmol). The solution was left at room temperature overnight with stirring. The solution was partitioned between EtOAc (150 ml) and (c) NaHCO$_3$ (150 ml). The organic solution was successively washed with (c) NaHCO$_3$ (150 ml), brine (2×150 ml), dried, filtered and evaporated to afford a syrup. The syrup was treated with DME (15 ml) and a solid precipitated. After stirring for 30 minutes, the solid was filtered to afford 4-methoxybenzoic acid 4-oxo-[1,3]-dioxolan-2-yl methyl ester (3b, 5.7 g, 23 mmol, 80%) as a white granular solid; GC ($R_t$=14.7 min, 99%); mp: 61-63° C.; $^1$H-NMR (CDCl$_3$) δ: 7.97 (2H, d, J=9.2, ArH), 6.91 (2H, d, J=9.2, ArH), 5.95 (1H, t, J=3.0, H-2), 4.57 (1H, dd, J=3.0 and J=12.6, —CH$_2$OCO—), 4.50 (1H, dd, J=3.0 and J=12.6, —CH$_2$OCO—), 4.41 (1H, d, J=15.0, H-5), 4.31 (1H, d, J=15.0, H-5), 3.87 (3H, s, OCH$_3$).

Calculated for C$_{12}$H$_{12}$O$_6$, C, 57.14; H, 4.80. Found: C, 57.40; H, 4.93.

Example 4

Isobutyric acid 4-oxo-[1,3]-dioxolan-2(R)-yl methyl ester (4a)

Racemic isobutyric acid 4-oxo-[1,3]-dioxolan-2-yl methyl ester (3a) was resolved by chiral chromatography[13] to afford two fractions corresponding to each one of the enantiomers. Both fractions were colorless syrups. The first fraction corresponded to the R enantiomer (4a, isobutyric acid 4-oxo-[1,3]-dioxolan-2(R)-yl methyl ester); HPLC (Method A, $R_t$=7.80 min., 100%); $[α]_D^{20}$=20.20° (c 0.25, MeOH). The second fraction corresponded to the S enantiomer (isobutyric acid 4-oxo-[1,3]-dioxolan-2(S)-yl methyl ester); HPLC (Method A, $R_t$=9.30 min., 100%); $[α]_D^{20}$=−14.40° (c 0.25, MeOH).

Example 5

4-Methoxybenzoic acid 4-oxo-[1,3]-dioxolan-2(R)-yl methyl ester (4b)

Racemic 4-methoxybenzoic acid 4-oxo-[1,3]-dioxolan-2-yl methyl ester (3b) was resolved by chiral chromatography[7] to afford two fractions corresponding to each one of the enantiomers. Both fractions were white solids. The first fraction corresponded to the R enantiomer (4b, 4-methoxybenzoic acid 4-oxo-[1,3]-dioxolan-2(R)-yl methyl ester); mp: 76-78° C.; HPLC (Method A, $R_t$=13.59 min., 99%); $[α]_D^{20}$=12.20° (c 0.25, MeOH). The second fraction corresponded to the S enantiomer (4-methoxybenzoic acid 4-oxo-[1,3]-dioxolan-2(S)-yl methyl ester); mp: 76-78° C.; HPLC (Method A, $R_t$=20.76 min., 99%); $[α]_D^{20}$=−13.50° (c 0.25, MeOH).

Example 6

Isobutyric acid 4-acetoxy-[1,3]-dioxolan-2(R)-yl methyl ester (5a)

4-Methoxybenzoic acid 4-acetoxy-[1,3]-dioxolan-2(R)-yl methyl ester (5b)

To a well stirred solution of the corresponding lactone (4a or 4b, 15 mmol) in dry THF (45 ml) at −10° C., was slowly added a 1.0 M solution of LiAlH(OtBu)$_3$ in THF (19.5 ml, 19.5 mmol) over a period of 20 minutes, maintaining the temperature between −15° C. and −10° C. The reaction was followed by GC and was stirred for 30 minutes at room temperature (complete disappearance of starting material). The solution was again cooled to −10° C. and DMAP (0.92 g, 7.50 mmol) was added in one portion followed by the dropwise addition of Ac$_2$O (15.3 g, 14.20 ml, 150 mmol). The reaction was further stirred for 1 h at −15° C., and then overnight at room temperature. The solution was cooled to −15° C. and quenched with MeOH (40 ml). After stirring for 20 minutes at room temperature, the reaction was concentrated in vacuo to a red syrup that was purified by flash column chromatography (250 g silica, hexane:EtOAc 3:1) to afford.

Isobutyric acid 4-acetoxy-[1,3]-dioxolan-2(R)-yl methyl ester (5a, 61%) as a yellow syrup. $^1$H-NMR (CDCl$_3$) shows almost a 1:1 mixture of anomers, δ: 6.40 (d, J=3.8) and 6.37 (d, J=3.8) corresponding to H-4 α and H-4 β; 5.41 (t, J=3.7) and 5.32 (t, J=3.7) corresponding to H-2 α and H-2 β.

4-Methoxybenzoic acid 4-acetoxy-[1,3]-dioxolan-2(R)-yl methyl ester (5b, 61%) as a yellow syrup. $^1$H-NMR (CDCl$_3$) shows almost a 1:1 mixture of anomers, δ: 6.44 (dd, J=2.1 and J=4.2) and 6.37 (d, J=4.0) corresponding to H-4 α and H-4 β; 5.54 (t, J=3.6) and 5.45 (t, J=4.0) corresponding to H-2 α and H-2 β.

Example 7

Isobutyric acid 4(R)-(2,6-dichloro-purin-9-yl)-[1,3]-dioxolan-2(R)-yl methyl ester (7a)

4-Methoxybenzoic acid 4(R)-(2,6-dichloro-purin-9-yl)-[1,3]-dioxolan-2(R)-yl methyl ester (7b)

A suspension of 2,6-dichloropurine (1.27 g, 6.73 mmol), ammonium sulfate (38 mg, 0.29 mmol) and 1,1,1,3,3,3-hexamethyldisilazane (8.45 g, 11.04 ml, 52.3 mmol) was heated at reflux for 2.5 hs. The resulting solution was cooled to ambient temperature whereby a thick solid precipitated. The solids were redissolved through the addition of dry dichloromethane (14.9 ml). The solution was then cooled to −10° C., and a solution of the corresponding acetate (5a or 5b, 8.6 mmol) in dry dichloromethane (10 ml) was slowly added over a period of 20 minutes, maintaining the temperature between −10° C. and −5° C. Then, TMSOTf (2.5 g, 2.08 ml, 10.4 mmol) was slowly added over a period of 20 minutes. The reaction was left overnight with stirring at room temperature. The solution was diluted with dichloromethane (120 ml) and quenched with water (150 ml). The organic layer was separated and successively washed with water (150 ml), (c) NaHCO$_3$ (2×150 ml), water (2×150 ml), dried, filtered and evaporated to a syrup (crude 6a) or a yellow solid (crude 6b).

Crude 6a was further purified by column chromatography (Hexane:AcOEt 4:1) to afford 6a as a 1.2:1 β:α mixture of anomers, according to $^1$H-NMR. The mixture was slowly crystallized from MeOH (10 ml) to afford isobutyric acid 4(R)-(2,6-dichloro-purin-9-yl)-[1,3]-dioxolan-2(R)-yl methyl ester (7a, 24%) as a white solid and characterized as the β anomer; mp: 145-147° C.; $[\alpha]_D^{20}$=−47.67° (c 0.25, MeOH); $^1$H-NMR (CDCl$_3$) δ: 8.52 (1H, s, H-8), 6.55 (1H, d, J=4.9, H-4), 5.34 (1H, t, J=5.7, H-2), 4.58-4.30 (4H, m, —CH$_2$COO—, H-5 and H-5'), 2.61 (1H, m, (CH$_3$)$_2$ CHCOO—), 1.19 (3H, d, J=6.8, (CH$_3$)$_2$CHCOO—), 1.14 (3H, d, J=6.8, (CH$_3$)$_2$CHCOO—).

Calculated for C$_{13}$H$_{14}$Cl$_2$N$_4$O$_4$: C, 43.23; H, 3.91; N, 15.51. Found: C, 43.39; H, 3.91; N, 15.58.

Crude 6b was first washed with hot hexane to afford 4-methoxy-benzoic acid 4-(2,6-dichloro-purin-9-yl)-[1,3]-dioxolan-2(R)-yl methyl ester (6b) as a yellow solid. $^1$H-NMR indicated a 2:1 mixture of β:α anomers. This mixture was slowly crystallized from MeOH (100 ml) to afford 4-methoxybenzoic acid 4(R)-(2,6-dichloro-purin-9-yl)-[1,3]-dioxolan-2(R)-yl methyl ester (7b, 46%) as a yellow solid and characterized as the β anomer; mp: 154-156° C.; HPLC (Method B, R$_t$=20.73 min.); $[\alpha]_D^{20}$=−53.80° (c 0.25, MeOH); $^1$H-NMR(Cl$_3$CD) δ: 8.41 (1H, s, H-8), 7.91 (2H, d, J=8.5, ArH), 6.92 (2H, d, J=8.5, ArH), 6.53 (1H, d, J=4.8, H-4), 5.44 (1H, bs, H-2), 4.70-4.30 (4H, m, H-5, H-5' and —CH$_2$OCO—), 3.85 (3H, s, OCH$_3$).

Calculated mass for C$_{17}$H$_{15}$Cl$_2$N$_4$O$_5$ (M+1)$^+$: 425.0419. Found (H.R.F.A.B.M.S.): 425.0420.

Example 8

Isobutyric acid 4(R)-(2,6-diazido-purin-9-yl)-[1,3]-dioxolan-2(R)-yl methyl ester (8a)

4-Methoxybenzoic acid 4(R)-(2,6-diazido-purin-9-yl)-[1,3]-dioxolan-2(R)-yl methyl ester (8b)

To a well-stirred solution of the corresponding dichloropurine nucleoside (7a or 7b, 2.9 mmol) in dry DMF (13.5 ml) was added NaN$_3$ (390 mg, 6.0 mmol). The reaction mixture was left at room temperature with stirring for 4 h. The mixture was filtered through celite to afford a solution of:

Isobutyric acid 4(R)-(2,6-diazido-purin-9-yl)-[1,3]-dioxolan-2(R)-yl methyl ester (8a) or 4-methoxybenzoic acid 4(R)-(2,6-diazido-purin-9-yl)-[1,3]-dioxolan-2(R)-yl methyl ester (8b) in DMF (70 ml) which was used in the next step without any further purification.

Example 9

Isobutyric acid 4(R)-(2,6-diamino-purin-9-yl)-[1,3]-dioxolan-2(R)-yl methyl ester (9a)

4-Methoxybenzoic acid 4(R)-(2,6-diamino-purin-9-yl)-[1,3]-dioxolan-2(R)-yl methyl ester (9b)

The solution from the previous reaction (8a or 8b) was hydrogenated (Parr apparatus, 50 psi) at room temperature, in the presence of 10% Pd/C (200 mg) overnight. The mixture was filtered through Celite and the filter cake washed with additional DMF.

In the case of 8a, the solution was concentrated to dryness and purified by column chromatography (Cl$_3$CH:MeOH 9:1) to afford a white solid that was crystallized from iso-propanol to afford isobutyric acid 4(R)-(2,6-diamino-purin-9-yl)-[1,3]-dioxolan-2(R)-yl methyl ester (9a, 84% after correction for the presence of one molecule of 2-propanol that co-crystallizes) as a white solid; mp: 143-145° C.; $[\alpha]_D^{20}$=56.45° (c 0.25, MeOH); $^1$H-NMR (CDCl$_3$) δ: 7.84 (1H, s, H-8), 6.33 (1H, dd, J=1 and J=5.1, H-4), 5.29 (3H, t, J=3.2, H-2 and NH$_2$), 4.70 (2H, bs, NH$_2$), 4.50 (1H, dd, J=1 and J=9.0, H-5), 4.33 (2H, d, J=3.2, —CH$_2$COO—), 4.23 (1H, dd, J=5.1 and J=9.0, H-5'), 2.60 (1H, m, (CH$_3$)$_2$CHCOO—), 1.18 (3H, d, J=6.2, (CH$_3$)$_2$CHCOO—), 1.14 (3H, d, J=7.2, (CH$_3$)$_2$CHCOO—).

Calculated for C$_{13}$H$_{18}$N$_6$O$_4$·2-propanol: C, 50.25; H, 6.85; N, 21.98. Found: C, 50.16; H, 6.84; N, 21.92.

In the case of 8b, the solution was concentrated to a final volume of 15 ml in vacuo at 60° C. The solution was diluted with water (150 ml) and after a few minutes a solid precipitated. The product was filtered, washed with water, dried overnight at 50° C. under vacuum to afford 4-methoxybenzoic acid 4(R)-(2,6-diamino-purin-9-yl)-[1,3]-dioxolan-2 (R)-yl methyl ester (9b, 88%) as an amorphous solid; HPLC (Method B, R$_t$=15.41 min.); $[\alpha]_D^{20}$=−95.75° (c 0.25, MeOH); $^1$H-NMR (DMSO-d$_6$) δ: 7.82 (2H, d, J=8.8, ArH), 7.80 (1H, s, H-8), 7.02 (2H, d, J=8.8, ArH), 6.77 (2H, bs, NH$_2$), 6.23 (1H, dd, J=5.5 and J=1.6, H-4), 5.85 (2H, bs, NH$_2$), 5.36 (1H, t, J=3.3, H-2), 4.65 (1H, dd, J=9.4 and J=1.6, H-5), 4.46 (2H, d, J=3.4, —CH$_2$OCO—), 4.26 (1H, dd, J=9.4 and J=5.5, H-5'), 3.84 (3H, s, OCH$_3$).

Calculated mass for C$_{17}$H$_{19}$N$_6$O$_5$: 387.1417. Found (H.R.F.A.B.M.S.): 387.1417.

Example 10

4(R)-[-(2,6-Diamino-purin-9-yl)-[1,3]-dioxolan-2(R)-yl]-methanol, [10, (−)-DAPD] from 9a A solution of isobutyric acid 4(R)-(2,6-diamino-purin-9-yl)-[1,3]-dioxolan-2(R)-yl methyl ester (9a, 100 mg, 0.31 mmol) and n-butylamine (0.45 g, 0.62 ml, 6.2 mmol) in MeOH (10 ml) was heated at reflux for 4 hs. The reaction was cooled to ambient temperature and concentrated in vacuo to afford a solid that was triturated with tert-butyl methyl ether and filtered to afford a solid that was crystallized from EtOH: water (1:4.5 ml) to afford (−)-DAPD (10, 75 mg, 0.29 mmol, 93%) as a white solid; mp: 237-239° C. (lit.[2] mp: 236-237° C.); HPLC (Method C, R$_t$=8.7 min., an authentic sample of (−)-DAPD showed R$_t$=8.7 min. and a sample of (+) DAPD showed R$_t$=6.0 min.); DAPD; $^1$H-NMR (DMSO-d$_6$) δ: 7.80 (1H, s, H-8), 6.74 (2H, bs, NH$_2$), 6.20 (1H, d, J=5.5, H-4), 5.84 (2H, bs, NH$_2$), 5.16 (1H, t, J=6.3, OH), 5.03 (1H, t, J=2.9, H-2), 4.42 (1H, d, J=9.7, H-5), 4.18 (1H, dd, J=9.7 and J=5.5, H-5'), 3.58 (2H, dd, J=6.3 and J=2.9, —CH$_2$OH).

Calculated for C$_9$H$_{12}$N$_6$O$_3$: C, 42.86; H, 4.80; N, 33.32. Found: C, 42.88; H, 4.79; N, 33.32.

Example 11

4(R)-[-(2,6-Diamino-purin-9-yl)-[1,3]-dioxolan-2(R)-yl]-methanol, [10, (−)-DAPD] from 9b A suspension of 4-methoxybenzoic acid 4(R)-(2,6-diamino-purin-9-yl)-[1,3]-dioxolan-2(R)-yl methyl ester (9b, 1.0 g, 2.6 mmol) and n-butylamine (3.7 g, 5.0 ml, 50 mmol) in MeOH (25 ml) was heated at reflux for 4 hours. The reaction was concentrated in vacuo to afford a yellow solid that was suspended in Cl$_3$CH at room temperature and filtered, to afford (−) DAPD (10, 590 mg, 2.3 mmol, 90%) as a white solid. Physical properties were identical to the sample of (−)-DAPD obtained above.

Example 12

Determination of the Enantioselectivity Constant

The enantioselectivity of a simple hydrolysis reaction may be characterized by the E value (C. S Chen, C. J. Sih, Y.

Fujimoto and G. Girdaukus, *J. Am. Chem. Soc.*, 1982, 104, 7294). This numerically represents the ratio of the specificity constants of the catalyst for the two enantiomers. The E value allows direct comparison of catalyst selectivity, even if the reactions have gone to different conversions.

To calculate the E value, the extent of conversion and the optical purity of the remaining starting material and/or the hydrolysis product are needed. If both $ee_s$ and $ee_p$ are known, one can calculate conversion (c) using Equation 1. If only $ee_s$ or $ee_p$ is known, c determined at the termination of the hydrolysis can be used to calculate E (Equation 2).

$$c = \frac{ee_s}{ee_s + ee_p} \quad \text{Equation 1}$$

$$E = \frac{\ln[(1-c)(1-ee_s)]}{\ln[(1-c)(1+ee_s)]} = \frac{\ln[1-c(1+ee_p)]}{\ln[1-c(1-ee_p)]} \quad \text{Equation 2}$$

Abbreviations:
ee=Enantiomeric excess for the starting material (s) or product (p)
c=Conversion
E=Enantioselectivity constant Example 13

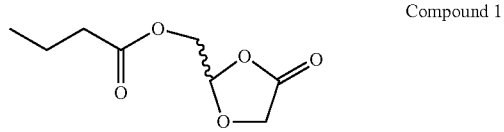

Compound 1

Analytical Development for Compound 1

A chiral assay was required for Compound 1. A baseline separation was achieved by chiral GC using the Chirasil DEX CB column. See FIG. 1A.
GC Conditions:
Column: Chirasil DEX CB
Dimensions: 25m×0.25 mm
Temp. Program: 140° C. for 10 minutes then to 200° C. at 15° C./min
Carrier gas: Helium @ 20 psi
Detection: FID @ 200° C.
Retention times: 1—7.46 mM (R)-enantiomer
2—7.70 mM (S)-enantiomer
Enzymatic Screening for Compound 1

Lipases: To each scintillation vial was added 50 μL Compound 1, MTBE (5 mL) and 50 mM $KH_2PO_4$, pH 7 (5 mL), followed by 25 mg enzyme. The vials were shaken in an incubator set at 30° C. Aliquots were removed periodically and assayed by TLC (50% EtOAc/heptane) and chiral GC.

Proteases and esterases: As above, except the reaction solvent was 5 mL, 50 mM $KH_2PO_4$, pH 7 or 8 with no MTBE. Acid protease reactions were performed at pH 3 using 0.1 M lactic acid solution [pepsin, Acid protease A (Newlase A), and Acid protease II (Newlase II)].

In some cases 25 mg, 50% wt. of enzyme gave extremely fast reactions and so 100% conversion was reached before meaningful assays could be performed. In these cases the reactions were performed again with the appropriate amount of enzyme to give a reasonable rate of reaction (usually 5% wt.). Enzymes that required smaller loadings were Chirazyme-L2, -E1 and -E2, all the CLECs, Choline esterase, *Candida* esterase (Altus), PPL, Lipase PS and Lipase AK.

Two sets of conditions were used for the screen of racemic Compound 1, depending upon whether the enzyme used was a lipase or a protease/esterase. For lipase-catalyzed hydrolyses, the reaction solvent was 1:1 MTBE:50 mM potassium phosphate buffer pH 7. For protease and esterase-catalyzed hydrolyses, reactions were carried out in 50 mM potassium phosphate buffer, pH 7 or 8 (or pH 3 for acid proteases) with no immiscible organic co-solvent. Reactions were carried out in a shaker bath at 30° C. and followed by TLC, with $ee_s$ values determined by GC analysis (Chirasil Dex-CB column).

The alcohol product from hydrolysis of the butyrate ester appears to be unstable since several new spots on TLC were produced during the reactions. Thus with no chiral assay for the product possible, approximate conversions were estimated from the TLC analysis.

The results from the screens are shown in the tables below. Table 1 shows the enzymes that selectively left peak 1 in the butyrate chiral assay, while Table 2 shows the enzymes that selectively left peak 2 in the butyrate chiral assay. It is noteworthy that there appeared to be a very large number of enzymes that give non-stereoselective hydrolysis of Compound 1, which indicated that the substrate is unstable under the reaction conditions. When a control reaction was performed containing no enzyme, hydrolysis still occurred. Further investigation of the stability of the substrate is described herein.

TABLE 1

Enzymes that selectively leave peak 1 in the butyrate ee assay

| Enzyme | Time | $ee_s$ | Approximate conversion |
| --- | --- | --- | --- |
| SAWA immobilised lipase | 6 h | 92% | >50% |
| *Pseudomonas* | O/N | — | No S.M |
| Lipase M | 6 h | 26% | |
|  | O/N | 91% | ~75% |
| Lipase PS | 1 h | 17% | |
|  | 3.75 h | 89% | >50% |
|  | 5 h | — | No S.M. |
| Lipase F1 Biocon. | 6 h | 13% | |
|  | O/N | 88% | >75% |
| Lipase AK | 2.75 h | 32% | |
|  | 5 h | 64% | |
|  | O/N | 64% | >50% |
| Chirazyme-L9 | 1 h | 10% | |
|  | 5 h | 64% | >50% |
|  | O/N | — | No S.M. |
| ChiroCLEC-PC | 10 min | 2% | |
|  | 1 h | 46% | >50% |
| Lipase MY | 6 h | 11% | |
|  | O/N | 33% | >75% |
| Lipase DS | 6 h | 2% | |
|  | O/N | 28% | |
| *Candida Esterase* (Altus) | 10 min | 27% | >50% |
|  | 1 h | — | No S.M. |
| Protease B | O/N | 26% | |
| Lipase F-DS | 6 h | 22% | |
|  | O/N | — | No S.M. |
| Newlase F | 6 h | 4% | |
|  | O/N | 20% | |
| Lipase F | 6 h | 20% | |
|  | O/N | — | No S.M. |
| Alcalase | 1 h | 8% | |
|  | 5 h | 13% | |
|  | O/N | 18% | ~50% |
| Lipase R | 6 h | 9% | |
|  | O/N | 17% | |

TABLE 2

Enzymes that selectively leave peak 2 in the butyrate ee assay

| Enzyme | Time | ee$_s$ | Approximate conversion |
|---|---|---|---|
| PPL | 5 h | 92% | |
| | O/N | 96% | >50% |
| Lipase G | 6 h | 3%% | |
| | O/N | 41% | >50% |
| PLE, tech grade | 1 h | 35% | >50% |
| Chirazyme-E1 | 30 min | 13% | |
| | 1 h | 21% | >50% |
| Chirazyme-L2 | 1 h | 8% | |
| | 1.75 h | 22% | >50% |

α-Chymotrypsin gave no reaction with Compound 1.

The following enzymes gave unselective reactions with Compound 1 (<10% ee$_s$): Lipase AY, Lipase A "Amano" 6, Lipase A "Amano" 12, Lipase N conc, Lipase AP6, Sigma CCL, Wheat germ lipase, Chirazyme-L5, ChiroCLEC-CR, Protease M, Peptidase R, Acid Protease A, Acid Protease II, Acid Protease DS, Protease A-DS, Protease N, Protease A2G, Protease NL, Protease DS, Protease S, Protease P "Amano" 6, Prozyme 6, Proleather, Bromelain-F, Papain W-40 (Amano), Papain (Sigma), Protease X, Protease XXXI, Savinase, Esperase, Pepsin, ChiroCLEC-BL, Ketoprofen Esterase and Chirazyme-E2.

Example 14

Scale-Up of PPL Resolution of Compound 1

In order to determine which was the (R)-isomer, a quantity of resolved Compound 1 was resolved using the most promising enzyme from the screen set forth supra, and taken through the synthetic sequence to an intermediate where the isomer elution order by chiral assay was known. The most promising enzyme from the screen was PPL (porcine pancreatic lipase, Sigma), thus this reaction was scaled up to 50 g racemic substrate input (Scheme 10).

Scheme 10: Large scale PPL resolution of Compound 1

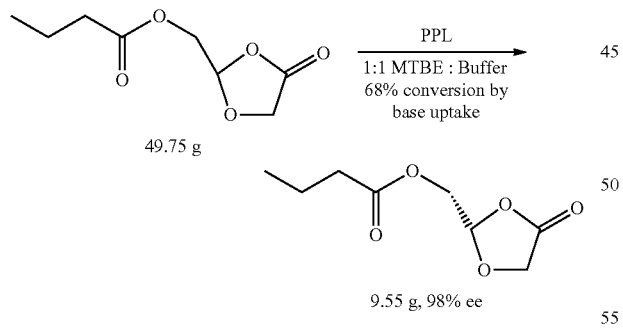

Minimal optimization of the reaction conditions was performed, apart from increasing the substrate concentration to 50 g/L (a reaction on 5 g substrate was successfully run as a trial). The 50 g reaction was initiated with 5% wt PPL at 30° C. and 3 M NaOH added as the reaction proceeded in an attempt to maintain the pH at 7. However the reaction was extremely fast and after 25 minutes was cooled to 15° C. and the pH maintained at pH 6.

In particular, to a 2 L jacketed vessel at 30° C. was added MTBE (500 mL), 50 mM KH$_2$PO$_4$, pH 7 (500 mL) and racemic Compound 1 (49.75 g, 0.265 mol, TP-0257/98/D). To the stirred mixture (pH 7) was added PPL (2.5 g, 5 wt %), then 3M NaOH was added to maintain the pH at pH 6. Due to the speed of the reaction, after 25 min the vessel was cooled to 15° C. and the reaction run at this temperature. The ee$_s$ was measured at time intervals by removing aliquots of MTBE, diluting with more MTBE, drying (MgSO$_4$), and analyzing by chiral GC. After 1 h 10 min the ee$_s$ had reached 98% and the reaction was worked-up. The mixture was filtered through celite and the celite washed with MTBE (200 mL). The mixture was allowed to separate and the organic layer retained. The aqueous was then re-extracted with MTBE (500 mL). The MTBE extractions were combined, dried (MgSO$_4$) and evaporated in vacuo to give 22 g of a crude yellow oil. The crude product was purified by silica flash column chromatography (20% EtOAc:80% heptane) to give 9.55 g (5)-Compound 1 as a very pale yellow oil, 98% ee, 95% pure by GC-MS. A further 1.5 g of less pure material was also obtained. Combined yield was 22%.

GC-MS (CPSil8 CB/MS, 30m×0.25 mm, 60° C. for 5 min, 10° C./min to 300° C.) 13.98 min, M=173 (M$^+$-CH$_3$), 95% pure by peak area.

$^1$H NMR (200 MHz, CDCl$_3$) δ 5.85 (t, 1H, CH—O), 4.35 (m, 4H, 2×CH$_2$O), 2.35 (t, 2H, CH$_2$), 1.7 (sextet, 2H, CH$_2$), 0.95 (t, 3H, CH$_3$).

The ee$_s$ was measured at time intervals (peak 2 in ee assay).

TABLE 3

PPL resolution of Compound 1

| Time | Conversion by base uptake | Actual pH | ee$_s$ |
|---|---|---|---|
| 5 min | 28% | 6.5 | — |
| 10 min | 57% | 6.5 | 53% |
| 55 min | 63% | 6.0 | 89% |
| 1 h 10 min | 68% | 6.0 | 98% |

The reaction was worked up after 1 h 10 min and the isolated resolved Compound 1 purified by silica column chromatography. This yielded 9.55 g, 95% pure, 98% ee ester, along with 1.5 g of less pure ester (22% overall yield). The impurity in the main batch of ester (9.55 g) was butyric acid. This material was taken through the synthetic sequence to an intermediate where the isomer elution order by chiral assay was known, and was determined to be (S)-Compound 1. To obtain the (R)-isomer, an enzyme that selectively left peak 1 in the Compound 1 chiral assay was needed.

Example 15

Optimization of Commercial Enzyme Resolutions Giving (R)-Compound 1

As can be seen from Table 1, the initial screen had shown SAWA immobilized lipase, Lipase M, Lipase PS and F1 Biocon. lipase to be potential candidates to efficiently give (R)-Compound 1. The resolutions were scaled up to determine their selectivities (F1 Biocon. lipase is no longer commercially available).

The enzyme was added to 2-5 g of ester in 15-20 mL each of solvent and buffer (0.2 N KH$_2$PO$_4$). Sodium hydroxide solution was added to control the pH. The work-up procedure was to filter (Celite), extract (MTBE), wash with saturated aqueous sodium bicarbonate, dry (MgSO$_4$) and concentrate. Analysis was by chiral GC (Chirasil Dex CB). The variables studied were enzyme, solvent, pH and temperature (see Table 4).

Initial trials with Lipase PS, Lipase M and SAWA immobilized *Pseudomonas lipase* in pH 7 phosphate buffer gave the remaining substrate with enantiomeric excesses of 90%, but the recovery of (R)-Compound 1 was low (<5%). The stability of the butyrate was investigated at pH 7 and pH 6 under standard reaction conditions but without enzyme present (entries 20 and 21). At pH 7 significant base was consumed to maintain pH and after work-up and isolation only 50% of (1) was recovered after 3.5 h. Stability is significantly better at pH 6. Possibly, the mode of breakdown is opening of the lactone-acetal to give an aldehyde and glycolic acid (Scheme 11).

Scheme 11: Posssible decomposition pathway of Compound 1

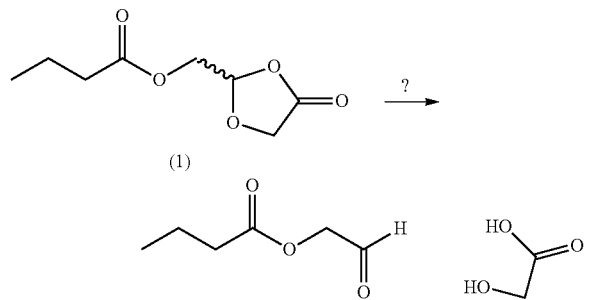

Resolution with Lipase PS was investigated further in the Examples herein. Variables studied for optimization were concentration, solvent:buffer volume ratio, enzyme loading, additives and temperature.

The optimal conditions were determined as 0° C., 100 g/L substrate in 1:1 toluene:potassium phosphate buffer (pH 6) which gives 95% ee, 22% yield of (R)-Compound 1. At 200 g/L substrate concentration, 95% ee (R)-Compound 1 was obtained in 17% yield.

Example 16

Microbial Enzyme Screen

From a screen of around 200 strains (using the new 96-well plate method), 7 positives were identified which left the (R)-isomer of Compound 1 (peak 1). These were classified as positive in so far as they hydrolyzed the ester and gave >10% ee of remaining substrate, thus having potential for generating high ee ester.

The screen was performed in 0.1M $Na_2HPO_4/NaH_2PO_4$, pH 6.0 with 20 g/l ester at 25° C. for approximately 16 h. The results are depicted in FIGS. 5A and 5B.

The seven positive strains (peak 1) from the primary screen were grown up in TSB (tryptone soya broth) flasks and the cell pastes harvested. These were re-suspended at 10% w/v in 0.1 M $Na_2HPO_4/NaH_2PO_4$, pH 6.0+20 g/L ester and shaken in scintillation vials (at 1.0 mL per vial) for up to 92 hours at 25° C. The results are shown in Table 5.

TABLE 4

Optimization of resolution of Compound 1

| Entry | Enzyme | Co-solvent | pH | Temp/ °C. | mmol Base:SM | S.M. ee/% | Yield S.M./% | $E^{(i)}$ | Comment |
|---|---|---|---|---|---|---|---|---|---|
| 1 | Lipase PS | MTBE | 6-7 | 20 | 20:28 | >95 | 0 | — | 10% enzyme, negligible S.M., 17 min |
| 2 | Lipase PS | MTBE | 7 | 20 | 33:27 | >95 | 0 | — | Negligible S.M., 2 h |
| 3 | Lipase PS | MTBE | 6 | 20 | 13:12 | 90 | 6.2 | 1.9 | |
| 4 | Lipase PS | MTBE | 7 | 10 | 28:26 | >95 | 0 | — | Negligible S.M., 2.5 h |
| 5 | Lipase PS | MTBE | 5-7 | 10 | 10:13 | 82 | 0 | — | Negligible S.M., 4.5 h |
| 6 | Lipase PS | heptane | 6-7 | 0 | 8:17 | 88 | NI | — | 1M buffer |
| 7 | Lipase PS | heptane | 6 | 0 | 10:24 | 88 | 14 | 3.1 | |
| 8 | Lipase PS | toluene | 6 | 0 | 10:19 | 54 | 45 | 4.3 | |
| 9 | Lipase PS | MEK | 6 | 0 | 2:20 | 19 | 70 | 3.1 | |
| 10 | Lipase PS | THF | 6 | 0 | 4:19 | 36 | 46 | 2.6 | |
| 11 | Lipase PS | DCM | 6 | 0 | 4:19 | 12 | 68 | 1.9 | |
| 12 | Lipase PS | dioxane | 6 | 0 | 6:18 | 50 | 22 | 1.9 | |
| 13 | SAWA | MTBE | 6 | 20 | 8.6:15 | 81 | 21 | 3.3 | |
| 14 | SAWA | MTBE-EtOH | — | 20 | — | 0 | NI | — | No water, racemic |
| 15 | SAWA | toluene | 6 | 0 | 13:19 | 37 | 41 | 2.4 | |
| 16 | Lipase M | MTBE | 6 | 20 | 20:15 | — | 0 | — | No S.M. 20 h |
| 17 | Lipase M | MTBE | 7 | 0-5 | 28:27 | 83 | NI | — | 1M buffer |
| 18 | Lipase M | toluene | 6 | 0 | 14:19 | 39 | 42 | 2.5 | |
| 19 | CLEC-PC | MTBE | 6 | 20 | — | — | 0 | — | No S.M. remaining |
| 20 | none | MTBE | 7 | 20 | 9:9 | — | 48 | — | 3.5 h, S.M. decomposes |
| 21 | none | MTBE | 6 | 20 | no base | — | NI | — | 2 h, no base consumed |

$^{(i)}$Enantioselectivity constant - see Example 12

Two other controls showed that starting ester of 98% ee is not racemized by the reaction conditions at pH 6 or pH 7. A further test reaction showed that after 24 hours at pH 6, 100 g/L substrate in 2:1 toluene:1 M buffer and 0° C., greater than 90% yield of starting material was recovered with no loss of enantiomeric excess. Thus racemization and substrate stability under these reaction conditions is not a problem.

With these results in mind, all further enzyme reactions were performed at pH 6. The best results from the study are shown in entries 7, 8, 9 and 13. The most promising enzyme resolution was with Lipase PS in toluene/pH 6 buffer giving an E value of 4.3. This would give a yield of 17% at 95% ee.

TABLE 5

Further investigation of positive microbial strains

| No. | CMC No. | Name | Time/h | Peak 1 | Peak 2 | $ee_s$ |
|---|---|---|---|---|---|---|
| 1 | 3127 | *Serratia liquifaciens* | 17.75 | 13291 | 10863 | 10.1% |
| | | | 24 | 71866 | 67553 | 3.1% |
| | | | 47 | | | |
| | | | 92 | | | |
| 2 | 3322 | *P. alcaligenes* | 17.75 | | | |

TABLE 5-continued

Further investigation of positive microbial strains

| CMC No. | No. | Name | Time/h | Peak 1 | Peak 2 | ee$_s$ |
|---|---|---|---|---|---|---|
| 3 | 3373 | *Acinetobacter* sp | 24 | | | |
| | | | 47 | | | |
| | | | 17.75 | 67157 | 64051 | 2.4% |
| | | | 24 | 9827 | 8169 | 9.2% |
| | | | 47 | | | |
| | | | 92 | | | |
| 4 | 3418 | Unidentified | 17.75 | 14606 | 9430 | 21.5% |
| | | | 24 | 11627 | 8948 | 13.0% |
| | | | 47 | | | |
| | | | 92 | | | |
| 5 | 3419 | *Acinetobacter* | 17.75 | 69727 | 30271 | 39.5% |
| | | | 24 | 55222 | 22993 | 41.2% |
| | | | 47 | 18804 | 2077 | 80.1% |
| | | | 92 | | | |
| 6 | 3606 | *Acinetobacter junii* | 17.75 | 114861 | 14557 | 77.5% |
| | | | 24 | 93782 | 23728 | 59.6% |
| | | | 47 | 45250 | 6326 | 75.5% |
| | | | 92 | 7789 | 880 | 79.7% |
| 7 | 3635 | Unidentified | 17.75 | 26812 | 23798 | 6.0% |
| | | | 24 | 6685 | 4022 | 24.9% |
| | | | 47 | 2134 | 1139 | 30.4% |
| | | | 92 | | | |
| 8 | | Blank No Enzyme | 17.75 | 254977 | 256011 | 0.2% |
| | | | 24 | 215295 | 216508 | 0.3% |
| | | | 47 | 86300 | 85001 | 0.8% |
| | | | 92 | 20053 | 19960 | 0.2% |

The results from the control show that the ester is not stable over 24 hours at 25° C. There is a 97% decrease in peak area size between the peak areas at 17 and 92 hours. This clearly explains why all the samples peak areas show a dramatic drop. Of the strains re-screened, CMC 3606 (*Acinetobacter junii*) and CMC 3419 (*Acinetobacter*) showed good enantioselectivity (80% ee for peak one). These two strains were re-grown [CMC 3606 in flasks (as it was originally an unidentified bacteria) and CMC 3419 in fermentation vessels] ready for further evaluation. For CMC 3322 (*P. alcaligenes*) there was no detectable ester after 17 hours. This may be due to a shift in pH (with the cells lysing) or from a high esterase activity.

Example 17

Compound 3

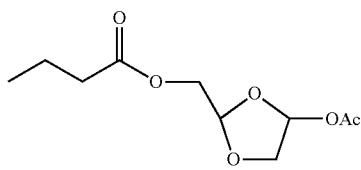

Analytical Development for Compound 3

A chiral GC assay was developed to separate the four possible diastereoisomers of Compound 3. Details of the assay conditions are as set forth below.

GC Conditions:

| | |
|---|---|
| Column: | Chiraldex GTA |
| Dimensions: | 30 m × 0.25 mm |
| Temp. Program: | 100° C. for 20 minutes then to 160° C. at 2° C./min |
| Carrier gas: | Helium @ 14 psi |
| Detection: | FID @ 200° C. |
| Retention times: | 1 - 41.74 minutes    2 - 41.96 minutes |
| | 3 - 43.07 minutes    4 - 43.82 minutes |

Achiral GC-MS of the starting ester gave two peaks at 15.98 and 16.27 min (diastereoisomers) in a ratio of 1:1.4 respectively. See FIG. 1B. Comparison of the four chiral GC ee/de assay peaks and GC-MS peaks indicated that peaks 1 and 2 were enantiomers and peaks 3 and 4 were enantiomers in the ee/de assay.

Enzyme Screen, Compound 3

Lipases: To each scintillation vial was added 50 µL Compound 3 (TP-0259/98/A), MTBE (5 mL) and 50 mM $KH_2PO_4$, pH 7 (5 mL), followed by 20 mg enzyme. The vials were shaken in an incubator set at 30° C., with aliquots removed periodically and assayed by TLC (50% EtOAc/heptane) and chiral GC.

Proteases and esterases: As above, except the reaction solvent was 5 mL, 50 mM $KH_2PO_4$, pH 7 or 8 with no MTBE. Acid protease reactions were performed at pH 3 using 0.1 M lactic acid solution [pepsin, Acid protease A (Newlase A), and Acid protease II (Newlase II)].

For some enzymes that were known to be very active for these substrates, the reactions were performed with an appropriate amount of enzyme to give a reasonable rate of reaction, usually 10-15 wt %. Enzymes that required these reduced loadings were Chirazyme-L2, -E1 and -E2, all the CLECs, Choline esterase and *Candida* esterase (Altus).

Racemic Compound 3 was screened for enzymatic hydrolysis with commercially available lipases, proteases and esterases. All lipase reactions were carried out in the presence of 50 µL Compound 3, 5 mL MTBE, 5 mL pH 7 phosphate buffer and 50% wt. enzyme (except Chirazyme-E1, Chirazyme-E2, Chirazyme-L2, *Candida* Esterase, Choline esterase and CLECs, 10% wt.). Esterase and protease reactions were performed without MTBE present. The reactions were followed by TLC and chiral GC.

The stereochemistry at the acetate centre is not as important since it is set later in the synthesis of the bulk active DAPD. Thus it is desirable to resolve with respect to the butyrate centre. However, initially it was unknown which peak corresponded to which isomer. Control reactions, containing no enzyme, showed that the substrate was stable under the reaction conditions. The results from the screen for resolution of Compound 3 are shown in Tables 6-11.

TABLE 6

Enzyme screen of Compound 3 - enzymes selective for peaks 1/3

| Enzyme | Time | Peak 1 | Peak 2 | Peak 3 | Peak 4 | ee | Peaks | Conversion by TLC |
|---|---|---|---|---|---|---|---|---|
| Peptidase R | 3.5 h | 32.0 | 27.5 | 40.0 | 0.5 | 8% | 1 | ~20% |
|  |  |  |  |  |  | 98% | 3 |  |
|  | O/N | 68.5 | 0.0 | 31.5 | 0.0 | 99% | 1 | ~50% |
|  |  |  |  |  |  | 99% | 3 |  |
| Protease M | 1.25 h | 31.0 | 20.0 | 37.0 | 12.0 | 22% | 1 | <20% |
|  |  |  |  |  |  | 51% | 3 |  |
|  | 6.5 h | 58.5 | 2.0 | 39.5 | 0.0 | 93% | 1 | ~50% |
|  |  |  |  |  |  | 99% | 3 |  |
| Acid Protease A (Newlase A) | 4 h | 36.5 | 3 | 60.5 | 0 | 85% | 1 | ~50% |
|  |  |  |  |  |  | 99% | 3 |  |
| Protease B | 7 h | 17.5 | 12.5 | 62.5 | 7.5 | 17% | 1 | ~50% |
|  |  |  |  |  |  | 79% | 3 |  |
|  | 24 h | 31 | 0 | 69 | 0 | 99% | 1 | >80% |
|  |  |  |  |  |  | 99% | 3 |  |
| Chirazyme L2 | 45 min | 28.0 | 21.0 | 35.5 | 16.0 | 14% | 1 | ~30% |
|  |  |  |  |  |  | 38% | 3 |  |
|  | 1.75 | 39.0 | 15.5 | 41.0 | 4.5 | 43% | 1 | ~50% |
|  |  |  |  |  |  | 80% | 3 |  |
| Protease A | 3.5 h | 40.5 | 20.5 | 28.5 | 10.5 | 33% | 1 | 40-50% |
|  |  |  |  |  |  | 46% | 3 |  |
|  | 6.5 h | 51.5 | 18.0 | 26.5 | 4.0 | 48% | 1 | ~60% |
|  |  |  |  |  |  | 74% | 3 |  |
| Protease A 2G | 3.5 h | 40.0 | 23.5 | 22.5 | 16.5 | 26% | 1 | ~50% |
|  |  |  |  |  |  | 15% | 3 |  |
|  | O/N | 70.5 | 5.0 | 15.0 | 10.0 | 87% | 1 | >75% |
|  |  |  |  |  |  | 20% | 3 |  |
| Ketoprofen Esterase | 3.5 h | 8.5 | 1.5 | 56.0 | 40.0 | 70% | 1 | ~60% |
|  |  |  |  |  |  | 17% | 3 |  |
|  | 6.5 h | 9.0 | 2.0 | 56.0 | 40.0 | 64% | 1 | ~60% |
|  |  |  |  |  |  | 17% | 3 |  |
| Protease N | 1.25 h | 22.5 | 18.0 | 31.0 | 28.5 | 11% | 1 | 10-20%. |
|  |  |  |  |  |  | 4% | 3 |  |
|  | 6.5 h | 24.0 | 17.5 | 33.0 | 25.5 | 16% | 1 | 10-20% |
|  |  |  |  |  |  | 13% | 3 |  |
| PPL | 3.5 h | 34.0 | 25.5 | 20.0 | 20.0 | 14% Rac | 1 3/4 | 10-20% |
|  | 6.5 h | 43.5 | 26.0 | 16.0 | 14.0 | 25% | 1 | ~60% |
|  |  |  |  |  |  | 7% | 3 |  |

These results show that Peptidase R, Protease M and Acid Protease A (Newlase A) have excellent selectivity for peaks 1 and 3; whilst Protease B, Chirazyme-L2, and Protease A have reasonable selectivity for peaks 1 and 3.

TABLE 7

Enzyme screen of Compound 3 - enzymes selective for peaks 1/4

| Enzyme | Time | Peak 1 | Peak 2 | Peak 3 | Peak 4 | ee | Peaks | Conversion by TLC |
|---|---|---|---|---|---|---|---|---|
| PLE | 1.25 h | 35.0 | 19.0 | 11.5 | 35.0 | 30% | 1 | ~50% |
|  |  |  |  |  |  | 50% | 4 |  |
|  | 6.5 h | 70.0 | 10.0 | 0.0 | 20.0 | 75% | 1 | >80% |
|  |  |  |  |  |  | 99% | 4 |  |
| Chirazyme-E1 | 15 min | 33.0 | 19.0 | 17.0 | 31.0 | 27% | 1 | ~50% |
|  |  |  |  |  |  | 29% | 4 |  |
|  | 45 min | 52.0 | 12.0 | 8.0 | 28.0 | 63% | 1 | ~80% |
|  |  |  |  |  |  | 56% | 4 |  |
| Chirazyme-E2 | 1.25 h | 46.5 | 20.0 | 11.0 | 22.0 | 40% | 1 | ~60% |
|  |  |  |  |  |  | 33% | 4 |  |
|  | 3.5 h | 54.5 | 19.5 | 8.5 | 17.5 | 47% | 1 | >80% |
|  |  |  |  |  |  | 26% | 4 |  |
| PLAP | 24 h | 32.5 | 24.5 | 9.5 | 33.5 | 14% | 1 | >50% |
|  |  |  |  |  |  | 56% | 4 |  |

Thus PLE and Chirazyme-E1 are reasonably selective for peaks 1 and 4.

TABLE 8

Enzyme screen of Compound 3 - enzymes selective for peak 1

| Enzyme | Time | Peak 1 | Peak 2 | Peak 3 | Peak 4 | ee | Peaks | Conversion by TLC |
|---|---|---|---|---|---|---|---|---|
| Papain (Sigma) | 7 h | 64.5 | 19 | 16.5 | 0 | 54% 100% | 1 3 | ~50% |
|  | 24 h | 93.5 | 5 | 1.5 | 0 | 90% | 1 | >50% |
| Protease P Amano 6 | 1 h | 44 | 23.5 | 14 | 18.5 | 30% 14% | 1 4 | ~50% |
|  | 4 h | 84.5 | 15.5 | 0 | 0 | 69% | 1 | >80% |
| Prozyme 6 | 1 h | 44 | 26 | 12 | 18 | 26% 20% | 1 4 | ~50% |
|  | 4 h | 78 | 22 | 0 | 0 | 56% | 1 | >80% |

These results show that Papain displays very good selectivity for peak 1.

TABLE 9

Enzyme screen of Compound 3 - enzymes selective for peaks 2/3

| Enzyme | Time | Peak 1 | Peak 2 | Peak 3 | Peak 4 | ee | Peaks | Conversion by TLC |
|---|---|---|---|---|---|---|---|---|
| Lipase AK | 3.5 h | 22.0 | 52.5 | 24.0 | 2.0 | 41% 85% | 2 3 | ~20% |
|  | 6.5 h | 14.0 | 73.5 | 12.5 | 0.0 | 68% 99% | 2 3 | ~60% |
| Lipase MY | 1.25 h | 19.0 | 31.5 | 36.0 | 13.5 | 25% 45% | 2 3 | 30-40% |
|  | 6.5 h | 8.5 | 76.0 | 15.5 | 0.0 | 80% 99% | 2 3 | >80% |
| Lipase AY | 3.5 h | 20.5 | 39.5 | 32.5 | 7.5 | 32% 63% | 2 3 | 10-20% |
|  | 6.5 h | 17.5 | 56.0 | 25.0 | 1.5 | 52% 89% | 2 3 | ~50% |
| CCL | 3.5 h | 20.5 | 27.5 | 32.5 | 19.0 | 15% 26% | 2 3 | 10-20% |
|  | 6.5 h | 20.5 | 33.5 | 33.0 | 13.0 | 24% 43% | 2 3 | 30-40% |
| Acid Protease A | 6.5 h | 21.5 | 24.0 | 29.0 | 25.5 | 5% 6% | 2 3 | ~30% |
|  | O/N | 22.5 | 36.0 | 25.0 | 16.0 | 23% 22% | 2 3 | ~50% |
| Protease NL | 7 h | 22 | 24 | 33 | 21 | Rac 22% | 2/1 3 | <50% |
|  | 24 h | 23.5 | 29.5 | 35.5 | 11.5 | 11% 51% | 2 3 | ~50% |

These results show that Lipase AK, Lipase MY and Lipase AY are reasonably selective for peaks 2 and 3.

TABLE 10

Enzyme screen of Compound 3 - enzymes selective for peaks 2/4

| Enzyme | Time | Peak 1 | Peak 2 | Peak 3 | Peak 4 | ee | Peaks | Conversion by TLC |
|---|---|---|---|---|---|---|---|---|
| Protease XXXI | 4 h | 25.5 | 29.5 | 19 | 26 | 7% 16% | 2 4 | ~50% |
|  | 24 h | 31 | 46 | 7.5 | 15.5 | 19% 34% | 2 4 | >50% |
| Proleather | 4 h | 25.5 | 30.5 | 18.5 | 25.5 | 9% 16% | 2 4 | ~50% |

Thus no enzyme that is selective for peaks 2 and 4 gives particularly high enantiomeric excesses.

TABLE 11

Enzyme screen of Compound 3 - enzymes selective for peak 2

| Enzyme | Time | Peak 1 | Peak 2 | Peak 3 | Peak 4 | ee | Peaks | Conversion by TLC |
|---|---|---|---|---|---|---|---|---|
| Lipase PS | 3.5 h | 18.5 | 65.5 | 3.5 | 12.5 | 56% | 2 | ~40% |
|  |  |  |  |  |  | 56% | 4 |  |
|  | 6.5 h | 7.5 | 89.0 | 0.0 | 3.5 | 84% | 2 | >80% |
| Chirazyme L5 | 1 h | 25 | 33 | 27 | 15 | 14% | 2 | ~50% |
|  |  |  |  |  |  | 29% | 3 |  |
|  | 4 h | 20 | 80 | 0 | 0 | 60% | 2 | >80% |
| Chirazyme L9 | 3.5 h | 34.0 | 40.0 | 5.5 | 21.0 | 8% | 2 | ~50% |
|  |  |  |  |  |  | 58% | 4 |  |
|  | 6.5 h | 38.0 | 57.0 | 0.0 | 5.5 | 20% | 2 | >80% |

These results show that Lipase PS is reasonably selective for peak 2.

No reaction was observed with α-Chymotrypsin, Lipase GC, Lipase PGE, Lipase N conc, Lipase G, Lipase R, Lipase M, Lipase A "Amano" 12, Lipase AU miles 1988, Lipase F1 Biocon., Wheat Germ Lipase, Papain W-40, Protease S, Protease X and Pepsin.

Enzymes that gave unselective hydrolysis were Acid Protease II (Newlase II), Bromelain F, Alcalase, Savinase, Esperase, ChiroCLEC-BL, Trypsin, ChiroCLEC-PC, SAWA immobilised *Pseudomonas lipase* and Lipase F. *Candida* Esterase from Altus gave a reaction that was too fast to collect any enantiomeric excess data.

After this screen had been completed, a sample of resolved Compound 3 was prepared by reduction (S)-Compound 1 from a PPL resolution. This was run on the ee/de assay giving peaks 1 and 4. Since the PPL resolution gives (S)-Compound 1, peaks 2 and 3 were needed for the resolution of Compound 3. The results from the screen showed that the majority of enzymes resolved Compound 3 at the acetate centre, not the required butyrate centre. However Lipase AK, Lipase MY, Lipase AY and Lipase PS give the required peaks with reasonable selectivity.

Resolutions of Compound 3 with Lipase PS and Lipase MY were investigated further (Lipase AK has been discontinued by Amano). Scale up and isolation of the product was need to determine if the resolutions were efficient (see Table 12). Lipase PS in toluene gave a 39% yield of recovered starting material with an effective ee of 58% and effective E of 3.7 (this gives a measure of the amount of correct (R)-butyrate that is present in the mixture). These selectivities were no better than what was obtained for Compound 1 with Lipase PS, E=5.3. Further, since in one embodiment, the resolution step is earlier in the reaction sequence, the following examples concentrate on optimizing the resolution of Compound 1.

TABLE 12

Further investigations of resolutions of Compound 3

| Scale/g | Conc. g/l Solvent | Enzyme wt % | Peak 1 | Peak 2 | Peak 3 | Peak 4 | Yield S.M. | Effective ee S.M. | Effective E |
|---|---|---|---|---|---|---|---|---|---|
| 1.4 | 50 MTBE | PS, 3 | 23 | 45 | 13 | 19 | 52% | 16% | 1.6 |
| 1.3 | 50 toluene | PS, 6 | 15 | 65 | 14 | 6 | 39% | 58% | 3.7 |
| 1.3 | 50 MTBE | MY, 5 | 23 | 45 | 13 | 19 | 52% | 16% | 1.6 |
| 1.2 | 50 toluene | MY, 4 | 22 | 28 | 35 | 15 | 42% | 26% | 1.8 |

Conditions: 20° C.,
1:1 solvent:pH 7 buffer

Example 18

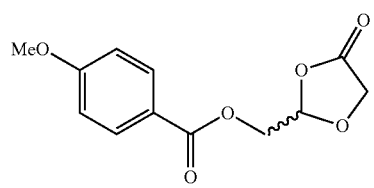

Compound 11

Analytical Development for Compound 11

A chiral assay was required for Compound 11. A baseline separation was achieved by chiral HPLC using the Chiralpak AS column. See FIG. 1C.

HPLC Conditions:

| | |
|---|---|
| Column: | Chiralpak AS |
| Dimensions: | 250 mm × 4.6 mm |
| Mobile Phase: | 1:1 IPA:EtOH |
| Flow Rate: | 0.6 ml/min |
| Detection: | UV 254 nm |

-continued

| | |
|---|---|
| Temperature: | Ambient |
| Retention times: | Peak 1 - 11.96 minutes  Peak 2 - 13.17 minutes |

As this compound was undergoing a microbial screen (>400 samples) as well as a commercial enzyme screen a sub 5 minute run time was required. The previous assay was taken to SFC where this was achieved. See FIG. 1D.

SFC Conditions:

| | |
|---|---|
| Column: | Chiralpak AS |
| Dimensions: | 250 mm × 4.6 mm |
| Mobile Phase: | 95% $CO_2$:EtOH |
| Flow Rate: | 3.0 ml/min, 3000 psi |
| Detection: | UV 254 nm |
| Temperature: | 35° C. |
| Retention times: | Peak 1 - 2.88 minutes  Peak 2 - 3.95 minutes |

Enzyme Screen for Compound 11

Lipases: In a scintillation vial 40 nI, Compound 11, MTBE (5 mL), 50 mM $KH_2PO_4$, pH 6 (5 mL), and ~10 mg enzyme were shaken in an incubator at 30 C. Aliquots were removed periodically and assayed by TLC (50% EtOAc/heptane) and chiral HPLC.

Proteases and esterases: as above, but without MTBE.

Two sets of conditions were used for the screen of Compound 11, the racemic methoxybenzoate ester, depending upon whether the enzyme used was a lipase or a protease/esterase. For lipase-catalysed hydrolyses, the reaction solvent was 1:1 methyl tert-butyl ether (MTBE):50 mM potassium phosphate buffer at pH 6. For protease and esterase-catalysed hydrolyses, reactions were carried out in the phosphate buffer with no immiscible organic co-solvent. Reactions were carried out in scintillation vials in a shaker at 30° C. and followed by thin layer chromatography (TLC). The enantiomeric excess of the residual substrate ($ee_s$ values) was determined by HPLC analysis (Chiralpak AS). The alcohol product from hydrolysis of these esters was known to be unstable from the Example above. Thus with no chiral assay for the product possible, conversions could not be calculated, so it was noted whether any substrate was still present by TLC analysis.

The results from the screens are shown in the tables below. Table 13 shows the results for the enzymes that selectively left the enantiomer corresponding to peak 1 in the chiral HPLC assay, and Error! Reference source not found. the results for the enzyme selective for peak 2.

TABLE 13

Enzymes that selectively leave peak 1 in the HPLC assay

| Enzyme | Time | $ee_s$/% | Comments |
|---|---|---|---|
| Lipase M | 72 hrs | 24 | Peak 1 |
| | 2 weeks | 29 | Substrate present |
| Lipase PS | 72 hrs | 7 | Peak 2 |
| | 2 weeks | 22 | Substrate present |
| Chirazyme-L9 | 72 hrs | 19 | Peak 1 |
| | 2 weeks | 56 | Substrate present |
| Lipase MY | 72 hrs | 7 | Peak 1 |
| | 2 weeks | 21 | Substrate present |
| Lipase DS | 72 hrs | 25 | Peak 1 |
| | 2 weeks | 66 | Substrate present |
| Lipase F-DS | 72 hrs | 52 | Peak 1 |
| | 2 weeks | 80 | Substrate present |
| Lipase F | 72 hrs | 37 | Peak 1 |
| | 2 weeks | 68 | Substrate present |

TABLE 13-continued

Enzymes that selectively leave peak 1 in the HPLC assay

| Enzyme | Time | $ee_s$/% | Comments |
|---|---|---|---|
| Chirazyme-L2 | 18 hrs | 100 | Peak 1 |
| | 2 weeks | 100 | Substrate present |
| Lipase AY | 72 hrs | 31 | Peak 1 |
| | 2 weeks | 69 | Substrate present |
| Lipase A "Amano" 12 | 72 hrs | 16 | Peak 1 |
| | 2 weeks | 45 | Substrate present |
| Lipase N cone | 72 hrs | 33 | Peak 1 |
| | 2 weeks | 46 | Substrate present |
| Lipase AP6 | 72 hrs | 17 | Peak 1 |
| | 2 weeks | 43 | Substrate present |
| Sigma CCL | 72 hrs | 20 | Peak 1 |
| | 2 weeks | 62 | Substrate present |
| Acid Protease A | 48 hrs | 24 | Peak 1 |
| | 2 weeks | 76 | Substrate present |
| Acid Protease DS | 48 hrs | 66 | Peak 1 |
| | 2 weeks | 92 | Substrate present |

TABLE 14

Enzyme that selectively leaves peak 2 in the HPLC assay

| Enzyme | Time | $ee_s$/% | Comments |
|---|---|---|---|
| Lipase PS | 72 hrs | 7 | Peak 2 |
| | 2 weeks | 22 | Substrate present |

The following enzymes were unselective (<20% $ee_s$ either peak): SAWA immobilised lipase; Chiroclec-PC; Protease B; Newlase F; Alcalase; Lipase R; PPL; Lipase G; PLE; Chirazyme-E1; Chirazyme-L5; ChiroCLEC-CR; Protease M; Peptidase R; Acid Protease A-DS; Protease N; Protease A2G; Protease NL; Protease DS; Protease S; Protease P "Amano" 6; Prozyme 6; Proleather; Bromelain-F; Papain W-40 (Amano); Papain (Sigma); Protease X; Protease XXXI; Savinase; Esperase; Pepsin; ChiroCLEC-BL; Choline Esterase; Chirazyme-E2; and α-Chymotrypsin.

Example 19

Scale-Up of Chirazyme-L2 Resolution of Compound 11

During the initial studies of the resolution of Compound 11, it was not known how the enantiomers correlate to the peaks in the chiral HPLC assay. In order to determine the absolute configuration, a sample was taken through the entire synthetic sequence to a DAPD intermediate where the configuration could be determined One of the most promising enzymes from the screen was Chirazyme-L2; thus this reaction was scaled up in order to prepare a sample (Scheme 12). The substrate concentration was increased to 20 g/L and the enzyme loading reduced, but otherwise optimization of the process was minimal With a 1 g input of racemate, 5 wt. % Chirazyme-L2 at 30° C. with the pH maintained between 5 and 6, 0.321 g (32%) of ester was obtained in >98% ee and good purity.

Scheme 12: Scale-up of Compound 11 resolution

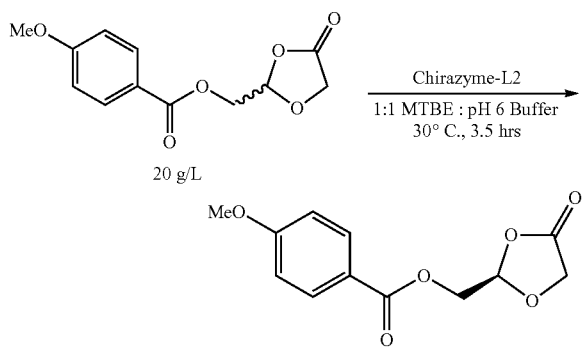

The reaction was scaled-up further to 10 g; after 3.5 h, 3.9 g of Compound 11 was obtained in 39% yield, >99% ee as a white solid. This was determined to be the undesired (S)-enantiomer. Consequently the desired (R)-enantiomer must correspond to peak 2 in the chiral HPLC assay.

Therefore, a 500 mL jacketed vessel at 30° C. was charged with MTBE (250 mL), racemic Compound 11 (10.00 g, 39.7 mmol, TP-43/100) and 50 mM $KH_2PO_4$, pH 6 (250 mL). Chirazyme-L2 (500 mg, 5 wt. %) was added to the mixture with stirring. The pH was maintained between pH 5 and 6 by addition of 2N NaOH. After 3.5 hours, the base uptake had stopped, and the mixture filtered through Celite° and separated. The aqueous was extracted with MTBE (2×200 mL), the organic layers were combined, washed with 2N NaOH (200 mL), sodium sulfite (200 mL), 2N HCl (200 mL) and dried ($MgSO_4$). Concentration in vacuo gave Compound 11 as a white solid. Yield 3.89 g, 39%; ee>99%; $^1$H NMR (400 MHz, $CDCl_3$) consistent with structure.

Example 20

Scale-up of Lipase PS Resolution of Compound 11

From the initial screen, only Lipase PS was a candidate to give the desired (R)-enantiomer of Compound 11 (see Error! Reference source not found.). This resolution was scaled up to 2 g in order to determine its selectivity. At approximately 50% conversion the enantiomeric excess of residual ester was only 8%. The enzyme is clearly not sufficiently selective for a viable process.

A 100 mL jacketed vessel at 30° C. was charged with MTBE (25 mL), racemic Compound 11 (2.00 g, 7.94 mmol, TP-43/100) and 50 mM $KH_2PO_4$, pH 6 (25 mL). Lipase-PS (100 mg, 5 wt. %) was added to the mixture with stirring. The pH was maintained between pH 5 and 6 by addition of 2N NaOH. At approximately 50% conversion (by base uptake), an aliquot was taken and analysed to be 8% ee. After a further 24 hours no substrate was detected.

Example 21

Microbial Enzyme Screen

General Procedure for Preparing 96 Well Culture Plates.

2.2 mL 96 deepwell plates were used. 1.0 mL sterile TSB (Tryptone soya broth, Oxoid CM129) for bacteria, or YM (Yeast mould broth, Oxoid CM920B) for yeasts, was added per vial and inoculated with a stock of culture. The plates were shaken at 25° C. for 48 hours. The cell pellets were harvested by centrifugation (1000 g for 10 minutes at 4° C.) and the supernatant removed. The cell pellets were stored at −20° C. until required for screening.

Screening of 96 Deepwell Culture Plates on Compound 11.

A 200 g/L stock solution of Compound 11 was prepared in acetone. 450 µL 0.1M Tris-HCl+0.1% Tween 80, pH 7.0 and 50 µl Compound 1 stock solution were added per well of the 96 deepwell culture plate. These plates were shaken at 25° C. for 72 hours. Samples were extracted into MTBE and assayed by chiral HPLC.

The screen was carried out against a range of bacteria and yeasts. These were grown up in 96 deep-well plates and their cell pellets harvested by centrifugation. This enables the pellets to be re-suspended in buffer with substrate for the screen. The plates were shaken at 25° C. for 72 hours. Samples were extracted into MTBE and assayed by chiral HPLC. The results from the screen are summarized in FIG. 3C. Several hits were identified as selective for leaving the enantiomer corresponding to peak 1 in the assay, however only a few strains gave the desired enantiomer (peak 2) at a low ee. This may be due to the low levels of enzyme expressed in the wild type micro-organisms, and hence low conversion. It must also be noted that the high throughput chiral HPLC method used can only give approximate values. The best results are collated in Table 15.

TABLE 15

Microbial screen of Compound 11

| CMC No | Strain | Substrate ee/% | Selectivity* |
|---|---|---|---|
| 103522 | Unidentified | 23 | Peak 2 |
| 103978 | Lactobacillus plantarum | 12 | Peak 2 |
| 103947 | Comamonas acidovorans | 11 | Peak 2 |
| 103826 | Bacillus licheniformis | 10 | Peak 2 |
| 103397 | Pseudomonas sp. | 10 | Peak 2 |
| 103308 | Phaffia rhodozyma | 63 | Peak 1 |
| 103115 | Rhodococcus sp. | 61 | Peak 1 |
| 103188 | Pseudomonas putida | 58 | Peak 1 |
| 103126 | Enterobactericae sp. | 44 | Peak 1 |

*major peak of residual ester in HPLC chromatogram.

The five strains that gave peak 2 selectively and three that gave peak 1 were selected for further trials to confirm the results from the initial screen; the results are shown in Table 16. Only CMC 103522, the best candidate for peak 2 from the primary screen, confirmed its selectivity at ≦10% ee Peak 2.

TABLE 16

Re-screen of strains against Compound 1

| CMC No | Strain | Substrate ee/% | Selectivity* |
|---|---|---|---|
| 103115 | Rhodococcus sp. | 5 | Peak 1 |
| 103126 | Enterobactericae sp. | 2 | Peak 1 |
| 103188 | P. putida | 5 | Peak 1 |
| 103397 | Pseudomonas sp. | 1 | Peak 1 |
| 103522 | Unidentified | 9 | Peak 2 |
| 103826 | B. lichenformis | 4 | Peak 1 |
| 103947 | C. acidovorans | 2 | Peak 1 |
| 103978 | L. planatarum | 2 | Peak 1 |

*major peak of residual ester in HPLC chromatogram.

Example 22

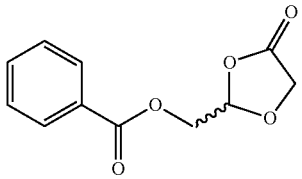

Compound 12

Analytical Development for Compound 12

A chiral assay was also required for Compound 12. See FIG. 1E. Details of the assay conditions are as follows:

HPLC Conditions:

| | |
|---|---|
| Column: | Chiralpak AS |
| Dimensions: | 250 mm × 4.6 mm |
| Mobile Phase: | 1:1 IPA:EtOH |
| Flow Rate: | 0.8 ml/min |
| Detection: | UV 254 nm |
| Temperature: | Ambient |
| Retention times: | Peak 1 - 6.91 minutes    Peak 2 - 7.66 minutes |

Again this assay was taken to SFC to achieve a sub 5 minute run time to allow the large number of microbial screen samples to be analyzed in as short a time as possible. See FIG. 1F.

SFC Conditions:

| | |
|---|---|
| Column: | Chiralpak AS |
| Dimensions: | 250 mm × 4.6 mm |
| Mobile Phase: | 95% $CO_2$:EtOH |
| Flow Rate: | 3.0 ml/min, 3000 psi |
| Detection: | UV 254 nm |
| Temperature: | 35° C. |
| Retention times: | Peak 1 - 3.06 minutes    Peak 2 - 3.81 minutes |

Enzyme Screen.

Compound 12 was screened against the 96 well culture plates. The screen for Compound 12 was based on that developed for Compound 11, but limited to only ten enzymes. Two sets of conditions were used, depending upon whether the enzyme was a lipase or a protease/esterase. For lipase-catalyzed hydrolyses, the reaction solvent was 1:1 MTBE:50 mM potassium phosphate buffer at pH 6. For protease and esterase-catalyzed hydrolyses, reactions were carried out in the phosphate buffer with no immiscible organic co-solvent. In all reactions the amount of substrate utilized was 40 mg. Reactions were carried out in a shaker bath at 30° C. and enantiomeric excess values determined by HPLC analysis (Chiralpak AS). The three positive results are summarized in Table 17.

TABLE 17

Commercial enzyme screen of Compound 2

| Enzyme | Time | $ee_s$/% | Comments |
|---|---|---|---|
| Chirazyme-L2 | 20 hrs | 95 | Peak 2 |
| | 1 week | 100 | Substrate present |
| Acid Protease DS | 20 hrs | 47 | Peak 2 |
| | 1 week | — | No substrate |

TABLE 17-continued

Commercial enzyme screen of Compound 2

| Enzyme | Time | $ee_s$/% | Comments |
|---|---|---|---|
| Chirazyme-L9 | 20 hrs | 8 | Peak 2 |
| | 1 week | 25 | Substrate present |

The following enzymes gave less selective resolutions with Compound 2 (<20% $ee_s$): Lipase F-DS; Lipase PS; Lipase DS; Lipase AY; Lipase F; Acid Protease A; and Lipase N Cone.

Samples were assayed by chiral HPLC; the results are summarized in FIG. 3D. As can be seen from FIG. 3D, microbial strains were identified that are selective for both enantiomers. The conversions, and therefore the true selectivities are unknown. While Chirazyme-L2 was identified as an excellent enzyme for leaving the enantiomer corresponding to peak 2 in the HPLC assay, no enzymes were identified in this limited screen that left peak 1. It is not known which peak in the chiral assay for Compound 2 corresponds to the required (R)-enantiomer.

Example 23

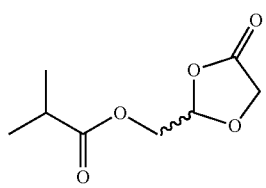

Compound 13

Chemical Determination of Configuration

As an expedient way of determining which of the peaks in the GC chromatogram correspond to the desired enantiomer, it was envisioned that authentic samples could be made from the silyl ether. The enantiomerically enriched silyl ether was heated with 2-methylpropanoyl chloride in tetrahydrofuran (THF) with tetrabutylammonium fluoride (TBAF) (see Scheme 13).

Scheme 13: Determination of configuration for Compound 13

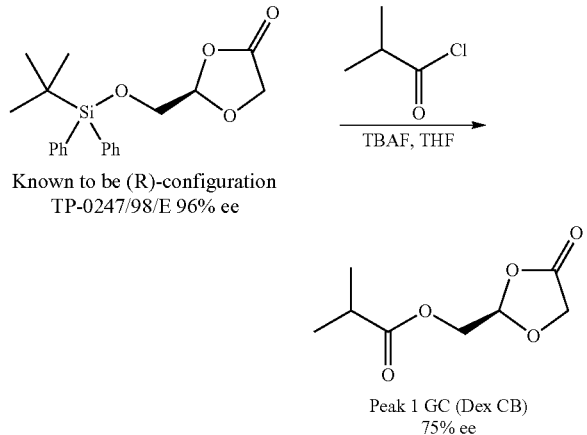

Known to be (R)-configuration
TP-0247/98/E 96% ee

Peak 1 GC (Dex CB)
75% ee

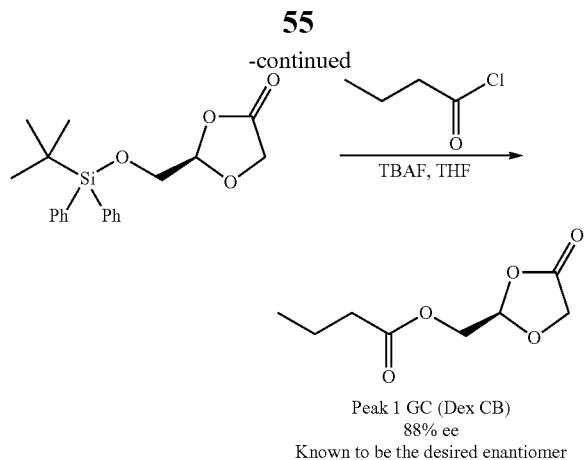

Peak 1 GC (Dex CB)
88% ee
Known to be the desired enantiomer

The goal was to cleave the silyl ether and trap the generated alcohol in situ with acid chloride. Although the intermediate alcohol is unstable, if only a small fraction reacts with acid chloride faster than decomposing, then ester of known configuration would be generated. Since the chiral assay is a GC method, the sensitivity is high and minute quantities can be detected. Starting from (R)-silyl ether, peaks were observed in the GC chromatograms for the product, enhanced in peak 1 in both cases. Spiking the samples with racemate confirmed that the peaks corresponded to the desired esters. Slight losses in enantiomeric excess were observed in both cases, possibly due to the acidity of the medium and the potential instability of the parent alcohol that is assumed to be an intermediate. The absolute configuration of the starting silyl ether is known to be the desired (R)-configuration. The enantiomer that gives peak 1 in the GC assay for the n-butanoate ester is also known to be the required enantiomer. Therefore, the reaction of the (R)-silyl ether with 2-methylpropanoyl chloride will give the required enantiomer of Compound 13, and that this corresponds to peak 1 in the GC assay. Since the other enantiomer of the silyl ether was available, for extra confirmation it was also demonstrated to give the peak 2 enantiomer in reaction with 2-methylpropanoyl chloride.

Experimental

Procedure for Preparation of Esters from Enantiomerically Silyl Ether

A mixture of 150 mg of silyl ether, 0.5 mL of acid chloride and 0.4 mL of TBAF (1M in THF), in 5 mL of THF, was heated to reflux under nitrogen for 3-4 hours. TLC showed a small amount of product formed. An aliquot was taken, passed through a plug of silica and analysed by chiral GC.

Example 24

Analytical Development for Compound 13

A chiral GC assay was developed to separate the enantiomers of Compound 13. See FIG. 1G. Details of the assay conditions are as follows:
GC Conditions:

| Column: | Chirasil DEX CB |
| Dimensions: | 25 m × 0.25 mm |
| Temp. Program: | 140° C. for 8 minutes then to 200° C. at 15° C./min |
| Carrier gas: | Helium @ 20 psi |
| Detection: | FID @ 200° C. |
| Retention times: | Peak 1 - 6.5 minutes  Peak 2 - 6.8 minutes |

In addition, an achiral GC assay was developed to determine the purity of Compound 13. See FIG. 1H. Details of the assay conditions are as follows:
GC Conditions:
Column: J&W Scientific DB5
Dimensions: 15m×0.25 mm
Film thickness: 0.25 μm
Temp. Program: 40° C. for 5 minutes then to 200° C. at 10° C./min
Carrier gas: Helium @ 12 psi
Detection: FID @ 200° C.
Retention time Compound 3-17.80 minutes
Enzyme Screen Stability of the n-butanoate ester was determined to be significantly better at pH 6. Therefore for the screening of the sec-butanoate ester, Compound 13, similar conditions were used. Racemic Compound 13 was screened for enzymatic hydrolysis with commercially available lipases, proteases and esterases. All lipase reactions were carried out in the presence of 40 μL Compound 13, 5 mL MTBE, 5 mL pH 6 phosphate buffer and 20 wt. % enzyme. Esterase and protease reactions were performed without MTBE present. The mixtures were shaken in an incubator at 30° C. and monitored by TLC and Chiral GC. The alcohol product, like the other esters, is unstable as previously described. Therefore no chiral assay for the product was possible and conversions could not be calculated. For the screen it was noted whether any substrate was still present by TLC analysis. The best results from the screens are shown in Table 18 below.

TABLE 18

Commercial enzyme screen of Compound 13

| Enzyme | Time | ee$_s$/% | Comments |
|---|---|---|---|
| Chirazyme-L2 | 1 hr | 81 | Peak 1 |
|  | 5 hrs | — | Not enough substrate remaining |
| Lipase F-DS | 1 hr | 10 | Peak 1 |
|  | 1 week | 46 | Substrate present |
| Acid Protease DS | 24 hrs | 49 | Peak 1 |
|  | 120 hrs | — | Not enough substrate remaining |
| Lipase PS | 5 hrs | 44 | Peak 1 |
|  | 24 hrs | — | Not enough substrate remaining |
| Chirazyme L9 | 24 hrs | 42 | Peak 1 |
|  | 120 hrs | — | Not enough substrate remaining |
| Acid Protease A | 24 hrs | 23 | Peak 1 |
|  | 120 hrs | — | No substrate |
| Lipase M | 24 hrs | 28 | Peak 1 |
|  | 1 week | 30 | Substrate present |
| Protease M | 5 hrs | 19 | Peak 1 |
|  | 1 week | 30 | Not much substrate present |
| Protease P | 24 hrs | 21 | Peak 1 |
| "Amano" 6 | 1 week | 33 | Not much substrate present |

The following enzymes gave less selective reactions with Compound 13 (<20% ee$_s$): Lipase DS; Lipase AY; Lipase F; Lipase N Cone; SAWA immobilised lipase; Chiroclec-PC; Lipase MY; Protease B; Newlase F; Alcalase; Lipase R; PPL; Lipase G; PLE; Chirazyme-E1; Lipase A "Amano" 6; Lipase A "Amano" 12; Lipase AP6; Sigma CCL; Chirazyme-L5; ChiroCLEC-CR; Peptidase R; Acid Protease A-DS; Protease N; Protease A2G; Protease NL; Protease DS; Protease S; Prozyme 6; Proleather; Bromelain-F; Papain W-40 (Amano); Papain (Sigma); Protease X; Protease XXXI; Savinase; Esperase; Pepsin; ChiroCLEC-BL; Chirazyme-E2; and α-Chymotrypsin.

From Table 19 it can be seen that all the enzymes selectively left peak 1 in the chiral GC assay, fortunately corresponding to the desired enantiomer. None of the enzymes screened were selective for peak 2. Four enzymes were chosen for re-screening with lower loadings, the results of which can be seen in Table. The most promising of these was Chirazyme-L2, leaving residual ester in 90% ee after 5.5 hours.

TABLE 19

Re-screen of peak 1 selective enzymes for Compound 3

| Enzyme | Time | ee$_s$/% | Comments |
|---|---|---|---|
| Chirazyme-L2 | 1 hr | 21 | Peak 1 |
| | 5.5 hrs | 90 | Substrate present |
| Lipase PS | 16 hrs | 65 | Peak 1 |
| | 24 hrs | — | No substrate |
| Acid protease DS | 24 hrs | 42 | Peak 1 |
| | 48 hrs | 47 | Not much substrate remaining |
| Chirazyme-L9 | 24 hrs | 21 | Peak 1 |
| | 72 hrs | 64 | Substrate present |

Example 25

Scale-up of Chirazyme-L2 Resolution of Compound 13.

The Chirazyme-L2 resolution was scaled up to 1 g, 30 mg of enzyme and 25 mL each of pH 6 phosphate buffer and MTBE. After work-up the reaction yielded 0.212 g, 21% Th of Compound 13 as a colorless oil. The $^1$H NMR spectrum showed a significant amount of impurities present, which had been carried through from the substrate.

On a 6 g scale, using the same conditions, at 20° C. the yield was 1.52 g, 25% Th of 88% ee resolved Compound 3 as a pale yellow oil. Again $^1$H NMR indicated some impurities were present. The selectivity was improved at a lower temperature, 0° C. Starting from 5.25 g of racemate, after 4.5 hours the resolution yielded 1.48 g, 28% Th of 92% ee Compound 3. The configuration was confirmed as the required (R)-enantiomer.

Initially the bioresolution was performed at a moderate concentration, 20 g/L. To study the effect of increasing the volume efficiency, the resolution was repeated on a 1 g scale at 50 g/L, 0° C. in pH 6 phosphate buffer and MTBE. After 4.5 hrs, the biotransformation yielded 0.44 g, 44% Th, of material as a pale yellow oil in 92% ee. From this it was concluded that the volume efficiency could be improved with no significant loss in selectivity.

The purity of product obtained from these processes was low. Several impurities were carried through from the racemate. For a bioresolution of moderate selectivity the conversion optionally can be increased to gain high enantiomeric purity of residual ester. One of the impurities, the 2-methylpropanoate ester of hydroxyacetaldehyde shown in Scheme 14, was present in the racemate. However it was not clear whether this was also produced in the bioresolution, as outlined below.

Scheme 14: Formation of impurities

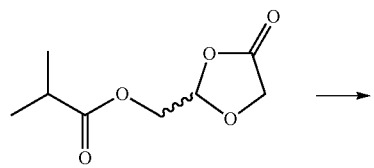

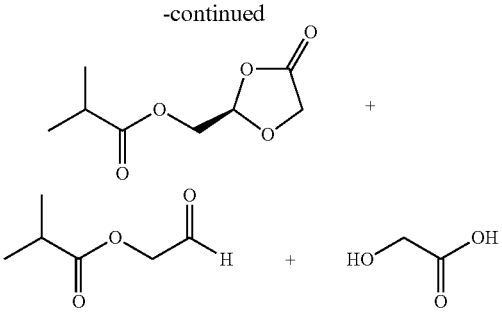

In order to determine if any additional aldehyde was generated during the biotransformation, the resolution was repeated on the same scale (1 g) using distilled lactone, which contained no of aldehyde. This reaction yielded 0.29 g, 29%, of 93% ee product. The $^1$H NMR spectrum showed that the aldehyde was present; clearly this material is produced during the reaction or work up.

Changing the solvent to toluene resulted in a slower, but more selective resolution. On a 1 g scale at, 50 g/L, the reaction was worked-up after 22.5 hours to give 0.30 g, 30% yield of >99% ee ester. The concentration was further increased to 200 g/L, using 4 g of racemate, in 10 mL each of pH 6 phosphate buffer and toluene, at 0° C. The process was highly volume efficient, and no problems were encountered. After 17 hours the biotransformation yielded 1.11 g, 28%, of 95% ee product.

Several reactions were performed on a slightly larger scale (2-10 g) utilizing differing enzyme loadings and reaction times; the results are summarized in Table 0 below. The rate of reaction was not entirely predictable. Several factors may be responsible for this, including different batches of racemate with different impurity profiles and differences in mixing of the biphasic solvent-immobilized enzyme system. The yields may be misleading due to impurities carried though from the racemate. It was found on this scale that thiosulfate, bicarbonate and acidic washes did not significantly reduce the amount of the aldehyde impurity. The work-up procedure required some clarification, but at this stage it was hoped that a combination of suitable wash and Kugelrohr distillation (wiped-film on scale) after resolution would be effective. This was investigated later on a larger scale. All these biotransformations used the toluene-buffer biphasic system at 200 g/L.

TABLE 20

Chirazyme-L2 resolution of Compound 3

| Entry | Enzyme Loading/wt. % | Scale/g | Time/hours | Yield/% | ee/% |
|---|---|---|---|---|---|
| 1 | 1 | 4 | 112 | 19 | 98 |
| 2 | 2 | 8 | 16 | 22 | 73 |
| 3 | 2 | 2 | 47 | 29 | 93 |
| 4 | 2.5 | 10 | 15 | 20 | >99 |
| 5 | 10 | 10 | 4 | ND | 96 |

The process was scaled-up to 30 g using 10 wt. % enzyme at 0° C., 200 g/L. After a Kugelrohr distillation 4.2 g of >95% ee ester was recovered.

As discussed earlier, the purity of the racemate is vital to the quality and yield obtainable after biotransformation. Moreover it is difficult to determine the true selectivity of a resolution with accurate conversion. This is unavailable from enantiomeric excess data since the product of the bioresolution cannot be isolated; the only information available is the enantiomeric excess of the residual substrate. An idea of selectivity is gained from the yield of the ester, but as it is contaminated with impurities, the accuracy is in doubt.

When considering the final process it may be advantageous to use a crude racemate and purify after bioresolution, e.g. by wiped-film distillation. However, impurities may inhibit the enzyme. The possibility of one such process using very crude substrate was investigated; a mixture of racemate containing DME, water and other impurities, containing approximately 1 g of substrate was used in the bioresolution. During the biotransformation no base was consumed and so additional enzyme added. An aliquot was removed after 16 hours and found to be racemic. These findings would suggest that the enzyme was being "killed" by the impurities present in this mixture. Thus, in one embodiment, purification of the substrate is preferable prior to bioresolution.

Example 26

Biotransformation in 2-Propanol-Water

As mentioned earlier the stability of the substrate was a potential problem. A background process in which lactone is opened to glycolic acid and the 2-methylpropanoate ester of hydroxyacetaldehyde cannot be ruled out (Scheme 15).

Scheme 15: Ring-opening of lactone

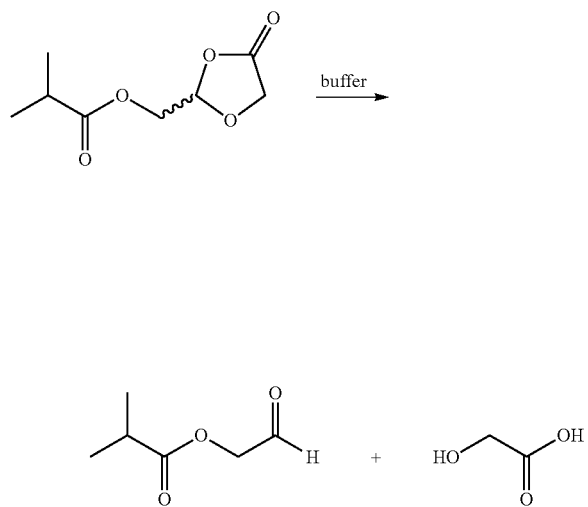

The mode of action of the enzyme on Compound 13 is also unknown. The only products detected after bioresolution are the 2-methylpropanoate ester of hydroxyacetaldehyde and glycolic acid. However the usual mode of action for a lipase is to hydrolyse the ester; this would give the lactone and 2-methylpropionic acid (Scheme 16). The lactone alcohol product is not detected and breaks down to glycolic acid and hydroxyacetaldehyde. If this mechanism is correct then the esterified aldehyde must come from reaction of hydroxyacetaldehyde with 2-methylpropionic acid. An alternative mechanism is that the enzyme may act directly to open the lactone without first cleaving the ester. This mode of action whereby a lactone ring is opened has been observed for liver esterases (see for example: E. Fouque and G. Rousseau *Synthesis* 1989, 661; and P. Barton and M. I. Page *J. Chem. Soc., Perkin Trans.* 2, 1993, 2317), but is perhaps unlikely in this case.

Scheme 16: Possible reaction mechanism

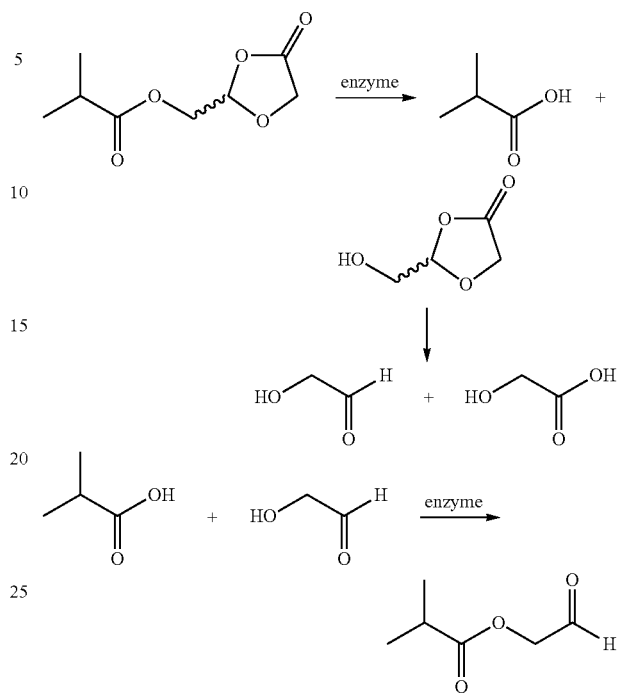

The use of additives in biotransformations has been widely reported to enhance selectivities, but their effects on enantiomeric excess are usually unpredictable. See for example: T. V. Hansen, V. Waagen, V. Partali, H. W. Anthonsen and T. Anthonsen, *Tetrahedron Asymmetry* 1995, 6, 499; G. Duan and J. Y. Chen, Biotechnology Letters 1994, 16, 1065; N. W. Boaz and R. L. Zimmerman, *Tetrahedron Asymmetry* 1994, 5, 153; and K. Faber, G Ottolina and S. Riva, *Biocatalysis* 1993, 8, 91. The mode of action is also often unclear; the additive may be acting as a phase transfer catalyst, as an enzyme modifier, or as an alternative to water as a nucleophile. In the resolution of (−)-2',3'-dideoxy-5-fluoro-3'-thiacytidine (FTC, also known as Coviracil™ and emtricitabine), it was found that alcohol:water mixtures were a good alternative to the normal biphasic or mainly aqueous systems. It was envisioned that this might also be effective in the resolution of Compound 13, both with respect to enzyme selectivity and substrate stability. This hypothesis was tested using 1 g of Compound 13, with 3 wt. % enzyme, at 100 $gL^{-1}$ in an 8:2 2-propanol:water solvent system. After 47 hours the reaction yielded 0.47 g, 47% Th, of >98% ee material.

The initial result in 2-propanol-water looked excellent, although water and aldehyde may have bolstered the yield. More meaningful results were gained on a larger scale, with distillation to purify the product. The racemate was distilled using wipe film distillation. The conditions were 30 g of racemate in 9:1 2-propanol (IPA)-water, at 200 $gL^{-1}$ with an enzyme loading of 5 wt. %. This reaction was filtered after 10 hours and reduced in vacuo. The enantiomeric excess was determined to be 94%. This material was divided into two batches to investigate purification methods. The first portion was distilled using Kugelrohr apparatus at 133° C./1.3 Torr to give two required fractions:

Fraction 1: 10.8 g contained 61% aldehyde, 31% Compound 3 and an undetermined amount of glycolic acid. Further distillation at 80° C./4-5 Torr to remove the aldehyde and a water wash gave 4.4 g of Compound 390% pure material containing 4% aldehyde.

Fraction 2: 2.7 g contained no aldehyde but a significant amount of glycolic acid and Compound 3. After a water wash, 1.8 g of Compound 3 was obtained, 91% pure (by GC).

The second portion of crude material was given a water wash prior to distillation at 140° C./1.6 Torr followed by removal of the aldehyde at 60° C./1.6 Torr, yielding 5.2 g of material in 89% purity, containing 6% aldehyde.

Therefore in total 11.4 g of the 2-methylpropanoate ester was produced in 90% purity, 94% ee, corresponding to an excellent 38% overall yield. This procedure clearly out-performs that with toluene:buffer and with further optimization could provide an efficient route to the optically pure lactone.

Example 27

Experimental

Resolution of 30 g of Compound 13 with Chirazyme-L2 in 2-propanol:water

A 500 mL jacketed vessel at 0° C. was charged with 2-propanol (135 mL), water (15 mL), and racemic Compound 13 (30 g, DB/1005/85/1). The mixture was stirred and Chirazyme-L2 (1.5 g, 5 wt. %), added to this mixture. The $ee_s$ was measured at intervals by removing aliquots of solution, extracting with ethyl acetate, drying (MgSO$_4$), and analysing by chiral GC. After 10 h, the $ee_s$ was 93%. Shortly after the mixture was filtered through Celite° and concentrated in vacuo to give 32.1 g of crude Compound 3 as a pale yellow oil. The oil was then dissolved in toluene and concentrated (2×250 mL) to remove any water azeotropically. Crude yield 29.4 g, 98%; ee 94%.

This oil was divided into two portions. The first was distilled using Kugelrohr apparatus at 133° C./1.3 Torr, which gave three fractions overall. Fraction 1 (most volatile) contained 10.8 g of 61% aldehyde, 31% lactone and 8% of other impurities. Fraction 2 contained 2.7 g of lactone contaminated with a significant amount of glycolic acid and fraction 3 contained yellow low volatility impurities. Fraction 2 was dissolved in toluene (200 mL), washed with water (200 mL), dried (MgSO$_4$) and concentrated in vacuo to give 1.8 g of Compound 13 as a colourless oil in 91% purity by GC (no aldehyde observed). Most of the aldehyde in fraction 1 was then removed by Kugelrohr distillation at 80° C./4-5 Torr to give, as the residue, 6.1 g of lactone containing ~12% aldehyde and an undetermined amount of glycolic acid. This material was then dissolved in toluene (200 mL), washed with water (200 mL), dried (MgSO$_4$) and concentrated in vacuo to give 4.4 g of Compound 3 as a colourless oil in 90% purity, 4% aldehyde by GC.

The second portion of material was dissolved in toluene (200 mL), washed with water (200 mL), dried (MgSO$_4$) and concentrated in vacuo. The resulting oil was then distilled using Kugelrohr apparatus at 140° C./1.6 Torr, to remove low volatility impurities, and then further distilled at 60° C./1.3 Torr to remove any residual aldehyde. The material recovered from this distillation was determined to be 5.15 g of 89% purity, 6% aldehyde by GC.

Overall yield: 11.4 g, 38%; GC Purity: 90%

Example 28

Microbial Enzyme Screen.

As for Compounds 11 and 12, Compound 13 was screened against 96 well culture plates. Samples were assayed by chiral GC; it must be noted that the high through put chiral GC method used can only give approximate values. The results of the screen are represented in FIG. 3E.

A large number of strains showed activity on Compound 13, with selectivities for both peaks 1 and 2 observed in the GC chromatograms. Those that gave an enantiomeric excess >40% ee are shown in Table 21.

TABLE 21

Microbial Screen of Compound 13

| CMC No | Strain | Substrate ee/% | Comments |
|---|---|---|---|
| 103127 | *Serratia liquifaciens* | 42 | Peak 1 |
| 103869 | Unidentified | 44 | Peak 1 |
| 103355 | Unidentified | 54 | Peak 1 |
| 103032 | *Bacillus licheniformis* | 43 | Peak 1 |
| 103063 | Unidentified | 74 | Peak 1 |
| 103071 | Unidentified | 75 | Peak 1 |
| 103095 | *Nocardia* sp. | 54 | Peak 1 |
| 103134 | Unidentified | 48 | Peak 1 |
| 103146 | *Pseudomonas* sp. | 46 | Peak 1 |
| 103188 | *Pseudomonas putida* | 46 | Peak 2 |
| 103322 | *Pseudomonas alcaligenes* | 70 | Peak 1 |
| 103419 | *Acinetobacter* sp. | 81 | Peak 1 |
| 103422 | Unidentified | 79 | Peak 1 |
| 103423 | Unidentified | 71 | Peak 1 |
| 103669 | Unidentified | 51 | Peak 1 |
| 103777 | Unidentified | 50 | Peak 1 |
| 103780 | *Streptomyces* sp. | 49 | Peak 1 |
| 103405 | Unidentified | 62 | Peak 1 |
| 103785 | *Pseudomonas fluorescens* | 87 | Peak 1 |
| 103869 | Unidentified | 92 | Peak 1 |
| 103331 | *Candida rugosa* | 40 | Peak 1 |
| 103587 | *Staphylococcus* sp. | 65 | Peak 1 |
| 103774 | *Streptoverticillium cinnamoneus* | 87 | Peak 2 |

From the results of the primary screen those strains that showed the best selectivity for peak 1 and good peak area were re-screened. The strains which reconfirmed their activities are shown in Table 22.

TABLE 22

Re-screen of strains against Compound 3

| CMC No | Strain | Substrate ee/% |
|---|---|---|
| 103063 | Unidentified | 45 |
| 103127 | *S. liquifaciens* | 41 |
| 103373 | *Acinetobacter* sp. | 41 |
| 103419 | *Acinetobacter* sp. | 14 |
| 103552 | Unidentified | 31 |
| 103606 | *Acinetobacter junii* | 21 |
| 103635 | Unidentified | 44 |
| 103661 | *S. cerevisiae* | 47 |
| 103777 | Unidentified | 18 |
| 103869 | Unidentified | 65 |

Example 29

Scale-up of Biotransformations for CMC 103869 & 103661.

From the screen, two strains were selected for scale-up. These were CMC 103869 (Unidentified) and CMC 103661 (*S. cerevisiae*). Cultures of both were grown up and their harvested cell pastes stored at −20° C. Biotransformations were set-up at 30 mL scale, using both pH and temperature control. Initial biotransformations were in 0.1M Tris-HCl, pH 7. Poor enantiomeric excesses and substrate stability were observed, possibly due to the high pH. Lowering the pH to 6 partially increased selectivity, but there were still substrate stability problems. A change in buffer to 50 mM KH$_2$PO$_4$, pH 6, further increased the enantiomeric excess. The results for both strains are summarized in FIG. 4. Resolution of Compound 13 with CMC 103869 gave residual ester of 70% ee. The results with CMC 103361 were disappointing and therefore further studies with this strain were abandoned. For all the biotransformations a loss of residual substrate was observed, possibly due either to a second enzyme or poor substrate stability at 25° C. Finally by reducing the temperature to 10° C. the selectivity increased to ≧95% ee, however there was still a total loss of substrate over time. The conversion and hence absolute selectivity is not known.

CMC 103869 was grown up in TSB media and CMC 103661 was grown up in YM media in flasks. Both strains were grown at 25° C. and cells harvested by centrifugation (2000 g for 20 minutes at 4° C.). Cell pastes were stored at −20° C. Biotransformations were run in 200 mL jacketed vessels with a magnetic stirrer, with temperature and pH control (with 1N NaOH). Cell pastes were re-suspended at 10% w/v in either 0.1M Tris-HCl buffer (adjusted to the required pH), or 50 mM $KH_2PO_4$, pH 6. Substrate, buffer and cell paste were added to the vessel and samples taken for analysis by chiral GC by dilution into MTBE.

Example 30

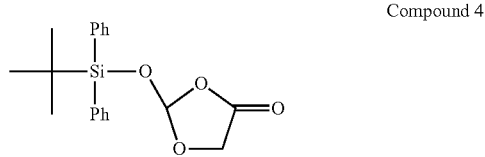 [SMILES: CC(C)(C)[Si](OC1OCC(=O)O1)(c1ccccc1)c1ccccc1]

Compound 4

Analytical Development for Compound 4

The conditions for the chiral assay HPLC method of analysis was reproduced to give the resolution shown in the chromatogram below:

HPLC Conditions:
Column: Chiralcel OJ
Dimensions: 250×4 6 mm
Mobile phase: 85% Heptane
15% EtOH
Flow rate: 1.0 mL/min
Detection: UV @ 254 nm
Retention times: 1—7.47 minutes
2—11.16 minutes Under the assay conditions the peak shapes of the enantiomers were a little broad (FIG. 1K), thus an attempt was made to improve this assay. This was achieved by employing supercritical fluid chromatography (SFC), with both isomers giving sharp peaks that were fully resolved within 4 minutes. See FIG. 1L.

Optimized SFC Conditions:
Column: Chiralcel OJ (250×4 6 mm)
Mobile phase: 95% $CO_2$, 5% MeOH
Flow rate: 3.0 mL/min
Pressure: 3000 psi
Column temp.: 35° C.
Retention times: 1—2.73 minutes [(−)-enantiomer]
2—3.28 minutes [(+)-enantiomer]

Bioresolution of Compound 4

During the study of the biotransformation of Compound 1, it was discovered that the material was susceptible to non-enzymatic hydrolysis. This could be due to the high lability of Compound 1 towards hydrolysis and the instability of the postulated lactone-alcohol product, that a possible pathway for the biotransformation was opening of the lactone before saponification of the butyrate. If this was true then enzymatic resolution Compound 4 might be possible. Therefore the reactivity of Compound 4 was tested with lipases PS, PPL, M, MY and the SAWA immobilized lipase, in toluene-pH 7 buffer at 20° C. No reaction was observed (TLC, 24 hours). The enzymatic reaction probably proceeds by first cleavage of the butyrate and then possible lactone opening.

Conglomerate Studies

The IR spectra of the racemate and single enantiomer of Compound 4 were compared and found to be similar but not identical.

The melting points of each of these compounds were then determined by differential scanning calorimetry (DSC) and found to give an onset of melting of 91.7° C. for the racemate and 81.1° C. for the (−)-enantiomer (98.7% ee). Comparison of these melting points reveals that the racemate has a higher melting point than the single enantiomer. For a compound to be a conglomerate the IR spectra of the racemate and single enantiomer must be identical and the melting point of the racemate is required to be the lowest point on the phase diagram. Therefore, this compound is clearly not a conglomerate.

Subsequently, a phase diagram for Compound 4 was constructed. The position of the eutectic was determined, above which point the ee of this compound may be enhanced to enantiomeric purity by crystallization. This phase diagram information was to be obtained by analyzing the melting points (again by DSC) of samples of differing enantiomeric excess in 10% ee increments. These samples were initially prepared by dissolving the required amounts of racemate and single enantiomer in acetone and removing the solvent. This method was successful for the 10% ee, 80% ee and 90% ee samples, with the DSC traces containing just one peak. For all the other samples however, two peaks were observed by DSC (possibly due to polymorphs). A number of methods for producing these samples were attempted to combat this problem. These included melting the sample; dissolving in acetone and heat O/N at 65° C.; melting and heating overnight at 65° C. and using dichloromethane as the solvent; but the DSC still gave two peaks. Therefore the phase diagram/eutectic could not be determined via this method. In addition since the compound was extremely soluble and only 1 g of the racemate and each of the single enantiomers was available, solubility studies were ruled out. However, since only one peak was given by the racemate and single enantiomer samples by DSC, the melting points and enthalpy values for these samples could be determined. This allowed the phase diagram to be constructed theoretically (J. Jacques, A. Collet and S. H. Wilden, *Enantiomers, Racemates and Resolutions*, New York: Wiley, 1981).

The Schroder-Van Laar equation can be used to calculate the liquidus curve between the pure enantiomer and the eutectic for a true racemate compound, using the melting point and enthalpy of fusion of the pure enantiomer:

$$\ln x = \frac{\Delta H_A^f}{R} \left( \frac{1}{T_A^f} - \frac{1}{T^f} \right)$$

| Mole Fraction; | 0.9 | $T_f$ = 351.64 K | 78.64° C. |
|---|---|---|---|
| | 0.8 | $T_f$ = 346.60 K | 73.60° C. |
| | 0.7 | $T_f$ = 341.05 K | 68.05° C. |
| | 0.6 | $T_f$ = 334.86 K | 61.86° C. |

Then the part of the curve below which the solid phase consists of pure racemic compound can be determined using the following equation (Prigogine-Defay):

$$\ln 4x(1-x) = \frac{2\Delta H_R^f}{R}\left(\frac{1}{T_R^f} - \frac{1}{T^f}\right)$$

| Mole Fraction; | 0.9 | $T_f$ = 349.26 K | 76.26° C. |
|---|---|---|---|
| | 0.8 | $T_f$ = 360.81 K | 87.81° C. |
| | 0.7 | $T_f$ = 366.53 K | 93.53° C. |
| | 0.6 | $T_f$ = 369.41 K | 96.40° C. |

Where:
x=mole fraction of most abundant enantiomer (0.5≦x≦1) of a mixture whose melting terminates at $T^f$ (K).
$\Delta H_A^f$=enthalpy of fusion of single enantiomer (J·mol$^{-1}$).
$\Delta H_R^f$=enthalpy of fusion of racemate (J·mol$^{-1}$).
R=8.31 (J·K$^{-1}$·mol$^{-1}$).
$T_A^f$=melting point of pure single enantiomer (K).
$T_R^f$=melting point of racemate (K).

Both of these curves were then plotted on the same graph to give the phase diagram. The point at which the lines cross is the eutectic, which in this case is 77.5% ee. See FIG. 4.

Example 31

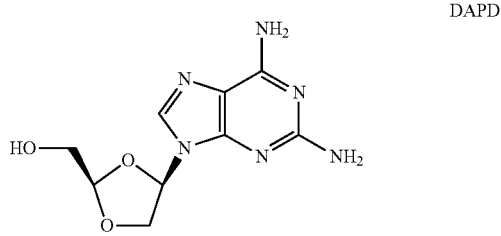 [SMILES: Nc1nc(N)c2ncn([C@H]3CO[C@@H](CO)O3)c2n1]

DAPD

Analytical Development for DAPD

Chiral assays were developed for cis-DAPD and its butyrate ester in order to analyze an enzymatic esterification screen of DAPD. See FIG. 1M.
SFC Conditions for DAPD:
Column: Chiralpak AD
Dimensions: 250×46 mm
Mobile phase: 70% $CO_2$, 30% MeOH with 0.1% TEA
Flow rate: 3.0 mL/min
Pressure: 3000 psi
Column temp: 35° C.
Detection: UV @ 254 nm
Retention times: 1—3.57 minutes
  2—5.64 minutes In order to monitor the progress of the biotransformations for the DAPD material, the above assay was modified to include the baseline resolution of both the DAPD and the butyrate. See FIG. 1N. The conditions and chromatogram are as follows:
SFC Conditions for DAPD and Butyrate Ester:

| Column: | Chiralpak AD |
|---|---|
| Dimensions: | 250 × 4.6 mm |
| Mobile phase: | 80% $CO_2$, 20% MeOH with 0.1% TEA |

-continued

| Flow rate: | 3.0 mL/min | |
|---|---|---|
| Pressure: | 3000 psi | |
| Column temp: | 35° C. | |
| Detection: | UV @ 254 nm | |
| Retention times: | 1 - 4.49 minutes | 2 - 5.90 minutes |
| | 3 - 9.18 minutes | 4 - 11.0 minutes |

Enzymatic Resolution of DAPD

A limited enzyme screen aimed at resolving the isomers of cis-DAPD by transesterification using vinyl butyrate was performed. Enzymes were chosen on the basis of known transesterification activity. Solvents investigated were toluene (substrate insoluble), DMF and pyridine (substrate soluble). The reactions were followed by TLC and the enantiomeric excesses measured by supercritical fluid chromatography (SFC) (Chiralpak AD). As confirmation, enantiomeric excesses were also measured using a HPLC assay (100% MeOH, Chiralpak AD) and were in agreement with the SFC results.

For each enzyme: To racemic cis-DAPD (TP0041/97/D-1, 10 mg, 0.04 mmol) was added solvent (1 mL) (toluene, DMF or pyridine, see Table 13), vinyl butyrate (0.1 mL, 0.8 mmol) and then enzyme (5-10 mg). The vials were shaken in an incubator at 30° C. and assayed periodically by removing 50 µl aliquots, diluting with methanol and analysing by TLC (10:1:0.1 EtOAc:MeOH:$H_2O$) and chiral. Table 23 shows the results obtained.

TABLE 23

Enzymatic screen for acylation of DAPD

| Enzyme | Solvent | Time | $ee_s$ | $ee_p$ | Comments |
|---|---|---|---|---|---|
| Chirazyme-L2 | Toluene | 2 h | 4% | 7% | 1 product (<50% conversion) |
| | | 20 h | 8% | 10% | 2 products (~50% conversion) |
| Chirazyme-L9 | Toluene | 2 h | rac | 18% | 1 product (<50% conversion) |
| | | 20 h | rac | 10% | 2 products (~50% conversion) |
| Lipase AY | Toluene | 2 h | 7% | 3% | 1 product (~50% conversion) |
| | | 20 h | 11% | 6% | 1 product (>50% conversion) |
| Lipase AK | Toluene | 2 h | | | No reaction |
| | | 20 h | rac | rac | 1 product (<50% conversion) |
| Lipase PS | Toluene | 2 h | rac | 12% | 1 product (<50% conversion) |
| | | 20 h | rac | 14% | 1 product (<50% conversion) |
| Alcalase (Immobilised) | DMF | 2 h | | | No reaction |
| | | 20 h | 9% | 10% | 1 product (<50% conversion) |
| Subtilisin carlsberg type VII | DMF | 2 h | | | No reaction |
| | | 20 h | rac | rac | 1 product (<50% conversion) |
| PeptiCLEC-BL | Pyridine | 2 h | — | rac | 1 product (100% conversion) |
| | Pyridine (less enzyme than above) | 2 h | rac | 10% | 1 product (<50% conversion) |
| PeptiCLEC-BL | Toluene | 4 h | rac | rac | 1 product (<50% conversion) |
| | | 24 h | rac | 12% | 1 product |

TABLE 23-continued

Enzymatic screen for acylation of DAPD

| Enzyme | Solvent | Time | ee$_s$ | ee$_p$ | Comments |
|---|---|---|---|---|---|
| Protease N | Toluene | 24 h | | | No reaction |
| | DMF | 24 h | rac | 11% | 1 product (<50% conversion) |
| PLE | Toluene | 24 h | | | No reaction |
| PPL | Toluene | 24 h | | | No reaction |

The results shown in Table 23 show that although esterification of DAPD takes place, it is not an enantioselective reaction. TLC showed that more than one product was formed in some cases. However, for PeptiCLEC-BL and Lipase AY, only the desired butyrate was formed in a fast reaction, thus these would be good enzymes to regioselectively and mildly put an ester on the oxygen.

We claim:

1. A process for preparing a substantially pure enantiomer of a β-D- or β-L-1,3-dioxolane nucleoside comprising:
    a) obtaining an esterified 2,2-dialkoxy ethanol of the formula (Ia):

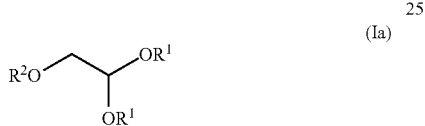

or an aldehyde of formula (Ib):

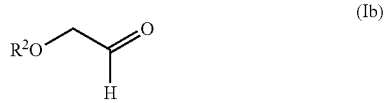

wherein:
    each $R^1$ is independently alkyl, aryl, heteroaryl, heterocyclic, alkaryl, alkylheteroaryl, alkylheterocyclic, or aralkyl; and
    $R^2$ is —C(O)—CH$_2$CH$_2$CH$_3$;
    b) reacting the esterified 2,2-dialkoxy ethanol of the formula (Ia) or the aldehyde of formula (Ib) with glycolic acid to obtain a 1,3-dioxolane lactone of the formula (II):

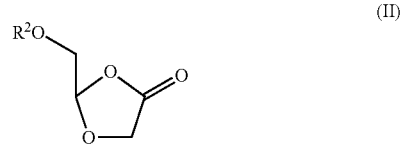

c) resolving the 1,3-dioxolane lactone of the formula (II) to obtain a substantially pure D- or L-lactone, with an enzyme selected from the group consisting of Porcine Pancreatic Lipase, Lipase PS, immobilized lipase *Pseudomonas*, Lipase M, and *Actinobacter* microbial strains;
    d) selectively reducing with a reducing agent the substantially pure D- or L-chiral lactone and reacting the reduced lactone with acetic anhydride to obtain a substantially pure D- or L-1,3-dioxolane of the formula (III):

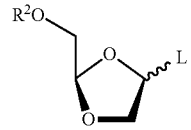

wherein L is acetate;
    e) coupling the substantially pure D- or L-1,3-dioxolane of the formula (III) to a protected purine or pyrimidine base to obtain α:β mixture of substantially pure protected D- or L-1,3-dioxolane nucleosides of the formula (IV):

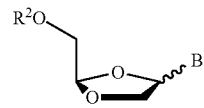

wherein B is a purine or pyrimidine base or its derivative;
    f) optionally purifying the α:β mixture of substantially pure protected D- or L-1,3-dioxolane nucleosides of the formula (IV) to obtain a substantially pure protected β-D- or β-L-1,3-dioxolane nucleoside; and
    g) deprotecting the substantially pure protected β-D- or β-L-1,3-dioxolane nucleoside to obtain a substantially pure β-D- or β-L-1,3-dioxolane nucleoside.

2. The process of claim 1 wherein the substantially pure β-D- or β-L-1,3-dioxolane nucleosides is an 4(R)-[2,6-diamino-purin-9-yl)-[1,3]-dioxolan-2(R)-yl]-methanol.

3. The process of claim 1 further comprising wherein step (b) is conducted in the presence of a Lewis acid.

4. The process of claim 3 wherein the Lewis acid is BF$_3$·Et$_2$O.

5. The process of claim 1 wherein the reducing agent in step (d) is LiAlH(OtBu)$_3$.

6. The process of claim 1 wherein the protected purine or pyrimidine base is a protected 2,6-dichloropurine.

7. The process of claim 1 wherein the substantially pure protected β-D- or β-L-1,3-dioxolane nucleoside is deprotected by reaction with n-butylamine.

8. The process of claim 1, further comprising hydrolyzing the esterified 2,2-dialkoxy ethanol of the formula (Ia) to form the corresponding aldehyde of formula (Ib).

9. The process of claim 1, wherein step a) comprises obtaining the esterified 2,2-dialkoxy ethanol of the formula (Ia).

10. A process for preparing a substantially pure enantiomer of a β-D- or β-L-1,3-dioxolane nucleoside comprising:
    a) obtaining an esterified 2,2-dialkoxy ethanol of the formula (Ia):

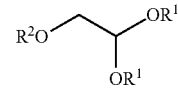

or an aldehyde of formula (Ib):

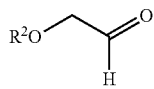
(Ib)

wherein:
each R¹ is independently alkyl, aryl, heteroaryl, heterocyclic, alkaryl, alkylheteroaryl, alkylheterocyclic, or aralkyl; and
R² is p-methoxy benzoyl, benzoyl, or iso-butyryl;

b) reacting the esterified 2,2-dialkoxy ethanol of the formula (Ia) or the aldehyde of formula (Ib) with glycolic acid to obtain a 1,3-dioxolane lactone of the formula (II):

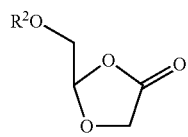
(II)

c) resolving the 1,3-dioxolane lactone of the formula (II) to obtain a substantially pure D- or L-lactone, with Chirazyme L2;

d) selectively reducing with a reducing agent the substantially pure D- or L-chiral lactone and reacting the reduced lactone with acetic anhydride to obtain a substantially pure D- or L-1,3-dioxolane of the formula (III):

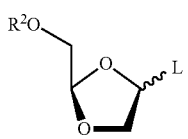
(III)

wherein L is acetate;

e) coupling the substantially pure D- or L-1,3-dioxolane of the formula (III) to a protected purine or pyrimidine base to obtain α:β mixture of substantially pure protected D- or L-1,3-dioxolane nucleosides of the formula (IV):

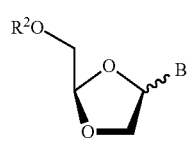
(IV)

wherein B is a purine or pyrimidine base or its derivative;

f) optionally purifying the α:β mixture of substantially pure protected D- or L-1,3-dioxolane nucleosides of the formula (IV) to obtain a substantially pure protected β-D- or β-L-1,3-dioxolane nucleoside; and g) deprotecting the substantially pure protected β-D- or β-L-1,3-dioxolane nucleoside to obtain a substantially pure β-D- or β-L-1,3-dioxolane nucleoside.

11. The process of claim 10 wherein the substantially pure β-D- or β-L-1,3-dioxolane nucleoside is an 4(R)-[-2,6-diamino-purin-9-yl)-[1,3]-dioxolan-2(R)-yl]-methanol.

12. The process of claim 10 further comprising wherein step (b) is conducted in the presence of a Lewis acid.

13. The process of claim 12 wherein the Lewis acid is BF₃·Et₂O.

14. The process of claim 10 wherein the reducing agent in step (d) is LiAlH(OtBu)₃.

15. The process of claim 10 wherein the protected purine or pyrimidine base is a protected 2,6-dichloropurine.

16. The process of claim 10 wherein the substantially pure protected β-D- or β-L-1,3-dioxolane nucleoside is deprotected by reaction with n-butylamine.

17. The process of claim 10, further comprising hydrolyzing the esterified 2,2-dialkoxy ethanol of the formula (Ia) to form the corresponding aldehyde of formula (Ib).

18. The process of claim 10, wherein step a) comprises obtaining the esterified 2,2-dialkoxy ethanol of the formula (Ia).

* * * * *